US012129493B2

(12) United States Patent
Huang et al.

(10) Patent No.: US 12,129,493 B2
(45) Date of Patent: Oct. 29, 2024

(54) HOST CELLS AND METHODS USEFUL FOR PRODUCING UNNATURAL TERPENOIDS USING A NOVEL ARTIFICIAL METALLOENZYME

(71) Applicant: The Regents of the University of California, Oakland, CA (US)

(72) Inventors: Jing Huang, Berkeley, CA (US); Zhennan Liu, Berkeley, CA (US); Douglas S. Clark, Orinda, CA (US); Jay D Keasling, Berkeley, CA (US); Aindrila Mukhopadhyay, Oakland, CA (US); John F. Hartwig, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 93 days.

(21) Appl. No.: 17/200,715

(22) Filed: Mar. 12, 2021

(65) Prior Publication Data
US 2021/0284972 A1 Sep. 16, 2021

Related U.S. Application Data

(60) Provisional application No. 62/989,568, filed on Mar. 13, 2020.

(51) Int. Cl.
*C12N 5/10* (2006.01)
*C07D 487/22* (2006.01)
*C12N 9/02* (2006.01)

(52) U.S. Cl.
CPC ............ *C12N 5/10* (2013.01); *C07D 487/22* (2013.01); *C12N 9/0069* (2013.01); *C12N 2510/00* (2013.01)

(58) Field of Classification Search
CPC .... C12N 5/10; C12N 9/0069; C12N 2510/00; C07D 487/22
See application file for complete search history.

(56) References Cited

U.S. PATENT DOCUMENTS 11,518,768 B2 * 12/2022 Hartwig ............... C07K 14/805
2018/0305368 A1 * 10/2018 Hartwig ............... C07K 14/80

OTHER PUBLICATIONS

Reynolds et al. (Orthogonal Expression of an Artificial Metalloenzyme for Abiotic Catalysis, ChemBioChem 2017, 18, 2380-2384), (Year: 2017).*
Villarreal et al. (Enhancement of Recombinant Hemoglobin Production in Escherichia coli BL21(DE3) Containing the Plesiomonas shigelloides Heme Transport System, Applied and Environmental Microbiology, Sep. 2008, p. 5854-5856). (Year: 2008).*
Key et al. (Beyond Iron: Iridium-Containing P450 Enzymes for Selective Cyclopropanations of Structurally Diverse Alkenes, ACS Cent. Sci. 2017, 3, 302-308). (Year: 2017).*
Cravens et al., "Synthetic biology strategies for microbial biosynthesis of plant natural products." Nat. Commun. 10, 2142 (2019), 12 pages.
Schwizer et al., "Artificial Metalloenzymes: Reaction Scope and Optimization Strategies." Chem. Rev. 118, 142-231 (2018).
Gu et al., "Site-Selective Functionalization of (sp3)C—H Bonds Catalyzed by Artificial Metalloenzymes Containing an Iridium-Porphyrin Cofactor." Angew. Chem. Int. Ed. 58, 13954-13960 (2019).
Key et al., "Beyond Iron: Iridium-Containing P450 Enzymes for Selective Cyclo-propanations of Structurally Diverse Alkenes." ACS Cent. Sci. 3, 302-308 (2017).
Dydio et al., "Chemoselective, Enzymatic C—H Bond Amination Catalyzed by a Cytochrome P450 Containing an Ir (Me)-PIX Cofactor." J. Am. Chem. Soc. 139, 1750-1753 (2017).
Chatterjee et al., "An Enantioselective Artificial Suzukiase Based on the Biotin-Streptavidin Technology." Chem. Sci. 7, 673-677 (2016).
Abe et al., "Control of the Coordination Structure of Organometallic Palladium Complexes in an apo-Ferritin Cage." J. Am. Chem. Soc. 130, 10512-10514 (2008).
Letondor et al., "Artificial Transfer Hydrogenases Based on the Biotin-(Strept) Avidin Technology: Fine Tuning the Selectivity by Saturation Mutagenesis of the Host Protein." J. Am. Chem. Soc. 128, 8320-8328 (2006).
Skander et al., "Artificial Metalloenzymes: (Strept)Avidin as Host for Enantioselective Hydrogenation by Achiral Biotinylated Rhodium-Diphosphine Complexes." J. Am. Chem. Soc. 126, 14411-14418 (2004).
Lin et al., "Catalytic Hydrogenation of Itaconic Acid in a Biotinylated Pyrphos-Rhodium(I) System in a Protein Cavity." Tetrahedron: Asymmetry 10, 1887-1893 (1999).
Philippart et al., "A Hybrid Ring-Opening Metathesis Polymerization Catalyst Based on an Engineered Variant of the Beta-Barrel Protein Fhua." Chem.—Eur. J. 19, 13865-13871 (2013).
Lo et al., "Artificial Metalloenzymes for Olefin Metathesis Based on the Biotin-(Strept)Avidin Technology." Chem. Commun. 47, 12065-12067 (2011).
Jeschek et al., "Directed evolution of artificial metalloenzymes for in vivo metathesis." Nature 537, 661-665 (2016).
Zhao et al., "Genetic Engineering of an Artificial Metalloenzyme for Transfer Hydrogenation of a Self-Immolative Substrate in Escherichia coli's Periplasm." J. Am. Chem. Soc. 140, 13171-13175 (2018).
Grimm et al., "A Whole Cell *E. coli* Display Platform for Artificial Metalloenzymes: Poly(phenylacetylene) Production with a Rhodium-Nitrobindin Metalloprotein." ACS Catal. 8, 2611-2614 (2018).
Heinisch et al., "*E. coli* surface display of streptavidin for directed evolution of an allylic deallylase." Chem. Sci. 9, 5383-5388 (2018).
(Continued)

*Primary Examiner* — Louise W Humphrey
*Assistant Examiner* — Alexander M Duryee
(74) *Attorney, Agent, or Firm* — Robin C. Chiang; LAWRENCE BERKELEY NATIONAL LABORATORY

(57) ABSTRACT

The present invention provides for a genetically modified host cell capable of producing an unnatural compound, such as terpenoid, comprising a P450 enzyme comprising an artificial cofactor, and the host cell is capable of uptaking the artificial cofactor by comprising a heterologous heme transport transmembrane protein, or homologue thereof.

24 Claims, 22 Drawing Sheets

Specification includes a Sequence Listing.

(56) References Cited

OTHER PUBLICATIONS

Khanna et al., "In vivo activation of an [FeFe] hydrogenase using synthetic cofactors." Energy Environ. Sci. 10, 1563-1567 (2017).
Song et al., "A designed supramolecular protein assembly with in vivo enzymatic activity." Science 346, 1525-1528 (2014).
Huang et al., "Extracellular Heme Uptake and the Challenge of Bacterial Cell Membranes." Annu. Rev. Biochem 86, 799-823 (2017).
Brahmkshatriya, P. P. & Brahmkshatriya, P. S. in Natural Products: Phytochemistry, Botany and Metabolism of Alkaloids, Phenolics and Terpenes (eds Kishan Gopal Ramawat & Jean-Michel Mérillon) 2665-2691 (Springer Berlin Heidelberg, 2013).
Helfrich et al., "Bacterial terpene biosynthesis: challenges and opportunities for pathway engineering." Beilstein J. Org. Chem. 15, 2889-2906 (2019).
Coelho et al., "Olefin Cyclopropanation via Carbene Transfer Catalyzed by Engineered Cytochrome P450 Enzymes." Science 339, 307-310 (2013).
Key et al., "Abiological Catalysis by Artificial Haem Proteins Containing Noble Metals in Place of Iron." Nature 534, 534-537 (2016).
Dydio et al., "An Artificial Metalloenzyme with the Kinetics of Native Enzymes." Science 354, 102-106 (2016).
Jeschek et al., "Artificial Metalloenzymes on the Verge of New-to-Nature Metabolism." Trends Biotechnol. 36, 60-72 (2018).
Lelyveld et al., "Metal-Substituted Protein MRI Contrast Agents Engineered for Enhanced Relaxivity and Ligand Sensitivity." J. Am. Chem. Soc. 133, 649-651 (2011).
Bordeaux et al., "Intramolecular C(sp3)H amination of arylsulfonyl azides with engineered and artificial myoglobin-based catalysts. Biorg." Med. Chem. 22, 5697-5704 (2014).
Reynolds et al., "Orthogonal Expression of an Artificial Metalloenzyme for Abiotic Catalysis." ChemBioChem 18, 2380-2384 (2017).
Alonso-Gutierrez et al., "Metabolic engineering of *Escherichia coli* for limonene and perillyl alcohol production." Metab. Eng. 19, 33-41 (2013).
Ascue Avalos et al., "From Bugs to Bioplastics: Total (+)-Dihydrocarvide Biosynthesis by Engineered *Escherichia coli*." ChemBioChem 20, 785-792 (2019).
Henderson et al., "Characterization of the Plesiomonas shigelloides Genes Encoding the Heme Iron Utilization System." J. Bacteriol. 183, 2715-2723 (2001).
Smith et al., "Development of a Method To Produce Hemoglobin in a Bioreactor Culture of *Escherichia coli* BL21(DE3) Transformed with a Plasmid Containing Plesiomonas shigelloides Heme Transport Genes and Modified Human Hemoglobin Genes." Appl. Environ. Microbiol. 77, 6703-6705 (2011).
Carter et al., "Monoterpene biosynthesis pathway construction in *Escherichia coli*." Phytochemistry 64, 425-433 (2003).
Waldman et al., "Discovery of a Diazo-Forming Enzyme in Cremeomycin Biosynthesis." J. Org. Chem. 83, 7539-7546 (2018).
Villarreal et al., Enhancement of Recombinant Hemoglobin Production in *Escherichia coli* BL21(DE3) Containing the Plesiomonas shigelloides Heme Transport System. Appl. Environ. Microbiol. 74, 5854-5856 (2008).
Lee et al., "BglBrick vectors and datasheets: A synthetic biology platform for gene expression." J. Biol. Eng. 5, 12 (2011), 14 pages.
Reister, M. et al. "Complete genome sequence of the Gram-negative probiotic *Escherichia coli* strain Nissle 1917." J. Biotechnol. 187, 106-107 (2014).
Malherbe et al., "A robust fractionation method for protein subcellular localization studies in *Escherichia coli*." BioTechniques 66, 171-178 (2019).
Hu et al., "Experimental and computational characterization of photosensitized conformational effects mediated by protoporphyrin ligands on human serum albumin." Photochem. Photobiol. Sci. 16, 694-710 (2017).
Leung et al., "Precise determination of heme binding affinity in proteins." Anal. Biochem. 572, 45-51 (2019).

* cited by examiner

HOST CELLS AND METHODS USEFUL FOR PRODUCING UNNATURAL TERPENOIDS USING A NOVEL ARTIFICIAL METALLOENZYME

CROSS REFERENCE TO RELATED APPLICATIONS

This application claims priority to U.S. Provisional Patent Application Ser. No. 62/989,568, filed Mar. 13, 2020, which is incorporated by reference in its entirety.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of the production of an unnatural compound using an artificial metalloenzyme.

REFERENCE TO A "SEQUENCE LISTING" SUBMITTED AS ASCII TEXT FILES VIA EFS-WEB

The Sequence Listing written in file 2020-049-02_Sequence_Listing_ST25.txt created on Mar. 8, 2021, 9,420 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

Molecules produced by natural biosynthetic pathways are the inspiration or the actual matter in many products, ranging from medicines and agrochemicals to commodity chemicals and biofuels. Although many molecules with structures that are the envy of chemists are produced by these natural or engineered biosynthetic pathways, the structures remain limited by the available chemical reactions catalyzed by natural enzymes. If artificial enzymes could be incorporated into such biosynthetic pathways, then unnatural products could be produced from a combination of nature's reactions and chemists' imaginations.

Recently, artificial metalloenzymes (ArMs) have been created that catalyze a series of unnatural reactions[2-13]. However, most of these reactions do not occur on the types of molecules that could be produced by biosynthesis. In contrast, an iridium-containing analog of a heme enzyme catalyzes the cyclopropanation of unconjugated, hindered, terminal alkenes that are present in natural products, such as terpenes[4]. This reactivity provides the potential to create an artificial biosynthetic pathway that combines natural pathways manipulated by synthetic biology with the catalysis created by ArMs.

The assembly of artificial metalloenzymes has advanced from in vitro reconstitution of purified proteins with organometallic complexes to assembly of ArMs in the periplasm[13,14] or on the outer-membrane[15,16] of living cells. However, methods to assemble ArMs in more complex intracellular environments are lacking[17,18]. We hypothesized that artificial cytochrome P450s containing synthetic heme derivatives could be generated in the cytoplasm by employing the natural heme transport machinery[19] and the affinity of hemoproteins to heme derivatives. Thus, artificial cytochrome P450s are potential ArMs for conducting unnatural biotransformations in vivo in a fashion that enables the assembly of artificial biosynthetic pathways.

Terpenes are the largest and most structurally diverse family of natural products[20]. Their core skeletons are assembled in one step and modified by a suite of tailoring enzymes including cytochrome P450s[21]. While native P450s typically catalyze oxidations of terpenes, extensively engineered P450s, such as $P450_{BM3}$[22], and artificial P450s substituted with abiotic metalloporphyrins, could catalyze unnatural transformations[3-5,23,24] that would introduce an artificial dimension to the diversification of terpene structures.

SUMMARY OF THE INVENTION

The present invention provides for a genetically modified host cell capable of producing an unnatural compound comprising a P450 enzyme comprising an artificial cofactor, such as a porphyrin-metal or M(L) complex, and the host cell is capable of uptaking the artificial cofactor by comprising a heterologous heme transport transmembrane protein, or homologue thereof. In some embodiments, the unnatural compound is an unnatural terpenoid.

In some embodiments, the P450 enzyme is an engineered P450 enzyme such that the engineered P450 apo-protein is capable of forming an active P450 enzyme comprising the artificial cofactor. In some embodiments, the engineered P450 apo-protein is apo-CYP119 and the active P450 enzyme is Ir-CYP119. In some embodiments, the P450 enzyme is a thermophilic P450 enzyme.

In some embodiments, the artificial metalloenzymes has improved reactivity (for example, when compared to a naturally occurring metalloenzyme) and that can facilitate formation of bonds, including those to the carbon of unactivated C—H bonds. The metalloenzymes of the present invention can have a non-native heme component, such as an Iridium metal in the porphyrin, as well as a mutant enzyme. The metalloenzymes provide improved stereoselectivity and reactivity compared to metalloenzymes in the art.

In some embodiments, the porphyrin-metal complex comprises a porphyrin and a metal. In some embodiments, the porphyrin is pyropheophorbide-a, pheophorbide, chlorin e6, purpurin or purpurinimide. In some embodiments, the porphyrin is pyropheophorbide-a. Representative structures are shown below:

| PORPHYRIN | STRUCTURE |
|---|---|
| Porphyrin | 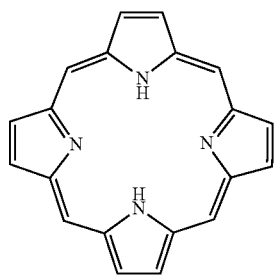 [SMILES: C1=Cc2cc3ccc(cc4nc(cc5ccc(cc1n2)[nH]5)C=C4)[nH]3] |
| Pyropheophorbide-a | 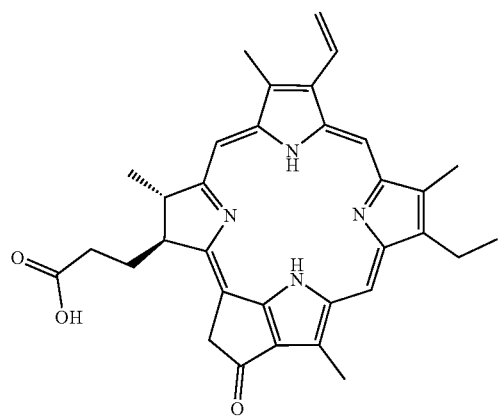 [SMILES: C=Cc1c(C)c2cc3nc(c4c5[nH]c(cc6nc(cc1[nH]2)C(C)=C6CC)c(C)c5C(=O)C4)[C@@H](CCC(=O)O)[C@@H]3C] |
| Pheophorbide | 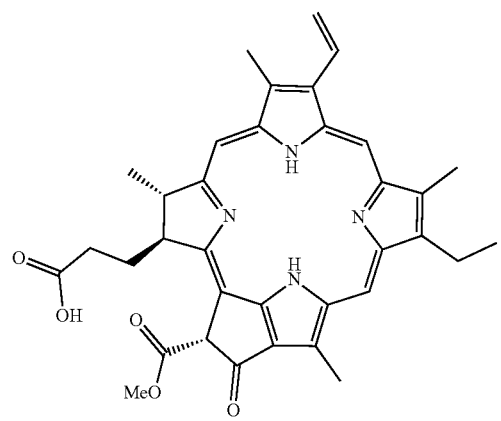 [SMILES: C=Cc1c(C)c2cc3nc(c4c5[nH]c(cc6nc(cc1[nH]2)C(C)=C6CC)c(C)c5C(=O)[C@@H]4C(=O)OC)[C@@H](CCC(=O)O)[C@@H]3C] |
| Chlorin e6 | 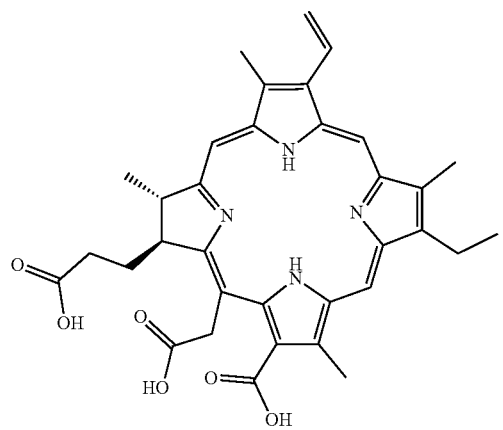 [SMILES: C=Cc1c(C)c2cc3nc(c(CC(=O)O)c4[nH]c(cc5nc(cc1[nH]2)C(C)=C5CC)c(C)c4C(=O)O)[C@@H](CCC(=O)O)[C@@H]3C] |

| PORPHYRIN | STRUCTURE |
|---|---|
| Purpurin | 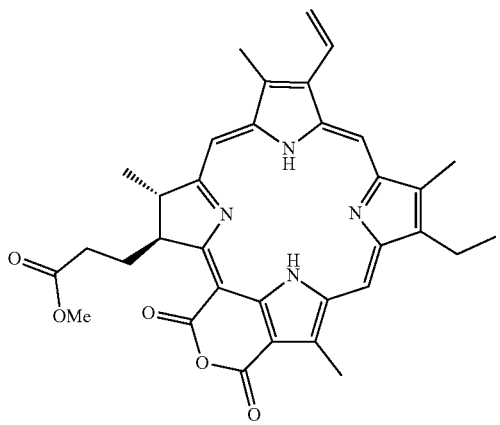 [SMILES: C=Cc1c(C)c2cc3nc(c4c5[nH]c(cc6nc(cc1[nH]2)C(C)=C6CC)c(C)c5C(=O)OC4=O)[C@@H](CCC(=O)OC)[C@@H]3C] |
| Purpurinimide | 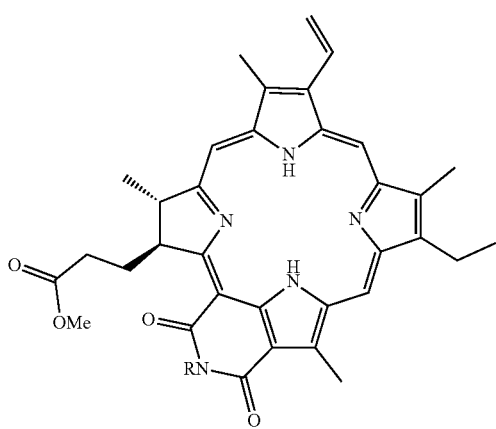 |

In some embodiments, the porphyrin can also be represented by the following formula:

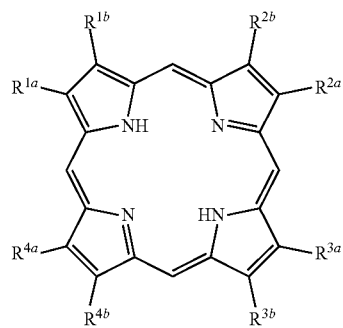

wherein $R^{1a}$, $R^{1b}$, $R^{2a}$, $R^{2b}$, $R^{3a}$, $R^{3b}$, $R^{4a}$ and $R^{4b}$ are each independently selected from the group consisting of hydrogen, $C_{1-6}$ alkyl, $C_{2-6}$ alkenyl, $C_{2-6}$ alkynyl, $C_{3-8}$ cycloalkyl and $C_{6-10}$ aryl, wherein the alkyl is optionally substituted with —C(O)OR$^5$ wherein R$^5$ is hydrogen or $C_{1-6}$ alkyl. In some embodiments, $R^{1a}$, $R^{1b}$, $R^{2a}$, $R^{2b}$, $R^{3a}$ and $R^{4a}$ are each independently selected from the group consisting of hydrogen, $C_{1-6}$ alkyl and $C_{2-6}$ alkenyl, and $R^{3b}$ and $R^{4b}$ are each independently selected from the group consisting of $C_{1-6}$ alkyl, wherein the alkyl is substituted with —C(O)OR$^5$ wherein R$^5$ is hydrogen. In some embodiments, $R^{1a}$, $R^{1b}$, $R^{2a}$, $R^{2b}$, $R^{3a}$ and $R^{4a}$ are each independently selected from the group consisting of hydrogen, methyl, ethyl and ethenyl, and $R^{3b}$ and $R^{4b}$ are each —CH$_2$CH$_2$—C(O)OH. In some embodiments, the porphyrin can be selected from the group consisting of:

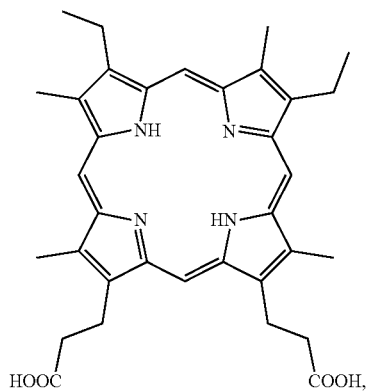

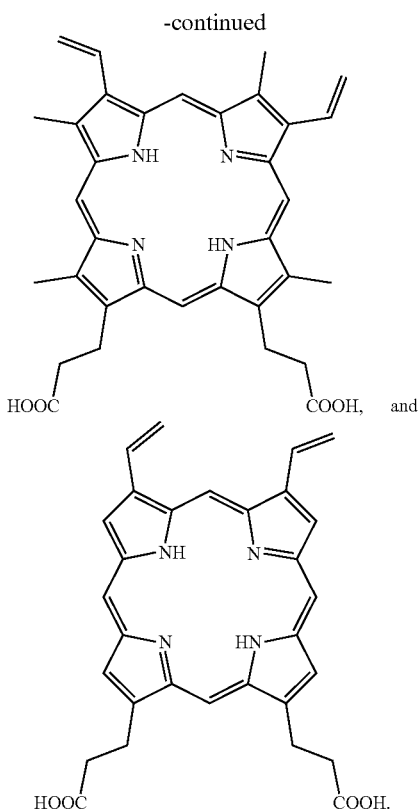

The metal M of the M(L) group can be any suitable metal, such as a transition metal. Representative metals include, but are not limited to, Ir, Pd, Pt, Ag, Fe, Mn, Ru, Co, Zn, Cu, Ni, Cr, Rh and Os. In some embodiments, the metal M can be Ir, Pd, Pt, Ag, Mn, Ru, Co, Zn, Cu, Ni, Cr, Rh and Os. In some embodiments, the metal M can be Ir, Co, Cu, Mn, Ru, or Rh. In some embodiments, the metal M can be Ir, Pd, Pt or Ag. In some embodiments, the metal M can be Ir. In some embodiments, the metal is other than Fe.

The ligand L can be absent or any suitable ligand. Examples of ligands bound via an oxygen with a formal negative charge include, but are not limited to, hydroxo, alkoxo, phenoxo, carboxylate, carbamate, sulfonate, and phosphate. Examples of ligands bound via an oxygen with a neutral charge include, but are not limited to, water, ethers, alcohols, phosphine oxide, and sulfoxides. Neutral examples of ligands bound via a nitrogen include, but are not limited to, amines, basic heterocycles, such as pyridine or imidazole. Examples of ligands bound via nitrogen with formal negative charges include, but are not limited to, amides like acetamide or trifluoroacetamide, heteroarenes like pyrrolide, among others. Examples of ligands bound via carbon with a negative charge include, but are not limited to, alkyl, aryl, vinyl, alkynyl, and others. Examples of ligands bound through phosphorus include, but are not limited to, phosphines ($PR_3$), phosphites ($P(OR)_3$), phosphinites ($P(OR)(R)_2$), phosphonites ($P(OR)_2(R)$) and phosphoramides ($P(NR_2)_3$), where each R can independently be H, alkyl, alkenyl, alkynyl, aryl, etc. Ligands bound via phosphorous can also include mixtures of alkyl and alkoxo or amino groups. Examples of ligands bound through sulfur include, but are not limited to, thiols, thiolates and thioethers, among others.

In other examples, the ligand can be $C_{1-3}$ alkyl, —O—$C_{1-3}$ alkyl, halogen, —OH, —CN, —CO, —$NR_2$, —$PR_3$, $C_{1-3}$ haloalkyl, or pentafluorophenyl. In some embodiments, the ligand is absent. In some embodiments, the ligand is $C_{1-3}$ alkyl, —O—$C_{1-3}$ alkyl, halogen, —OH, —CN, —CO, —$NR_2$, —$PR_3$, $C_{1-3}$ haloalkyl, or pentafluorophenyl. In some embodiments, the ligand can be $C_{1-3}$ alkyl, halogen, —CO or —CN. In some embodiments, the ligand can be $C_{1-3}$ alkyl or halogen. In some embodiments, the ligand can be methyl, ethyl, n-propyl, isopropyl, F, Cl, or Br. In some embodiments, the ligand can be methyl ethyl, F, Cl, Br, CO or CN. In some embodiments, the ligand can be methyl, ethyl, F, Cl or Br. In some embodiments, the ligand can be methyl or chloro.

Any combination of metal and ligand can be used in the compositions of the present invention. In some embodiments, the M(L) can be Ir(Me), Ir(Cl), Fe(Cl), Co(Cl), Cu, Mn(Cl), Ru(CO) or Rh. In some embodiments, M(L) can be Ir(Me) or Ir(Cl). In some embodiments, M(L) can be Ir(Me).

The porphyrin and M(L) group can also form a complex, such as in the following structure:

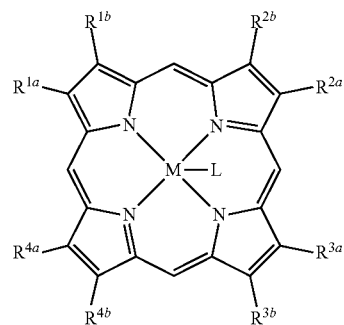

wherein $R^{1a}$, $R^{1b}$, $R^{2a}$, $R^{2b}$, $R^{3a}$, $R^{3b}$, $R^{4a}$ and $R^{4b}$ are as defined above. In some embodiments, the porphyrin-M(L) complex has the formula:

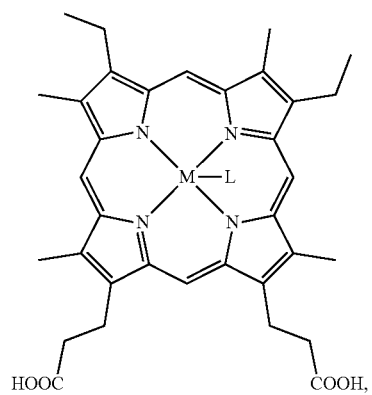

-continued
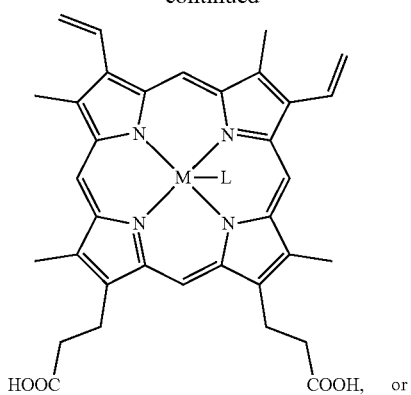
or
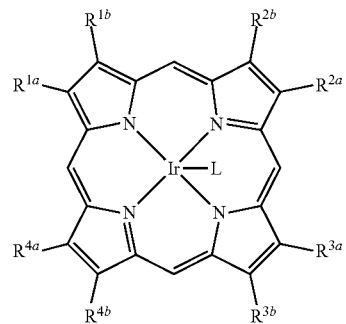
wherein $R^{1a}$, $R^{1b}$, $R^{2a}$, $R^{2b}$, $R^{3a}$, $R^{3b}$, $R^{4a}$ and $R^{4b}$ are as defined above.
In some embodiments, the porphyrin-Ir(L) complex has the formula:
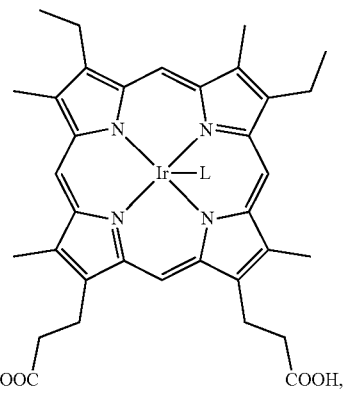
In some embodiments, the porphyrin-M(L) complex has the formula:
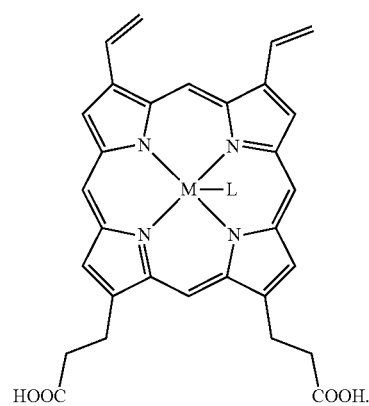
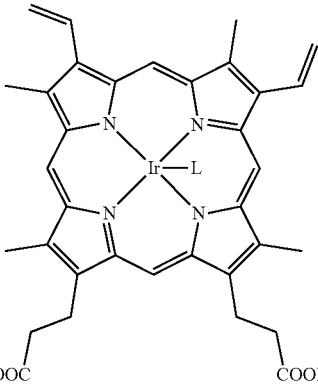
In some embodiments, the porphyrin-M(L) complex has the formula:
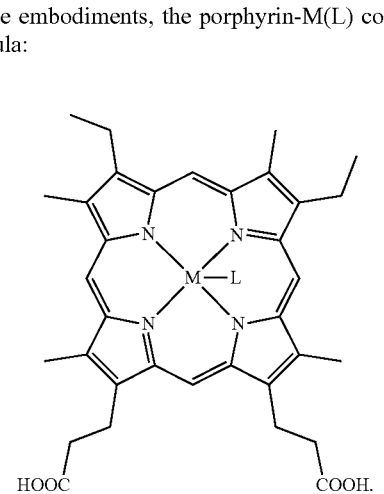
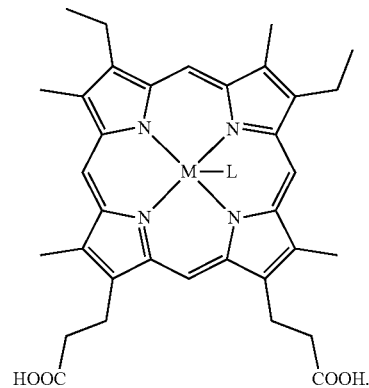
or
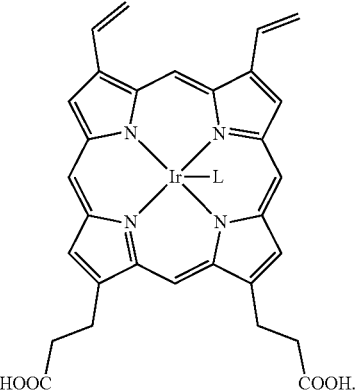

In some embodiments, the porphyrin-Ir(L) complex has the formula:

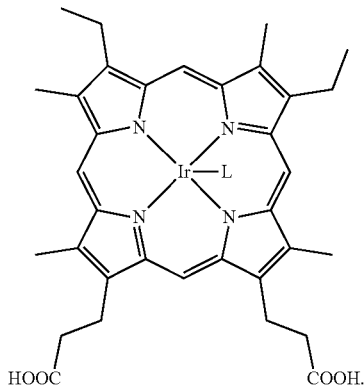

In some embodiments, the porphyrin-Ir(L) complex can have the formula:

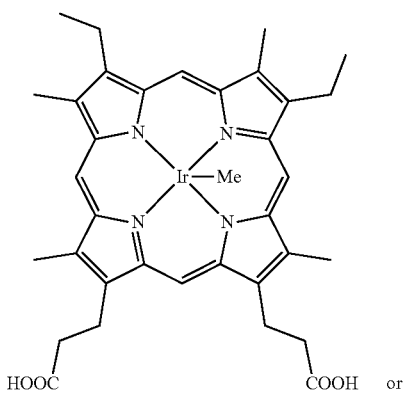

or

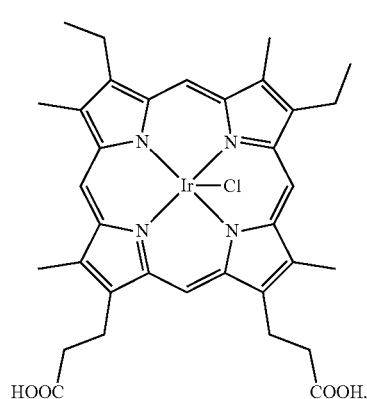

In some embodiments, the artificial cofactor comprises a porphyrin structure and a metal. In some embodiments, the artificial cofactor comprises an abiotic metalloporphyrin. In some embodiments, the artificial cofactor comprises the following structure:

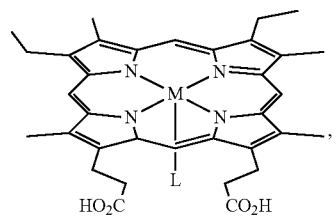

wherein M is a metal, and L is defined herein. In some embodiments, M is any transition metal. In some embodiments, M is Sc, Ti, V. Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ac, Rf, db, Sg, Bh, or Hs. In some embodiments, the artificial cofactor comprises the following structure:

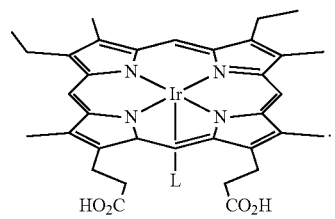

In some embodiments, the artificial cofactor comprises the following structure:

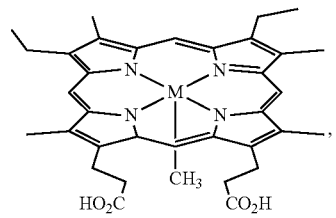

wherein M is defined herein. In some embodiments, the artificial cofactor comprises the following structure:

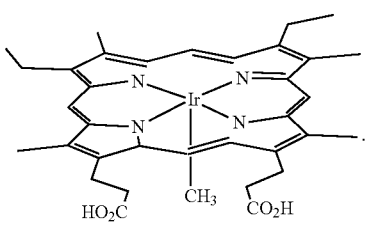

In some embodiments, the unnatural compound or terpenoid having the following structure:

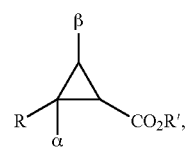

(I)

wherein α and β are each independently a —H or an alkyl group, and wherein R and a may form a ring structure. In some embodiments, the alkyl group is a methyl, ethyl, propyl, or butyl group, or any alkyl having from 1 to 10, or 1 to 5, carbon atoms. In some embodiments, chemical structure (I) has the following structure:

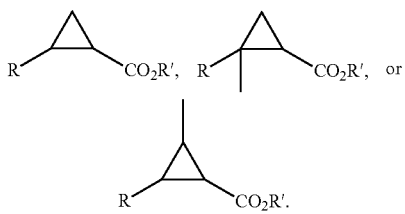

In some embodiments, the unnatural terpenoid comprises a cyclopropanated pinene, linalool, nootkatone, eugenol, terpineol, polyketide, flavonoid, cannabinoid, or a compound wherein the structure (I) comprises one or more alkene.

In some embodiments, the unnatural compound or terpenoid is formed from any terpene or any compound with the following structure:

(II)

wherein α and β are each independently a —H or an alkyl group, and wherein R and a may form a ring structure. In some embodiments, the alkyl group is a methyl, ethyl, propyl, or butyl group, or any alkyl having from 1 to 10, or 1 to 5, carbon atoms. In some embodiments, chemical structure (I) has the following structure:

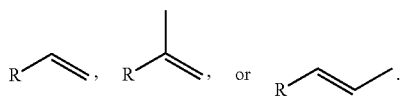

In some embodiments, the terpene is a monoterpene, such as a β-pinene, camphene, limonene, or myrcene. In some embodiments, the terpene is a sesquiterpene, such as a nerodiol. In some embodiments, the compound with the structure:

(II)

is a (−)-carveol, (−)-carvone, (−)-(6) (peppermint), (−)-trans-isopiperitenol, (−)-isopiperitenone, (+)-cis-isopulegone, perilla alcohol, perilla aldehyde, β-selinene, α-terpineol, linalool, lavandulol, grandisol, santolina alcohol, vetispiradiene, trichodine, α-farnesene, isoprene, d-limonene, β-phellandrene, sabinene, ocimene, germacrene D, or (S)-citronellene.

In some embodiments, R is an alkyl group comprising 3, 4, 5, 6, 7, 8, 9, 10, or more carbon atoms. In some embodiments, R comprises one or more double bonds, one or more alkyl substituents, one or more ketone substituents, and/or one or more hydroxyl substituents. In some embodiments, R comprises a cycloalkane, such as cyclohexane. In some embodiments, the cycloalkane comprises one or more double bonds, one or more alkyl substituents, one or more ketone substituents, and/or one or more hydroxyl substituents. In some embodiments, each alkyl substituent is independently a methyl, ethyl, propyl, or butyl group, or any alkyl having from 1 to 10, or 1 to 5, carbon atoms.

In some embodiments, the P450 enzyme is CYP119, described herein.

The present invention provides for a method for a genetically modified host cell producing an unnatural compound or terpenoid, comprising (a) providing a genetically modified host cell of the present invention, (b) introducing the artificial cofactor into the host cell, (c) culturing or growing the host cell in a suitable culture or medium such that unnatural compound or terpenoid is produced, and (d) optionally extracting or separating the unnatural compound or terpenoid from the rest of the culture or medium, and/or host cell.

In some embodiments, the introducing step (b) is concurrent or simultaneous to the culturing or growing step (c). In some embodiment, suitable culture or medium comprises the artificial cofactor, and the host cell uptakes the artificial cofactor from the suitable culture or medium.

In some embodiments, the providing step (a) comprises introducing a nucleic acid encoding the engineered P450 apo-protein operatively linked to a promoter capable of expressing the engineered P450 apo-protein in the host cell into the host cell. In some embodiments, the culturing or growing step (b) comprises the host cell growing by respiratory cell growth. In some embodiments, the culturing or growing step (b) takes place in a batch process or a fed-batch process, such as a high-gravity fed-batch process. In some embodiments, the culture or medium comprises a rich medium, such as LB (Lysogeny-Broth) or comprising one or more ingredients of LB, such as tryptone and/or yeast extract. In some embodiments, the culture or medium comprises hydrolysates derived or obtained from a biomass, such as a lignocellulosic biomass. In some embodiments, the culture or medium comprises one or more carbon sources, such as a sugar, such as glucose or galactose, or glycerol, or a mixture thereof. In some embodiments, the carbon source is fermentable. In some embodiments, the carbon source is non-fermentable. In some embodiments, the culture or medium comprises urea as a nitrogen course.

The present invention provides for a method for constructing a genetically modified host cell of the present invention, comprising (a) introducing a nucleic acid encoding the engineered P450 apo-protein operatively linked to a promoter capable of expressing the engineered P450 apo-protein in the host cell into the host cell.

In some embodiments, the engineered P450 apo-protein comprises an amino acid sequence that is at least 70%, 80%, 90%, 95%, or 99% identical to the amino acid sequence of any P450, such as CYP119.

In some embodiments, the invention comprises the use of a heterologous codon-optimized version of the engineered P450 enzyme and the heme transport transmembrane protein in the host cell.

The present invention also provides for any novel cyclopropanated compound, such as a cyclopropanated pinene, linalool, nootkatone, eugenol, terpineol, polyketide, flavonoid, cannabinoid, or a compound wherein the structure (I) comprises one or more alkene; which can be produced by the method of this invention. In some embodiments, the cyclopropanated compound is

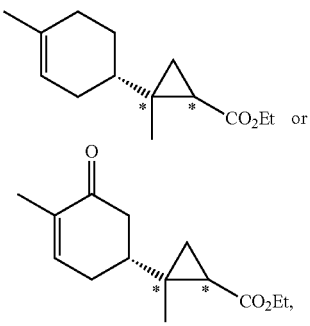

or wherein the Et is any alkyl group. In some embodiments, the alkyl group comprises 1, 2, 3, 4, 5, 6, 7, 8, 9, or 10 carbon atoms. In some embodiments, the cyclopropanated compound is in an isolated or purified state.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
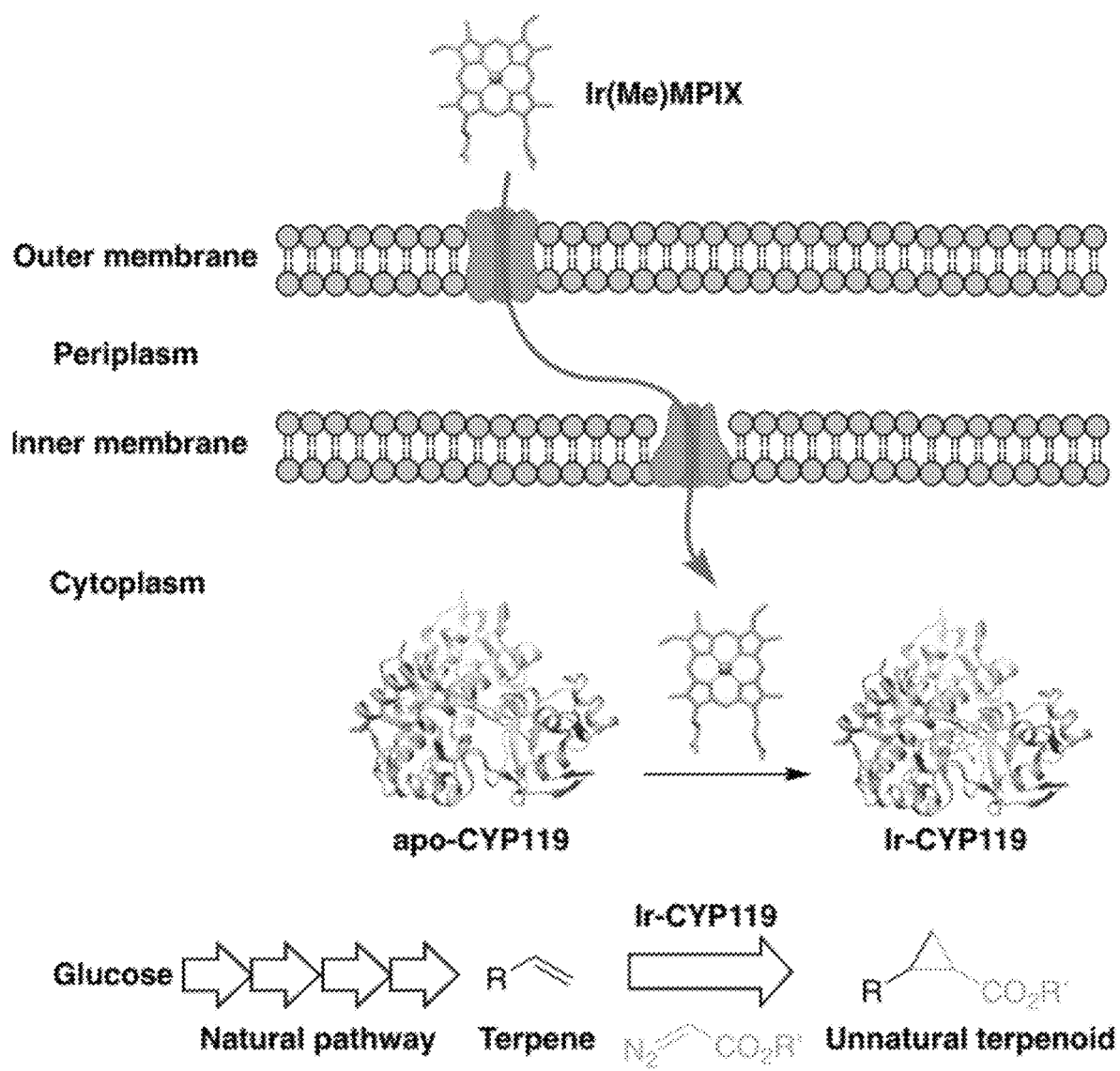
FIG. 1. A schematic representation of a reaction sequence to produce an unnatural terpenoid by combining a heterologously expressed natural biosynthetic pathway and an ArM in E. coli.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

The term "about" refers to a value including 10% more than the stated value and 10% less than the stated value.

The terms "host cell" is used herein to refer to a living biological cell that can be transformed via insertion of an expression vector.

The terms "expression vector" or "vector" refer to a compound and/or composition that transduces, transforms, or infects a host cell, thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular species, but also encompasses a promoter from a corresponding gene in other species.

The term "operatively linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

"Porphyrin" refers to a macrocyclic aromatic ring structure with alternating pyrrole and methyne groups forming the ring. Porphyrins can be substituted to form compounds such as pheophorbide or pyropheophorbide, among others. Porphyrins are a key component of hemoglobin and can complex a metal, such a iron, via the nitrogen atoms of the pyrrole rings.

"Metal" refers to elements of the periodic table that are metallic and that can be neutral, or negatively or positively charged as a result of having more or fewer electrons in the valence shell than is present for the neutral metallic element. Metals useful in the present invention include the alkali metals, alkali earth metals, transition metals and post-transition metals. Alkali metals include Li, Na, K, Rb and Cs. Alkaline earth metals include Be, Mg, Ca, Sr and Ba. Transition metals include Sc, Ti, V, Cr, Mn, Fe, Co, Ni, Cu, Zn, Y, Zr, Nb, Mo, Tc, Ru, Rh, Pd, Ag, Hf, Ta, W, Re, Os, Ir, Pt, Au, and Hg. Post-transition metals include Al, Ga, In, Tl, Ge, Sn, Pb, Sb, Bi, and Po. Rare earth metals include Sc, Y, La, Ce, Pr, Nd, Sm, Eu, Gd, Tb, Dy, Ho, Er, Tm, Yb and Lu. One of skill in the art will appreciate that the metals described above can each adopt several different oxidation states, all of which are useful in the present invention. In some instances, the most stable oxidation state is formed, but other oxidation states are useful in the present invention.

"Ligand" refers to a substituent on the metal of the porphyrin-metal complex. The ligand stabilizes the metal and donates electrons to the metal to complete the valence shell of electrons.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkene" or "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkyne" or "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Halogen" refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc. In some instances, the term "perfluoro" can be used to define a compound or radical where all the hydrogens are replaced with fluorine. For example, perfluoromethyl refers to 1,1,1-trifluoromethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Heteroalkyl" refers to an alkyl group of any suitable length and having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines. The heteroatom portion of the heteroalkyl can replace a hydrogen of the alkyl group to form a hydroxy, thio or amino group. Alternatively, the heteroartom portion can be the connecting atom, or be inserted between two carbon atoms.

"Amine" or "amino" refers to an —N(R)$_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen).

"Alkyl amine" refers to an alkyl group as defined within, having one or more amino groups. The amino groups can be primary, secondary or tertiary. The alkyl amine can be further substituted with a hydroxy group to form an aminohydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbomane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Alkenyl-aryl" or "arylalkene" refers to a radical having both an alkene component and a aryl component, as defined above. Representative arylalkene groups include styrene or vinyl-benzene. Alkenyl-aryl groups can be substituted or unsubstituted.

"Pentafluorophenyl" refers to a phenyl ring substituted with 5 fluorine groups.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

The groups defined above can optionally be substituted by any suitable number and type of subsituents. Representative substituents include, but are not limited to, halogen, haloalkyl, haloalkoxy, —OR', =O, —OC(O)R', —(O)R', —O$_2$R', —ONR'R", —OC(O)NR'R", =NR', =N—OR', —NR'R", —NR"C(O)R', —NR'—(O)NR"R'", —NR"C(O)OR', —NH—(NH$_2$)=NH, —NR'C(NH$_2$)=NH, —NH—(NH$_2$)=NR', —SR', —S(O)R', —S(O)$_2$R', —S(O)$_2$NR'R", —NR'S(O)$_2$R", —N$_3$ and —NO$_2$. R', R" and R'" each independently refer to hydrogen, unsubstituted alkyl, such as unsubstituted C$_{1-6}$ alkyl. Alternatively, R' and R", or R" and R'", when attached to the same nitrogen, are combined with the nitrogen to which they are attached to form a heterocycloalkyl or heteroaryl ring, as defined above.

In the context of this invention, the term "heme protein" refers to a protein having a prosthetic group that comprises a porphyrin ring, which in its native state, has an iron metal contained within the porphyrin ring. The prosthetic group may comprise protoporphyrin IX, which has a porphyrin ring, substituted with four methyl groups, two vinyl groups, and two propionic acid groups, and complexes with an iron atom to form heme. A "heme apoprotein" as used herein refers to a heme protein that lacks the metal/porphyrin complex. The term "heme protein" or "heme apoprotein" encompasses fragments of heme apoproteins, so long as the fragment comprises an active site, as well as variants of native heme apoproteins.

The term "active site" as used in reference to a "heme protein" refers to the porphyrin binding region of the heme protein. An amino acid change "close to the active site" refers to a position that is 25 Angstroms or less from the iron center of a native heme protein, where any part of the amino acid is 25 Angstroms or less from the iron center of the native heme protein. In some embodiments, an amino acid residue close to the active site has any part of the amino acid molecule that is 20 Angstroms or less from the iron center of the active site in the native heme protein. In some embodiments, an amino acid residue close to the active site has any part of the amino acid that is 15 Angstroms or less from the iron center of the active site in the native heme protein The terms "wild type", "native", and "naturally occurring" with respect to a heme protein are used herein to refer to a heme protein that has a sequence that occurs in nature.

In the context of this invention, the term "mutant" with respect to a mutant polypeptide or mutant polynucleotide is used interchangeably with "variant". A variant with respect to a given wildtype heme apoprotein reference sequence can include naturally occurring allelic variants. A "non-naturally" occurring heme apoprotein refers to a variant or mutant heme apoprotein polypeptide that is not present in a cell in nature and that is produced by genetic modification, e.g., using genetic engineering technology or mutagenesis techniques, of a native heme polynucleotide or polypeptide. A "variant" includes any heme protein comprising at least one amino acid mutation with respect to wild type. Mutations may include substitutions, insertions, and deletions. Variants include protein sequences that contain regions or segments of amino acid sequences obtained from more than one heme apoprotein sequence.

A polynucleotide or polypeptide, or any material, is "heterologous" to an organism or a second polynucleotide or polypeptide sequence, or other material, if it originates from a foreign species, or, if from the same species, is modified from its original form. For example, a "heterologous" sequence includes a native heme apoprotein having one or more mutations relative to the native heme apoprotein amino acid sequence; or a native heme apoprotein that is expressed in a host cell in which it does not naturally occur.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g, norleucine) or modified polypeptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acid is also meant to include -amino acids having L or D configuration at the α-carbon.

A "non-natural amino acid" is included in the definition of an amino acid and refers to an amino acid that is not one of the 20 common naturally occurring amino acids or the rare naturally occurring amino acids e.g., selenocysteine or pyrrolysine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids.

Heme polypeptide sequences that are substantially identical to a reference sequence include "conservatively modified variants." One of skill will recognize that individual changes in a nucleic acid sequence that alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), He (Isoleucine or I), Met (Methionine or M), Ser (Serine or S), Thr (Threonine or T) and Cys (Cysteine or C). Within each group, subgroups can also be identified. For example, the group of charged or polar amino acids can be sub-divided into sub-groups including: a "positively-charged sub-group" comprising Lys, Arg and His; a "negatively-charged sub-group" comprising Glu and Asp; and a "polar sub-group" comprising Asn and Gln. In another example, the aromatic or cyclic group can be sub-divided into sub-groups including: a "nitrogen ring sub-group" comprising Pro, His and Trp; and a "phenyl sub-group" comprising Phe and Tyr. In another further example, the aliphatic group can be sub-divided into sub-groups, e.g., an "aliphatic non-polar sub-group" comprising Val, Leu, Gly, and Ala; and an "aliphatic slightly-polar sub-group" comprising Met, Ser, Thr and Cys. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH$_2$ can be maintained. In some embodiments, hydrophobic amino acids are substituted for naturally occurring hydrophobic amino acid, e.g, in the active site, to preserve hydrophobicity.

The terms "identical" or percent "identity," in the context of two or more polypeptide sequences (or two or more nucleic acids), refer to two or more sequences or subsequences that are the same or have a specified percentage of amino acid residues or nucleotides that are the same, e.g., at least 50% identity, preferably at least 60% identity, preferably at least 65%, 70%, 75%, 80%, 85%, 90%, 91%, 92%, 93%, 94%, 95%, 96%, 97%, 98%, 99% or 100% identity, over a specified region when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters are used. Alternatively, sequences may be aligned by hand to determine the percent identity.

The terms "corresponding to", "determined with reference to", or "numbered with reference to" when used in the context of the identification of a given amino acid residue in a polypeptide sequence, refers to the position of the residue of a specified reference sequence when the given amino acid sequence is maximally aligned and compared to the reference sequence. Thus, for example, a residue in a polypeptide "corresponds to" an amino acid at a position in SEQ ID NO: 1 when the residue aligns with the amino acid in SEQ ID NO: 1 when optimally aligned to SEQ ID NO: 1. The polypeptide that is aligned to the reference sequence need not be the same length as the reference sequence and may or may not contain a starting methionine.

"Forming a bond" refers to the process of forming a covalent bond such as a carbon-carbon bond, a carbon-nitrogen bond, a carbon-oxygen bond, or a covalent bond two other atoms.

"Carbene precursor" refers to a compound capable of generating a carbene, a carbon atom having only six valence shell electrons, including a lone pair of electrons, and represented by the formula: $R_2C$:. For example, the carbene precursor can include a diazo group and have the formula $R_2C=N=N$ where $N_2$ is the leaving group the loss of which forms $R_2C$:. Representative carbene precursors include, but are not limited to, α-diazoester, an α-diazoamide, an α-diazonitrile, an α-diazoketone, an α-diazoaldehyde, and an α-diazosilane. The carbenes are formed by coordination of the carbene precursor to the metal, generation of the metal-carbene complex, and reaction of this complex with the substrate in an inter- or intra-molecular fashion to form carbon-carbon bonds, including those in cyclopropyl groups.

"Nitrene precursor" refers to a compound capable of generating a nitrene, a nitrogen atom having only six valence shell electrons, including two lone pairs of electrons, and represented by the formula: RN::. For example, the nitrene precursor can have the formula $RN=N=N$ where $N_2$ is the leaving group, the loss of which forms RN::. Representative nitrene precursors include azides. The nitrenes are formed by coordination of the nitrene precursor to the metal, followed by reaction with the substrate to form amines.

"Substrate" refers to the compound that reacts with the carbene or nitrene to form the bond. Representative substrates contain an olefin or a C—H bond.

"Olefin" refers to a compound containing a vinyl group: —CR=CR—.

"C—H insertion" refers to the process of carbene insertion into a C—H bond to form a carbon-carbon bond, or nitrene insertion to form a carbon-nitrogen bond. Insertion of a nitrene into a C—H bond results in formation of an amine and can also be referred to as amination.

"Cyclopropanation" refers to the process of forming a cyclopropyl ring by carbene insertion into a double bound.

In some embodiments, the invention comprises a full cellular incorporated system with a biological pathway that makes an unnatural compound or terpenoid (such as cyclopropanated limonene) and expression of a CYP119 mutant which can assemble with the incorporated artificial cofactor Ir(Me)MPIX to create a new artificial metalloenzyme able to use a terpene (such as limonene) as substrate and catalyze the formation of cyclopropyl terpene (such as cyclopropyl limonene) with selectivity. In some embodiments, the substrate is introduced to the host cell exogenously. In some embodiments, the substrate is produced by the host cell, which optionally comprises a nucleic acid encoding the one or more heterologous enzymes, such as from a biosynthetic pathway, for synthesizing the substrate.

In some embodiments, the invention allows novel modification on a natural product scaffold such as terpenes, polyketide synthase (PKS), nonribosomal peptide-synthetase (NRPS), and the like. As such this provides a route for a massive range of new natural products as well as commodity chemicals.

Many molecules comprise complicated chemical structures. It is a challenge to synthesize them by chemical methods or biological methods alone. The present invention enables natural biological reactions to be combined with abiological reactions to produce products previous inaccessible to natural biosynthesis.

In some embodiments, the engineered P450 apo-protein comprises an amino acid sequence that is at least 70%, 80%, 90%, 95%, or 99% identical to the amino acid sequence of SEQ ID NO: 1, except for the amino acid residues important for binding the artificial cofactor.

The amino acid sequence of *Sulfolobus acidocaldarius* (strain ATCC 33909) cytochrome P450 119 (encoded by the cyp119 gene) is as follows:

```
                                                            (SEQ ID NO: 1)
                10          20          30          40          50

MYDWFSEMRK  KDPVYYDGNI  WQVFSYRYTK  EVLNNFSKFS  SDLTGYHERL 60          70          80          90          100

EDLRNGKIRF  DIPTRYTMLT  SDPPLHDELR  SMSADIFSPQ  KLQTLETFIR 110         120         130         140         150

ETTRSLLDSI  DPREDDIVKK  LAVPLPIIVI  SKILGLPIED  KEKFKEWSDL 160         170         180         190         200

VAFRLGKPGE  IFELGKKYLE  LIGYVKDHLN  SGTEVVSRVV  NSNLSDIEKL 210         220         230         240         250

GYIILLLIAG  NETTTNLISN  SVIDFTRENL  WQRIREENLY  LKAIEEALRY 260         270         280         290         300

SPPVMRTVRK  TKERVKLGDQ  TIEEGEYVRV  WIASANRDEE  VFHDGEKFIP 310         320         330         340         350

DRNPNPHLSF  GSGIHLCLGA  PLARLEARIA  IEEFSKRFRH  IEILDTEKVP

360
        NEVLNGYKRL  VVRLKSNE
```

In some embodiments, the engineered P450 apo-protein comprises an amino acid sequence comprising H76, R80, T257, R259, and/or H315, which are residues important for binding heme. In some embodiments, the engineered P450 apo-protein comprises an amino acid sequence that is substituted for C317, T213, V254L, and/or L155W, which are residues important for binding the artificial cofactor, such that the engineered P450 apo-protein is capable of binding the artificial cofactor. In some embodiments, the engineered P450 apo-protein comprises an amino acid sequence that comprises C317G, T213G, V254L, and/or L155W, which are residues important for binding the Ir(Me)MPIX artificial cofactor, such that the engineered P450 apo-protein is capable of binding the Ir(Me)MPIX artificial cofactor.

In some embodiments, the heterologous heme transport transmembrane protein, or homologue thereof, comprises an amino acid sequence that is at least 70%, 80%, 90%, 95%, or 99% identical to the amino acid sequence of SEQ ID NO:2.

The amino acid sequence of E. coli hemin TonB-dependent receptor (encoded by the ChuA gene) is as follows:

In some embodiments, the heterologous heme transport transmembrane protein comprises a polar region at positions 250-268.

In some embodiments, the host cell comprises one or more nucleic acid encoding the P450 enzyme and/or heterologous heme transport transmembrane protein, or homologue thereof, each operatively linked to a promoter capable of expressing the polypeptide in the host cell. In some embodiments, the open reading frame of the P450 enzyme and/or heterologous heme transport transmembrane protein, or homologue thereof, are codon optimized to the host cell. In some embodiments, the nucleic acid is a vector or replicon that can stably reside in the host cell. In some embodiments, the nucleic acid is stably integrated into one or more chromosomes of the host cell.

In some embodiments, the providing step (a) comprises introducing a nucleic acid encoding the P450 enzyme and/or heterologous heme transport transmembrane protein, or homologue thereof, operatively linked to a promoter capable of expressing the P450 enzyme and/or heterologous heme

```
                                                       (SEQ ID NO: 2)
           10         20         30         40         50

MSRPQFTSLR LSLLALAVSA TLPTFAFATE TMTVTATGNA RSSFEAPMMV 60         70         80         90        100

SVIDTSAPEN QTATSATDLL RHVPGITLDG TGRINGQDVN MRGYDHRGVL 110        120        130        140        150

VLVDGVRQGT DTGHLNGTFL DPALIKRVEI VRGPSALLYG SGALGGVISY 160        170        180        190        200

DTVDAKDLLQ EGQSSGFRVF GTGGTGDHSL GLGASAFGRT ENLDGIVAWS 210        220        230        240        250

SRDRGDLRQS NGETAPNDES INNMLAKGTW QIDSAQSLSG LVRYYNNDAR 260        270        280        290        300

EPKNPQTVEA SDSSNPMVDR STIQRDAQLS YKLAPQGNDW LNADAKIYWS 310        320        330        340        350

EVRINAQNTG SSGEYREQIT KGARLENRST LFADSFASHL LTYGGEYYRQ 360        370        380        390        400

EQHPGGATTG FPQAKIDESS GWLQDEITLR DLPITLLGGT RYDSYRGSSD 410        420        430        440        450

GYKDVDADKW SSRAGMTINP TNWLMLFGSY AQAFRAPTMG EMYNDSKHFS 460        470        480        490        500

IGRFYTNYWV PNPNLRPETN ETQEYGFGLR FDDLMLSNDA LEFKASYFDT 510        520        530        540        550

KAKDYISTTV DFAAATTMSY NVPNAKIWGW DVMTKYTTDL FSLDVAYNRT 560        570        580        590        600

RGKDTDTGEY ISSINPDTVT STLNIPIAHS GFSVGWVGTF ADRSTHISSS 610        620        630        640        650

YSKQPGYGVN DFYVSYQGQQ ALKGVTTTLV LGNAFDKEYW SPQGIPQDGR

660
NGKIFVSYQW
``` transport transmembrane protein, or homologue thereof, in the host cell into the host cell.

The genetically modified host cell can be any microbe capable of production of the unnatural compound or terpenoid in accordance with the methods of the invention.

In some embodiments, the host cell is a yeast. Yeast host cells suitable for the invention include, but are not limited to, *Yarrowia, Candida, Bebaromyces, Saccharomyces, Schizosaccharomyces* and *Pichia* cells. In one embodiment, *Saccharomyces cerevisae* is the host cell. In one embodiment, the yeast host cell is a species of *Candida*, including but not limited to *C. tropicalis, C. maltosa, C. apicola, C. paratropicalis, C. albicans, C. cloacae, C. guillermondii, C. intermedia, C. lipolytica, C. panapsilosis* and *C. zeylenoides*. In one embodiment, *Candida tropicalis* is the host cell. In some embodiments, the yeast host cell is a non-oleaginous yeast. In some embodiments, the non-oleaginous yeast is a *Saccharomyces* species. In some embodiments, the *Saccharomyces* species is *Saccharomyces cerevisiae*. In some embodiments, the yeast host cell is an oleaginous yeast. In some embodiments, the oleaginous yeast is a *Rhodosporidium* species. In some embodiments, the *Rhodospondium* species is *Rhodosporidium toruloides*.

In some embodiments the host cell is a bacteria. Bacterial host cells suitable for the invention include, but are not limited to, *Escherichia, Corynebacterium, Pseudomonas, Streptomyces*, and *Bacillus*. In some embodiments, the *Escherichia* cell is an *E. coli, E. albertii, E. fergusonii, E. hermanii, E. marmotae*, or *E. vulneris*. In some embodiments, the *Corynebacterium* cell is *Corynebacterium glutamicum, Corynebacterium kroppenstedtii, Corynebacterium alimapuense, Corynebacterium amycolatum, Corynebacterium diphtheriae, Corynebacterium efficiens, Corynebacterium jeikeium, Corynebacterium macginleyi, Corynebacterium matruchotii, Corynebacterium minutissimum, Corynebacterium renale, Corynebacterium striatum, Corynebacterium ulcerans, Corynebacterium urealyticum*, or *Corynebacterium uropygiale*. In some embodiments, the *Pseudomonas* cell is a *P. putida, P. aeruginosa, P. chlororaphis, P. fluorescens, P. pertucinogena, P. stutzeri, P. syringae, P. cremoricolorata, P. entomophila, P. fulva, P. monteilii, P. mosselii, P. oryzihabitans, P. parafluva*, or *P. plecoglossicida*. In some embodiments, the *Streptomyces* cell is a *S. coelicolor, S. lividans, S. venezuelae, S. ambofaciens, S. avermitilis, S. albus*, or *S. scabies*. In some embodiments, the *Bacillus* cell is *B. subtilis, B. megaterium, B. licheniformis, B. anthracis, B. amyloliquefaciens*, or *B. pumilus*.

One can modify the expression of a gene encoding the P450 enzyme taught herein by a variety of methods in accordance with the methods of the invention. Those skilled in the art would recognize that increasing gene copy number, ribosome binding site strength, promoter strength, and various transcriptional regulators can be employed to alter an enzyme expression level. The present invention provides a method of producing an unnatural compound or terpenoid in a genetically modified host cell that is modified to express a P450 enzyme capable of using the artificial cofactor.

In other embodiments, the host cells are modified, or not modified, to secrete the unnatural compound or terpenoid into the growth medium. In other embodiments, the host cells are modified, or not modified, to accumulate the unnatural compound or terpenoid in the host cell. In these embodiments, the alkyl lactone is separated from the host cell by any suitable means, such as centrifugation or settling of the cell material, cell lysis, and subsequent purification of the unnatural compound or terpenoid.

In some embodiments, the nucleic acid are recombinant DNA vectors.

References cited herein:

1 Cravens, A., Payne, J. & Smolke, C. D. Synthetic biology strategies for microbial biosynthesis of plant natural products. *Nat. Commun.* 10, 2142 (2019).

2 Schwizer, F. et al. Artificial Metalloenzymes: Reaction Scope and Optimization Strategies. *Chem. Rev.* 118, 142-231 (2018).

3 Gu, Y., Natoli, S. N., Liu, Z., Clark, D. S. & Hartwig, J. F. Site-Selective Functionalization of (sp3)C—H Bonds Catalyzed by Artificial Metalloenzymes Containing an Iridium-Porphyrin Cofactor. *Angew. Chem. Int. Ed.* 58, 13954-13960 (2019).

4 Key, H. M. et al. Beyond Iron: Iridium-Containing P450 Enzymes for Selective Cyclo-propanations of Structurally Diverse Alkenes. *ACS Cent. Sci.* 3, 302-308 (2017).

5 Dydio, P., Key, H. M., Hayashi, H., Clark, D. S. & Hartwig, J. F. Chemoselective, Enzymatic C—H Bond Amination Catalyzed by a Cytochrome P450 Containing an Ir(Me)-PIX Cofactor. *J. Am. Chem. Soc.* 139, 1750-1753 (2017).

6 Chatterjee, A. et al. An Enantioselective Artificial Suzukiase Based on the Biotin-Streptavidin Technology. *Chem. Set.* 7, 673 (2016).

7 Abe, S. et al. Control of the Coordination Structure of Organometallic Palladium Complexes in an apo-Ferritin Cage. *J. Am. Chem. Soc.* 130, 10512-10514 (2008).

8 Letondor, C. et al. Artificial Transfer Hydrogenases Based on the Biotin-(Strept)Avidin Technology: Fine Tuning the Selectivity by Saturation Mutagenesis of the Host Protein. *J. Am. Chem. Soc.* 128, 8320 (2006).

9 Skander, M. et al. Artificial Metalloenzymes: (Strept) Avidin as Host for Enantioselective Hydrogenation by Achiral Biotinylated Rhodium-Diphosphine Complexes. *J. Am. Chem. Soc.* 126, 14411 (2004).

10 Lin, C. C., Lin, C. W. & Chan, A. S. C. Catalytic Hydrogenation of Itaconic Acid in a Biotinylated Pyrphos-Rhodium(I) System in a Protein Cavity. *Tetrahedron; Asymmetry* 10, 1887 (1999).

11 Philippart, F. et al. A Hybrid Ring-Opening Metathesis Polymerization Catalyst Based on an Engineered Variant of the Beta-Barrel Protein Fhua. *Chem.-Eur. J.* 19, 13865 (2013).

12 Lo, C., Ringenberg, M. R., Gnandt, D., Wilson, Y. & Ward, T. R. Artificial Metalloenzymes for Olefin Metathesis Based on the Biotin-(Strept)Avidin Technology. *Chem. Commun.* 47, 12065 (2011).

13 Jeschek, M. et al. Directed evolution of artificial metalloenzymes for in vivo metathesis. *Nature* 537, 661-665 (2016).

14 Zhao, J. et al. Genetic Engineering of an Artificial Metalloenzyme for Transfer Hydrogenation of a Self-Immolative Substrate in *Escherichia coli*'s Periplasm. *J. Am. Chem. Soc.* 140, 13171-13175 (2018).

15 Grimm, A. R. et al. A Whole Cell *E. coli* Display Platform for Artificial Metalloenzymes: Poly(phenylacetylene) Production with a Rhodium-Nitrobindin Metalloprotein. *ACS Catal.* 8, 2611-2614 (2018).

16 Heinisch, T. et al. *E. coli* surface display of streptavidin for directed evolution of an allylic deallylase. *Chem. Set.* 9, 5383-5388 (2018).

17 Khanna, N., Esmieu, C., Meszaros, L. S., Lindblad, P. & Berggren, G. In vivo activation of an [FeFe] hydrogenase using synthetic cofactors. *Energy Environ. Sci.* 10, 1563-1567 (2017).

18 Song, W. J. & Tezcan, F. A. A designed supramolecular protein assembly with in vivo enzymatic activity. *Science* 346, 1525 (2014).

19 Huang, W. & Wilks, A. Extracellular Heme Uptake and the Challenge of Bacterial Cell Membranes. *Annu. Rev. Biochem* 86, 799-823 (2017).

20 Brahmkshatriya, P. P. & Brahmkshatriya, P. S. in *Natural Products; Phytochemistry, Botany and Metabolism of Alkaloids, Phenolics and Terpenes* (eds Kishan Gopal Ramawat & Jean-Michel Merillon) 2665-2691 (Springer Berlin Heidelberg, 2013).

21 Helfrich, E. J. N., Lin, G.-M., Voigt, C. A. & Clardy, J. Bacterial terpene biosynthesis: challenges and opportunities for pathway engineering. *Beilstein J. Org. Chem.* 15, 2889-2906 (2019).

22 Coelho, P. S., Brustad, E. M., Kannan, A. & Arnold, F. H. Olefin Cyclopropanation via Carbene Transfer Catalyzed by Engineered Cytochrome P450 Enzymes. *Science* 339, 307-310(2013).

23 Key, H. M., Dydio, P., Clark, D. S. & Hartwig, J. F. Abiological Catalysis by Artificial Haem Proteins Containing Noble Metals in Place of Iron. *Nature* 534, 534 (2016).

24 Dydio, P. et al. An Artificial Metalloenzyme with the Kinetics of Native Enzymes. *Science* 354, 102 (2016).

25 Jeschek, M., Panke, S. & Ward, T. R. Artificial Metalloenzymes on the Verge of New-to-Nature Metabolism. *Trends Biotechnol.* 36, 60-72 (2018).

26 Lelyveld, V. S., Brustad, E., Arnold, F. H. & Jasanoff, A. Metal-Substituted Protein MRI Contrast Agents Engineered for Enhanced Relaxivity and Ligand Sensitivity. *J. Am. Chem. Soc.* 133, 649-651 (2011).

27 Bordeaux, M., Singh, R. & Fasan, R. Intramolecular C(sp3)H amination of arylsulfonyl azides with engineered and artificial myoglobin-based catalysts. *Biorg. Med. Chem.* 22, 5697-5704 (2014).

28 Reynolds, E. W., Schwochert, T. D., McHenry, M. W., Watters, J. W. & Brustad, E. M. Orthogonal Expression of an Artificial Metalloenzyme for Abiotic Catalysis. *ChemBioChem* 18, 2380-2384 (2017).

29 Alonso-Gutierrez, J. et al. Metabolic engineering of *Escherichia coli* for limonene and perillyl alcohol production. *Metab. Eng.* 19, 33-41 (2013).

30 Ascue Avalos, G. A., Toogood, H. S., Tait, S., Messiha, H. L. & Scrutton, N. S. From Bugs to Bioplastics: Total (+)-Dihydrocarvide Biosynthesis by Engineered *Escherichia coli*. *ChemBioChem* 20, 785-792 (2019).

31 Henderson, D. P., Wyckoff, E. E., Rashidi, C. E., Verlei, H. & Oldham, A. L. Characterization of the *Plesiomonas shigelloides* Genes Encoding the Heme Iron Utilization System. *J. Bacteriol.* 183, 2715-2723 (2001).

32 Smith, B. J. Z., Gutierrez, P., Guerrero, E., Brewer, C. J. & Henderson, D. P. Development of a Method To Produce Hemoglobin in a Bioreactor Culture of *Escherichia coli* BL21(DE3) Transformed with a Plasmid Containing *Plesiomonas shigelloides* Heme Transport Genes and Modified Human Hemoglobin Genes. *Appl. Environ. Microbiol.* 77, 6703 (2011).

33 Carter, O. A., Peters, R. J. & Croteau, R. Monoterpene biosynthesis pathway construction in *Escherichia coli*. *Phytochemistry* 64, 425-433 (2003).

34 Waldman, A. J. & Balskus, E. P. Discovery of a Diazo-Forming Enzyme in Cremeomycin Biosynthesis. *J. Org. Chem.* 83, 7539-7546 (2018).

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Artificial Biosynthetic Pathway with an Iridium-Containing P450 for an Unnatural Terpenoid Synthetic biology enables microbial hosts to produce complex molecules that are otherwise produced by organisms that are rare or difficult to cultivate, but the structures of these molecules are limited to those formed by chemical reactions catalyzed by natural enzymes[1]. The integration of artificial metalloenzymes (ArMs) that catalyze unnatural reactions[2] into metabolic networks could broaden the cache of molecules produced biosynthetically by microorganisms. We report an engineered microbial cell expressing a heterologous biosynthetic pathway, which contains both natural enzymes and ArMs, that produces an unnatural product with high diastereoselectivity. To create this hybrid biosynthetic organism, we engineered *Escherichia coli* (*E. coli*) with a heterologous terpene biosynthetic pathway and an ArM containing an iridium-porphyrin complex that was transported into the cell with a heterologous transport system. We improved the diastereoselectivity and product titer of the unnatural product by evolving the ArM and selecting the appropriate gene induction and cultivation conditions. This work shows that synthetic biology and synthetic chemistry can produce, together with natural and artificial enzymes in whole cells, molecules that were previously inaccessible to nature.

This example describes the combination of limonene biosynthesis by a series of heterologously expressed natural enzymes and the catalysis by an artificial metalloenzyme Ir-CYP119 (CYP119 containing Ir(Me)MPIX as cofactor; CYP119, a P450 enzyme from *Sulfolobus solfataricus*; MPIX, mesoporphyrin IX) to produce a terpenoid that was previously inaccessible in a microbial host. This unnatural combination of synthetic biology and synthetic chemistry mimics the production of a terpene and subsequent conversion of this hydrocarbon to a terpenoid by P450 enzymes during natural biosynthesis.

Our overall strategy for production of the unnatural terpenoid is depicted in FIG. 1. The artificial metalloenzyme is assembled in *E. coli* with the aid of a cofactor transport system and overexpression of the apo-enzyme. In concert, the same *E. coli* is engineered with the pathway for production of a natural product that serves as the substrate for the artificial metalloenzyme. This combination of natural and unnatural reactions in the same cell would produce an unnatural derivative of a classic natural product.

Results and Discussion

Assembling the ArM in vivo. The first major challenge facing this integration of an artificial metalloenzyme with a cellular biosynthetic process is to assemble such enzymes in the cytoplasm[25]. Previously, we reported the in vitro construction of Ir-CYP119 by incorporation of Ir(Me)MPIX into the heme binding site of the purified apo-form of CYP119. To construct this artificial enzyme in a cell, the cofactor must enter into the cytoplasm from the medium through the cell membranes. Metal-substituted heme derivatives have been reported to be transported across cell membranes when the outer-membrane receptor ChuA is overexpressed[26-28]. Thus, we first considered whether the co-expression of such a heme transporter and CYP119 would enable the artificial cofactor Ir(Me)MPIX to be transported into $E.$ $coli$ and incorporated into the apo-CYP119 mutant in the cytoplasm.

To test the feasibility of assembling Ir-CYP119 and catalyzing a reaction in $E.$ $coli$, we studied the cyclopropanation of the monoterpenoid (−)-carvone. We used the diastereoselectivity of the reaction as a parameter to distinguish any background reaction or reaction catalyzed by free cofactor from the reaction catalyzed by the assembled artificial metalloenzyme. During our previous study, Ir-CYP119 generated from in vitro reconstitution of Ir(Me)MPIX and purified apo-CYP119 mutants catalyzed the cyclopropanation of (−)-carvone with EDA (ethyl diazoacetate) to give an 8:1:1:1 ratio of diastereomeric products. The major diastereomer of this reaction is a minor diastereomer of the 1:1:3:3 ratio of diastereomers formed from the analogous reaction catalyzed by the free iridium porphyrin complex[4]. Thus, a reaction that forms a mixture of diastereomers resembling the ratio produced by the pure ArM in vitro would denote reaction by the assembled ArM in the cell.

Figure 5A:
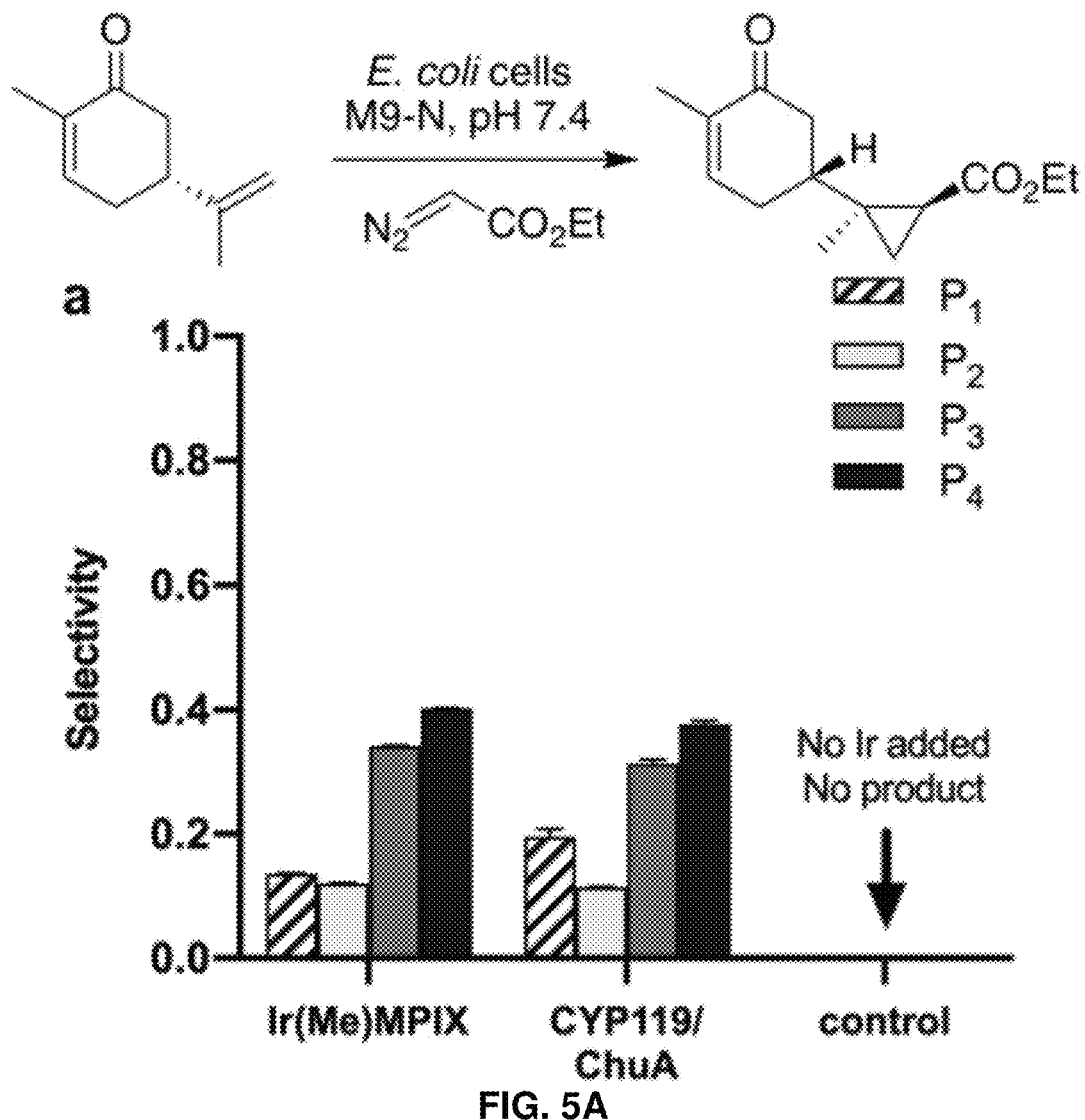
FIG. 5A. The cyclopropanation of carvone catalyzed by whole cells, a, The diastereoselectivity of the cyclopropanation of (−)-carvone catalyzed by E. coli cells harboring Ir-CYP119 was similar to that of the reaction catalyzed by the free cofactor Ir(Me)MPIX when 10 μM Ir(Me)MPIX was added to cell culture. Left: reaction catalyzed by Ir(Me)MPIX; Middle: reaction catalyzed by E. coli transformed with pCYP119-141 (coding for CYP119 mutant) and pJHA147 (coding for ChuA). Protein expression was induced with 0.5 mM IPTG, and 10 μM Ir(Me)MPIX was added upon induction; Right: reaction catalyzed by E. coli cells cultivated in the absence of Ir(Me)MPIX. From left to right, reactions were catalyzed by E. coli cells transformed with 1) pCYP119-141 and pJHA147 2) pJHA147 3) pBbE7A (coding for RFP, red fluorescent protein). Protein expression was induced with 0.5 mM IPTG and 0.1 μM Ir(Me)MPIX was added concurrently. Reaction conditions: 4 mM (−)-carvone, 20 mM EDA, 1% ethanol, 350 μL M9-N buffer. $P_1$-$P_4$ are the four diastereomeric products numbered in the order of elution by GC. All data from whole-cell reactions are shown as the average from three biological replicates, with error bars indicating 1 standard deviation.

To this end, $E.$ $coli$ BL21(DE3) cells co-expressing the heme transporter ChuA and the CYP119 mutant were supplemented with 10 μM Ir(Me)MPIX, and the cell pellets containing in vivo-assembled Ir-CYP119 were directly employed for catalyzing the reaction of (−)-carvone with EDA after re-suspension in reaction buffer. However, the diastereomeric ratio (dr) of the whole-cell reaction was 1.7:1.0:2.7:3.3 (FIG. 5A), indicating that the majority of the product of the whole-cell system was formed from a reaction catalyzed by the free iridium porphyrin complex, rather than by an assembled ArM. In addition, no product was detected when $E.$ $coli$ cultures were incubated in the absence of Ir(Me)MPIX (FIG. 5A).

Figure 2A:
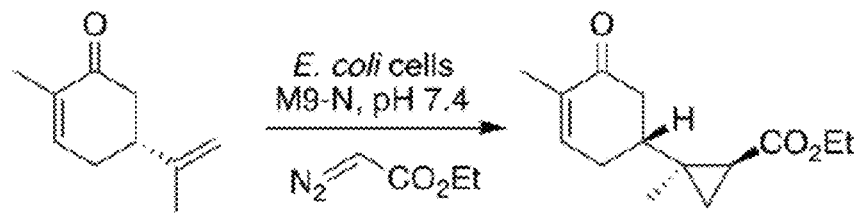
FIG. 2A. The whole cells containing Ir-CYP119 catalyze the cyclopropanation of (−)-carvone with high diastereoselectivity. Decreasing the concentration of Ir(Me)MPIX increased the diastereoselectivity of whole-cell reactions. The identity of the major diastereomer has been reported previously[4], the conformations of minor diastereomers are not known. Control strain: E. coli co-expressing RFP and CYP119 (with lacUV5 promoter). $P_1$-$P_4$ are the four diastereomeric products numbered in the order of elution by GC (gas chromatography). Selectivity in the plots corresponds to the ratio of each diastereomer versus the total of the four diastereomeric products. All data are shown as the average from three biological replicates, with error bars indicating 1 standard deviation.
Figure 2A:
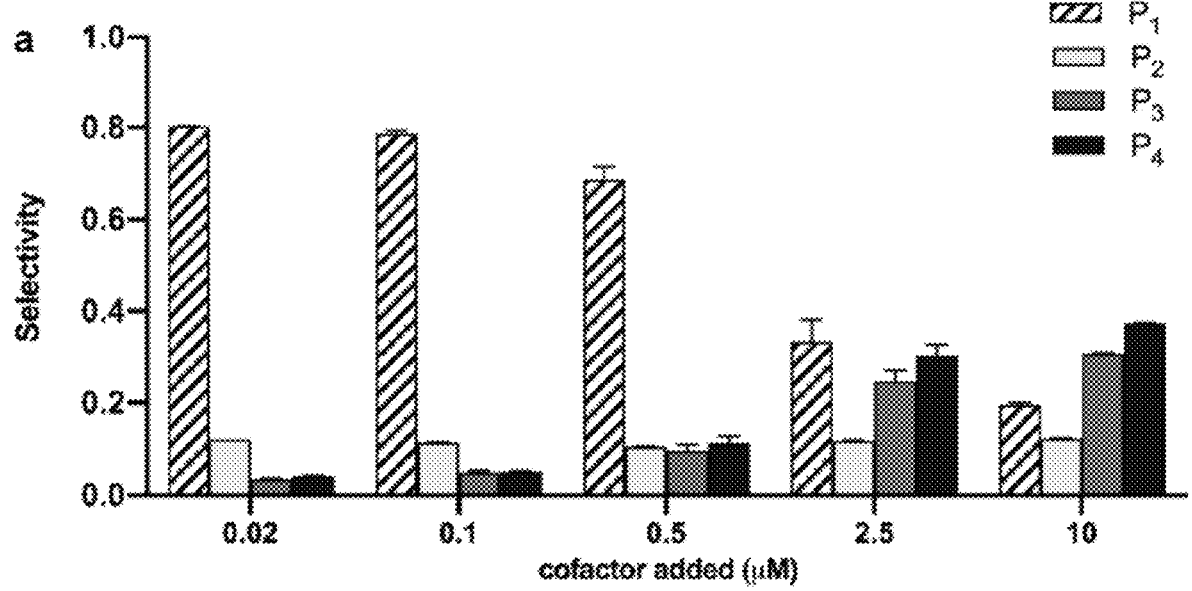
Figure 5B:
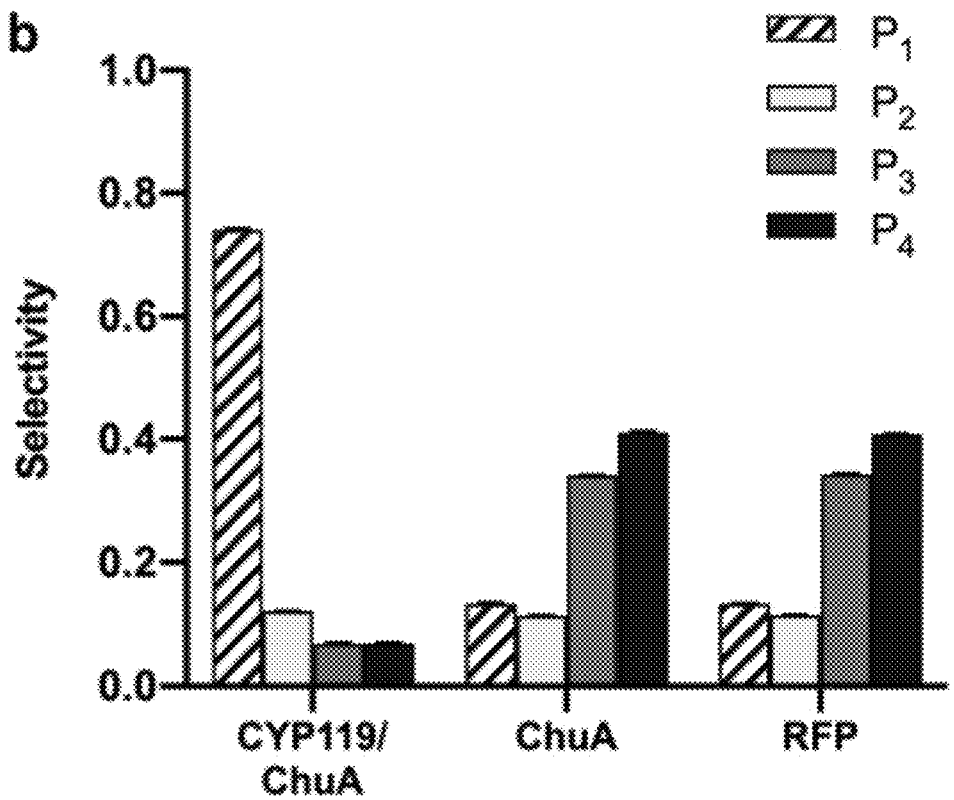
FIG. 5B. The cyclopropanation of carvone catalyzed by whole cells. The expression of CYP119 is required for the high diastereoselectivity of the cyclopropanation of (−)-carvone catalyzed by E. coli cells. From left to right, reactions were catalyzed by E. coli cells transformed with 1) pCYP119-141 and pJHA147 2) pJHA147 3) pBbE7A (coding for RFP, red fluorescent protein). Protein expression was induced with 0.5 mM IPTG and 0.1 μM Ir(Me)MPIX was added concurrently. Reaction conditions: 4 mM (−)-carvone, 20 mM EDA, 1% ethanol, 350 μL M9-N buffer. $P_1$-$P_4$ are the four diastereomeric products numbered in the order of elution by GC. All data from whole-cell reactions are shown as the average from three biological replicates, with error bars indicating 1 standard deviation.

To reduce interference from the background reactivity of the free iridium porphyrin, we evaluated the reaction of (−)-carvone with EDA catalyzed by cells grown in the presence of Ir(Me)MPIX in concentrations ranging from 10 μM to 0.02 μM. These experiments showed that the dr of the cyclopropane product was much higher (23:3.5:1.0:1.2) when the concentration of Ir(Me)MPIX was 0.02 μM (FIG. 2A). We surmised that the lower concentrations of Ir(Me)MPIX reduced the amount of product formed by a background reaction catalyzed by the cofactor unbound to CYP119. Control experiments showed that the dr was low for products formed in $E.$ $coli$ expressing ChuA without co-expression of CYP119 (FIG. 5B). Under the conditions of this control experiment, the cyclopropanation would be catalyzed by the free iridium cofactor.

Next, we sought to combine the Ir-CYP119 with a natural biosynthetic pathway to produce an unnatural terpenoid. The analysis of Ir(Me)MPIX uptake for cyclopropanation in whole cells described above was conducted with carvone because we had shown previously that cyclopropanation of this terpenoid occurred in high yield and high diastereoselectivity[4]. However, the biosynthesis of (−)-limonene, which has the same carbon skeleton as (−)-carvone, occurs with much higher titer[29,30], so we sought to assess the potential to combine heterologous biosynthesis with artificial metalloenzymes by generating unnatural derivatives of limonene.

Figure 6A:
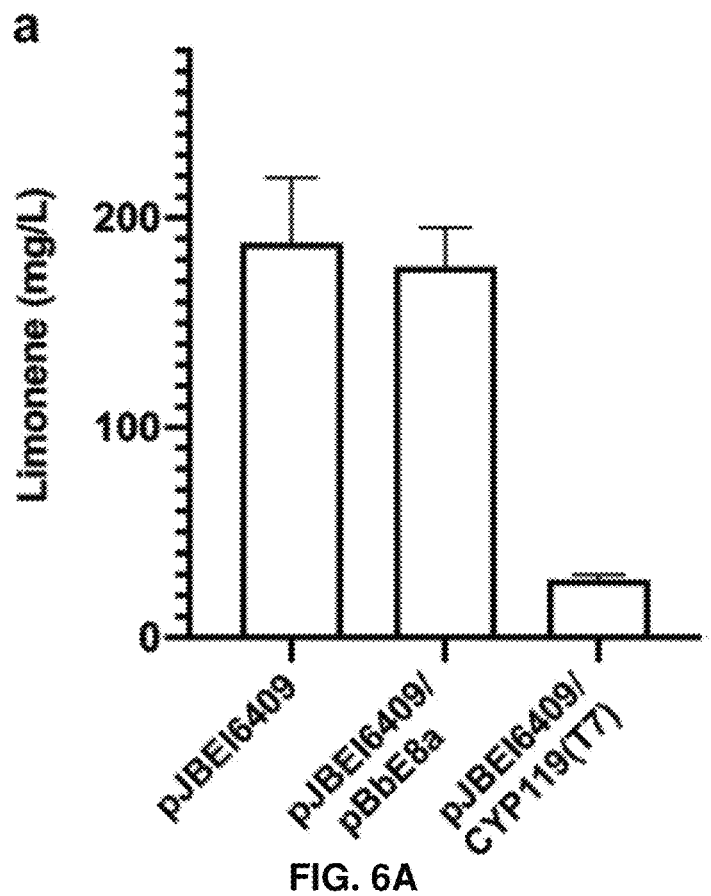
FIG. 6A. The effect of CYP119 co-expression and Ir(Me)MPIX addition on limonene titer. High-level expression of CYP119 decreased the limonene titer sharply. From left to right, limonene was produced from E. coli cells expressing 1) pJBEI6409 (plasmid encoding limonene biosynthetic pathway) 2) pJBEI6409 and pBbE8a (empty vector) 3) pJBEI6409 and pCYP119-141 with T7 promoter. Limonene production was induced with 0.5 mM IPTG and 10% (v/v) dodecane was added to trap limonene. After 24 h, limonene titer was determined by GC-MS. All data are shown as the average from three biological replicates, with error bars indicating 1 standard deviation.
Figure 7:
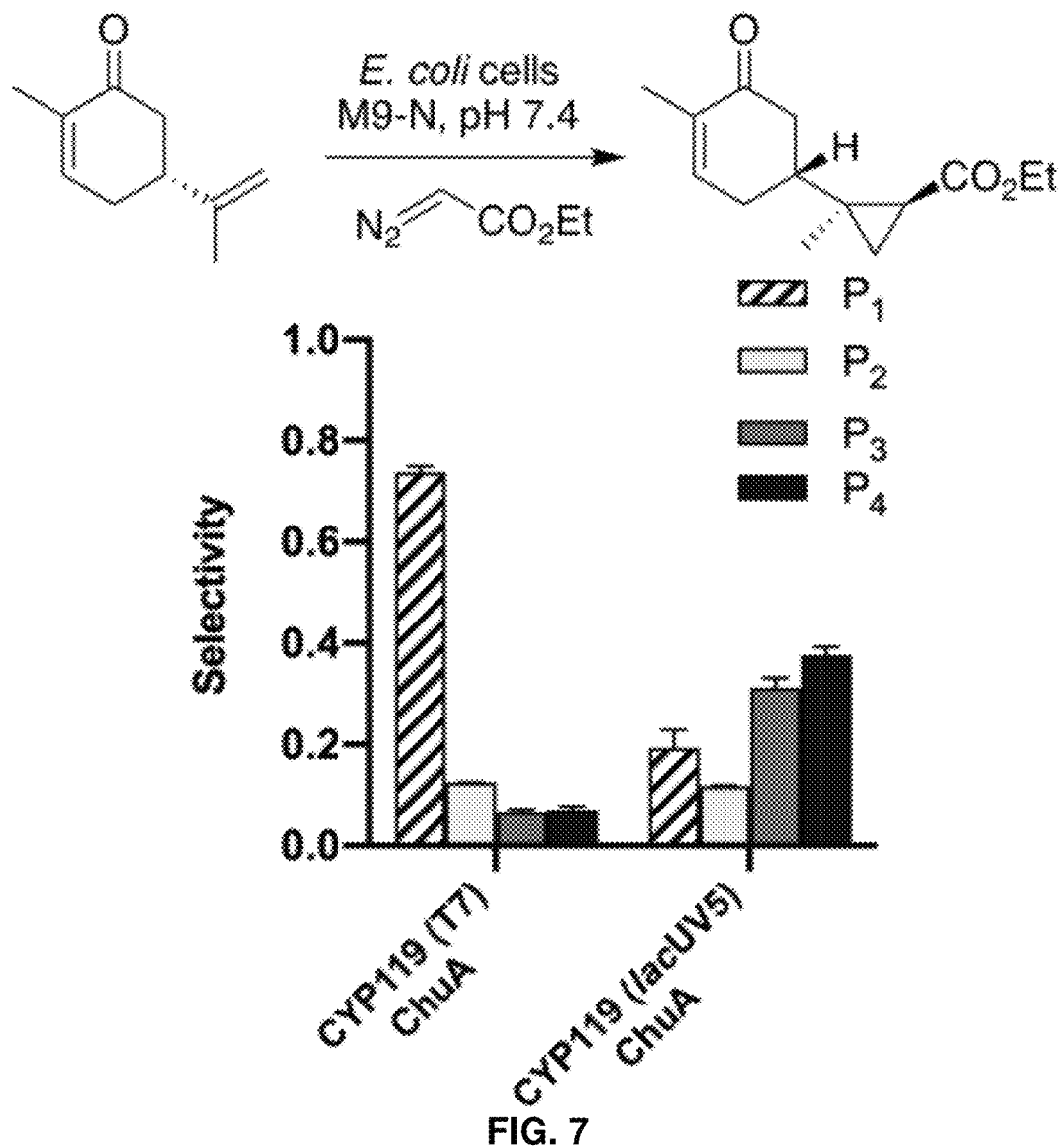
FIG. 7. High-level expression of CYP119 was essential for obtaining high diastereoselectivity for the whole-cell reaction when using ChuA as a transporter. From left to right, reactions were catalyzed by E. coli cells transformed with 1) pJHA147 (encoding ChuA) and pCYP119-141 (encoding CYP119 with T7 promoter) and 2) pJHA147 and pJHA029 (encoding CYP119 with lacUV5 promoter), respectively. All strains were induced with 0.5 mM IPTG and 0.1 μM Ir(Me)MPIX was added concurrently. Reaction conditions: 4 mM (−)-carvone, 20 mM EDA, 1% ethanol, 350 μL M9-N buffer. $P_1$-$P_4$ are the four diastereomeric products numbered in the order of elution by GC. All data are shown as the average from three biological replicates, with error bars indicating 1 standard deviation.

Initial attempts to express a heterologous biosynthetic pathway to form limonene in concert with expression of CYP119 regulated by a T7 promoter caused the titer of limonene to decrease drastically from 188 mg/L without co-expression of CYP119 to 28 mg/L with co-expression (FIG. 6A). To restore the production of limonene, we expressed CYP119 with a weaker promoter. However, when the reaction of exogenously added (−)-carvone with EDA was conducted with cells co-expressing ChuA and CYP119 with the weaker lacUV5 promoter, the cyclopropane was formed with low diastereoselectivity, again implying that assembly of the artificial metalloenzyme was inefficient (FIG. 7). Thus, we sought conditions that would assemble the artificial metalloenzyme more efficiently at low expression levels of CYP119 to generate product with high diastereoselectivity.

Figure 2B:
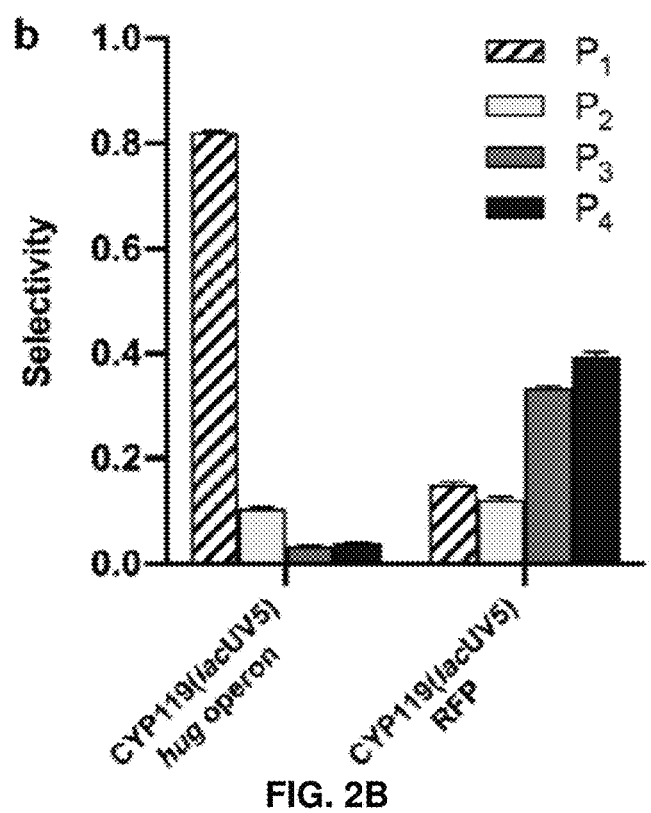
FIG. 2B. The whole cells containing Ir-CYP119 catalyze the cyclopropanation of (−)-carvone with high diastereoselectivity. E. coli cells co-expressing CYP119 (with lacUV5 promoter) and the hug operon could maintain the high diastereoselectivity under low expression level of CYP119. E. coli cells containing CYP119 (with lacVN5 promoter) and an RFP-coding plasmid are shown as control (RFP, Red Fluorescent Protein). Both strains were cultivated in the presence of 0.1 μM Ir(Me)MPIX. Control strain: E. coli co-expressing RFP and CYP119 (with lacUV5 promoter). $P_1$-$P_4$ are the four diastereomeric products numbered in the order of elution by GC (gas chromatography). Selectivity in the plots corresponds to the ratio of each diastereomer versus the total of the four diastereomeric products. All data are shown as the average from three biological replicates, with error bars indicating 1 standard deviation.

To increase the efficiency of the cellular uptake of Ir(Me)MPIX, we replaced the ChuA transporter with a heme transport system encoded by the hug operon from $Plesiomonas$ $shigelloides$, which has been used less frequently than ChuA, but has been shown previously to increase expression yields of hemoglobin to unusually high levels with heme supplementation[31,32]. Reactions of (−)-carvone with EDA catalyzed by $E.$ $coli$ cells expressing the HUG transport system, in concert with CYP119 (expressed from the lacUV5 promoter), formed the cyclopropane product with a high diastereoselectivity of 82% (the % diastereoselectivity in this case is the percentage of the major diastereomer in the 24.0:3.1:1.0:1.2 ratio of diastereomeric products) under conditions that are identical to those of the reactions with cells expressing the ChuA transporter (FIG. 2B).

Figure 2C:
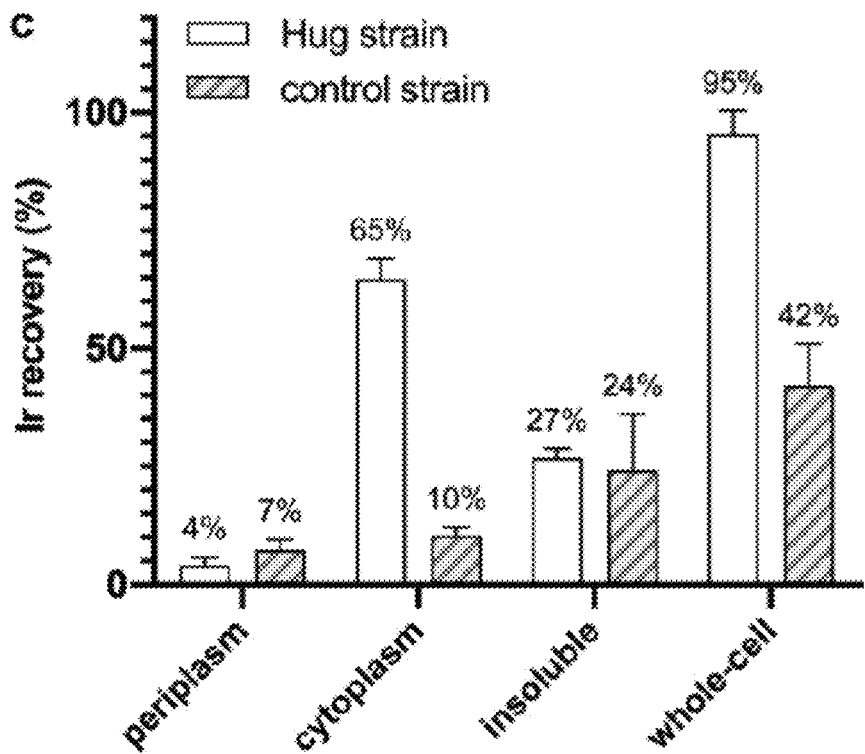
FIG. 2C. The whole cells containing Ir-CYP119 catalyze the cyclopropanation of (−)-carvone with high diastereoselectivity. The percentages of added iridium (0.1 μM) that were recovered from the subcellular fractions of E. coli cells. Hug strain: E. coli co-expressing the HUG system and CYP119 (with lacVN5 promoter). Control strain: E. coli co-expressing RFP and CYP119 (with lacUV5 promoter). $P_1$-$P_4$ are the four diastereomeric products numbered in the order of elution by GC (gas chromatography). Selectivity in the plots corresponds to the ratio of each diastereomer versus the total of the four diastereomeric products. All data are shown as the average from three biological replicates, with error bars indicating 1 standard deviation.
Figure 8:
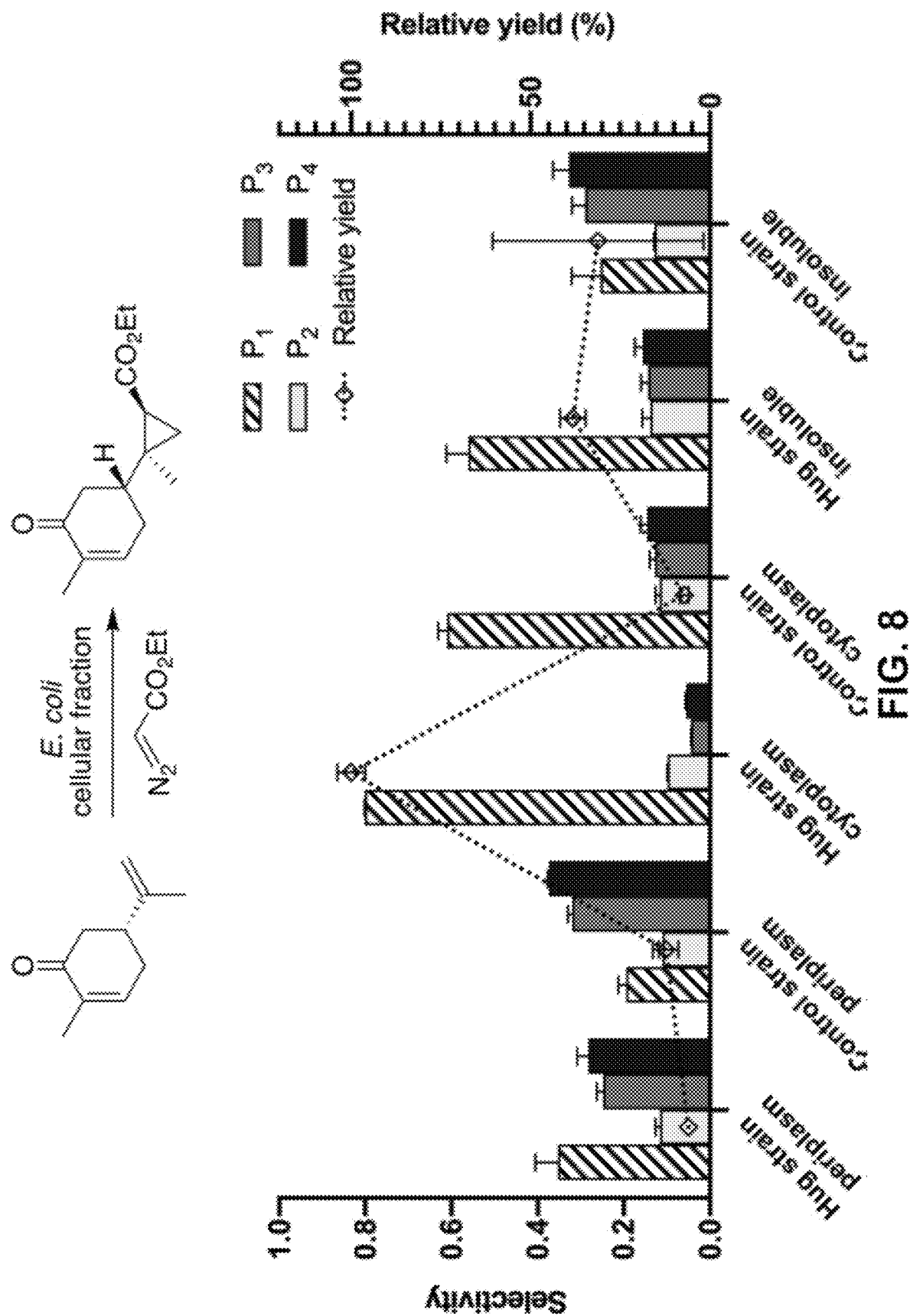
FIG. 8. The diastereoselectivity and relative yield of the cyclopropanation of (−)-carvone catalyzed by different cellular fractions isolated from E. coli cells. Hug strain: E. coli transformed with pHug21 (encoding HUG system) and pJHA110 (encoding CYP119 mutant with lacUV5 promoter); Control strain: E. coli transformed with pBbS5a (encoding RFP protein) and pJHA110. Reaction conditions: 4 mM (−)-carvone, 20 mM EDA, 1% ethanol, 500 μL cellular fraction. The relative yields of these reactions were calculated by normalizing the yield of the reaction catalyzed by the cytoplasmic fraction from Hug strain as 100%. All data are shown as the average from three biological replicates, with error bars indicating 1 standard deviation.

To elucidate the origin of the higher efficiency of the assembly of ArMs in cells expressing the HUG transport system, the distribution of iridium was analyzed by ICP-MS (inductively coupled plasma mass spectrometry) (FIG. 2C). In cells harboring CYP119 in the presence of 0.1 μM Ir(Me)MPIX, 65% of the iridium was located in the cytoplasm of the cells expressing the HUG transport system, while only 10% of the iridium was located in the cytoplasm of the cells expressing no transporter. Further, the cytoplasmic fraction isolated from the cells co-expressing the HUG transport system catalyzed the cyclopropanation of (−)-carvone with a diastereoselectivity of 80%, and the yield of cyclopropane was more than 13 times higher than that of the reaction catalyzed by the cytoplasmic fraction from cells expressing no transporter (FIG. 8). These results indicate that the HUG system significantly enhances the uptake of Ir(Me)MPIX into the cytoplasm.

Figure 3A:
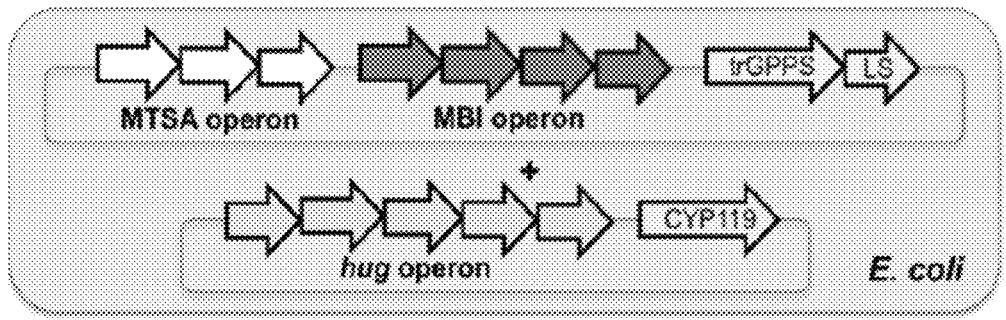
FIG. 3A. Combining limonene biosynthesis with ArM. A schematic diagram of E. coli strain that combines the limonene biosynthetic pathway and the ArM that catalyzes cyclopropanation of limonene. The string of genes at the top represents the plasmid harboring the mevalonate-based limonene biosynthetic pathway (pJBEI6410)[29]. The bottom one represents the plasmid harboring the HUG system and CYP119 mutant (pJHA135). $P_1$-$P_4$ are the four diastereomeric products numbered in the order of elution by GC. The selectivity of $P_1$-$P_4$ corresponds to the ratio of each diastereomer versus the total of the four diastereomeric products. $P_{total}$ is the sum of four diastereomeric products. All data from whole-cell reactions are shown as the average from three biological replicates, with error bars indicating 1 standard deviation.
Figure 3B:
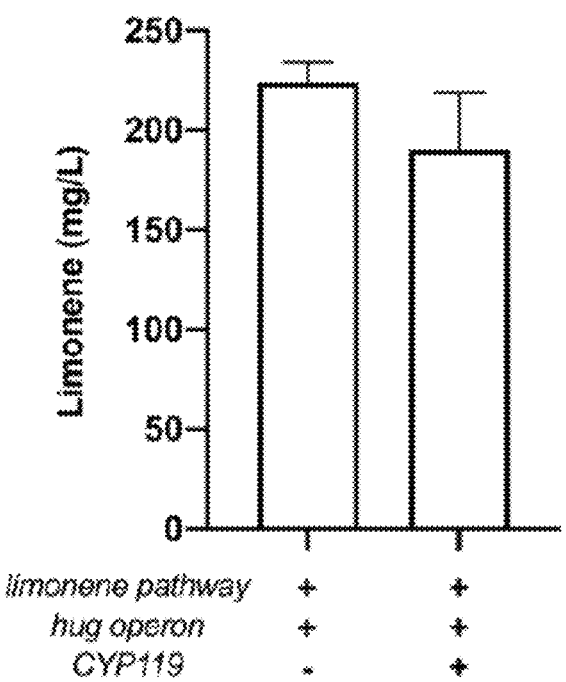
FIG. 3B. Combining limonene biosynthesis with ArM. (−)-Limonene was produced with high titer in E. coli strains expressing the limonene pathway/hug operon (pJBEI6410+pJHA047) and limonene pathway/hug operon/CYP119 (pJBEI6410+pJHA135), respectively. $P_1$-$P_4$ are the four diastereomeric products numbered in the order of elution by GC. The selectivity of $P_1$-$P_4$ corresponds to the ratio of each diastereomer versus the total of the four diastereomeric products. $P_{total}$ is the sum of four diastereomeric products. All data from whole-cell reactions are shown as the average from three biological replicates, with error bars indicating 1 standard deviation.
Figure 6B:
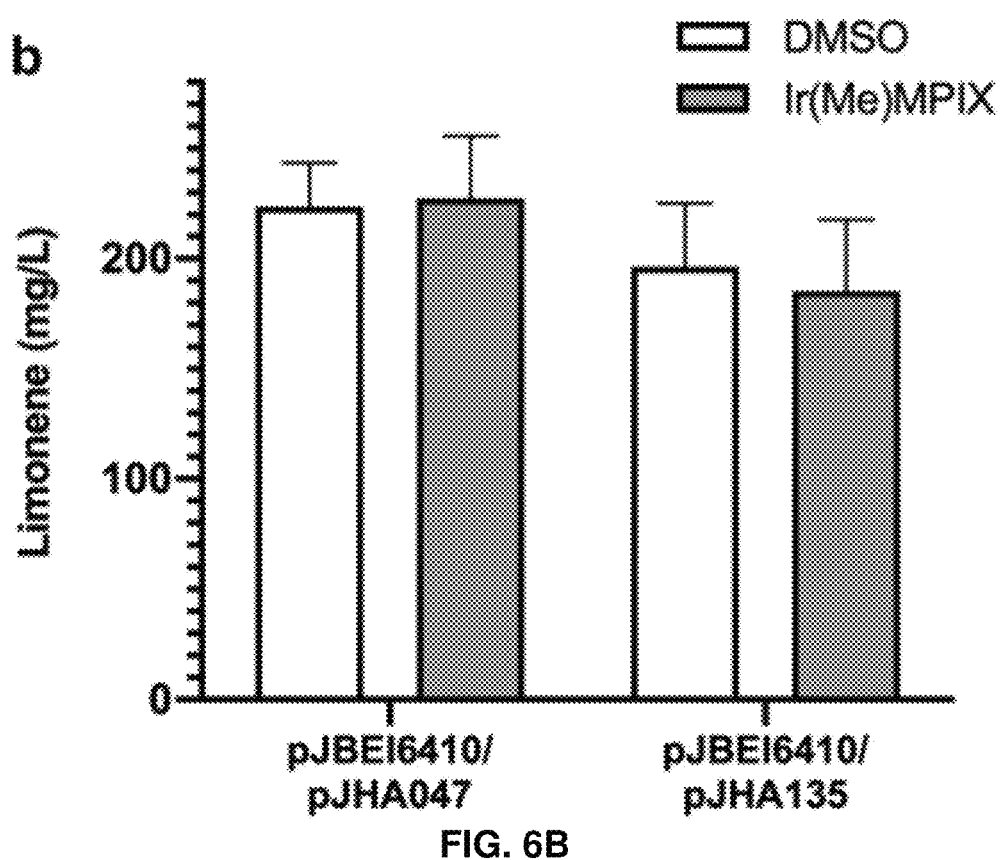
FIG. 6B. The effect of CYP119 co-expression and Ir(Me)MPIX addition on limonene titer. The addition of 0.1 μM Ir(Me)MPIX in DMSO (DMSO alone as a control) had little impact on the titers of limonene. From left to right, limonene was produced from E. coli cells co-transformed with 1) pJBEI6410 (plasmid encoding limonene biosynthetic pathway) and pJHA047 (plasmid encoding HUG system) 2) pJBEI6410 and pJHA135 (plasmid encoding both the HUG system and CYP119 mutant). Limonene production was induced with 0.5 mM IPTG and 10% (v/v) dodecane was added to trap limonene. After 24 h, limonene titer was determined by GC-MS. All data are shown as the average from three biological replicates, with error bars indicating 1 standard deviation.
Figure 9A:
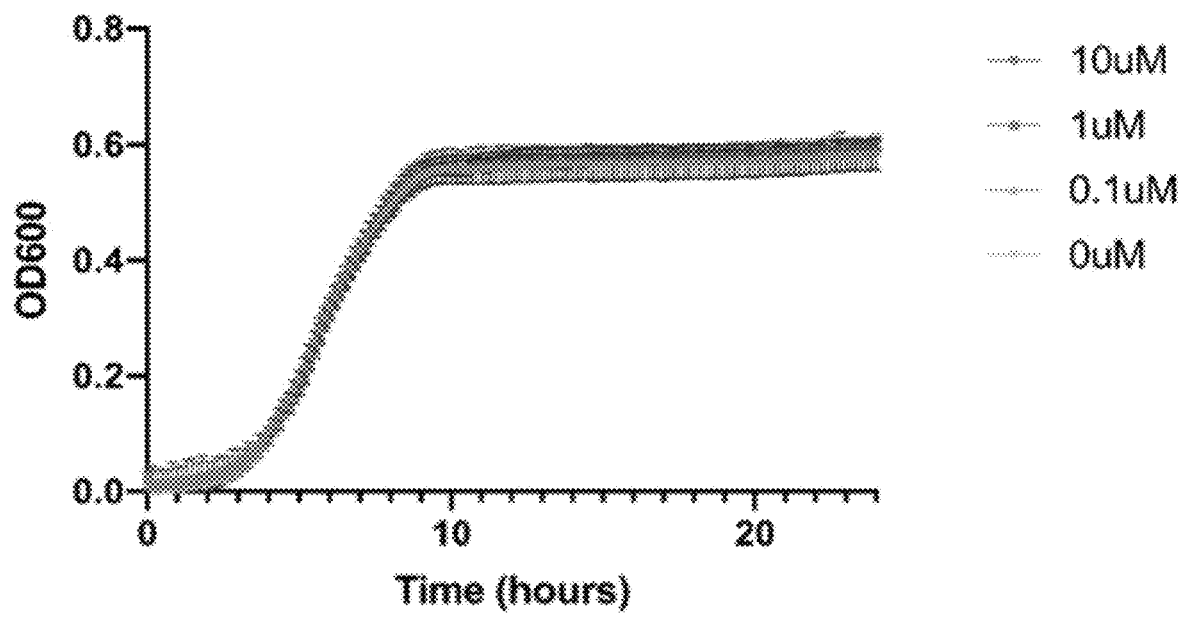
FIG. 9A. Evaluation of the effect of Ir(Me)MPIX and cyclopropyl limonene on cell growth. The addition of Ir(Me)MPIX has little effect on the growth of BL21(DE3) cells transformed with an empty vector pBbS5K under the range of concentrations tested. Error bars represent 1 standard deviation of three biological replicates.
Figure 9B:
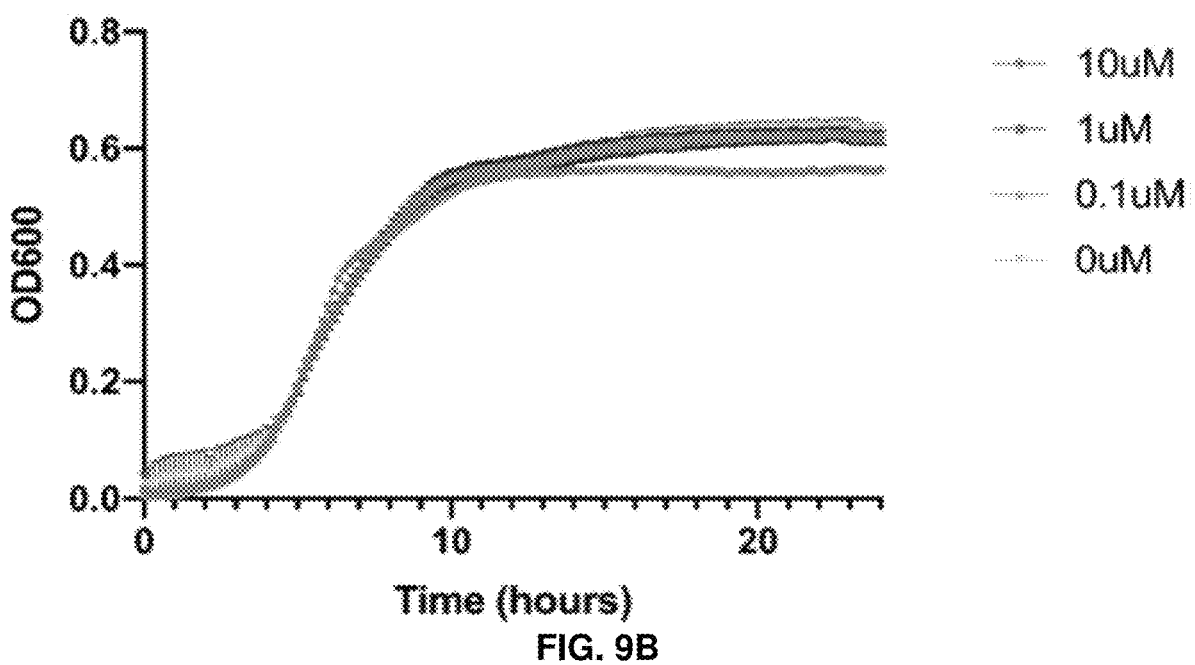
FIG. 9B. Evaluation of the effect of Ir(Me)MPIX and cyclopropyl limonene on cell growth. The addition of Ir(Me)MPIX has little effect on the growth of BL21(DE3) cells expressing the HUG system under the range of concentrations tested. Error bars represent 1 standard deviation of three biological replicates.
Figure 9C:
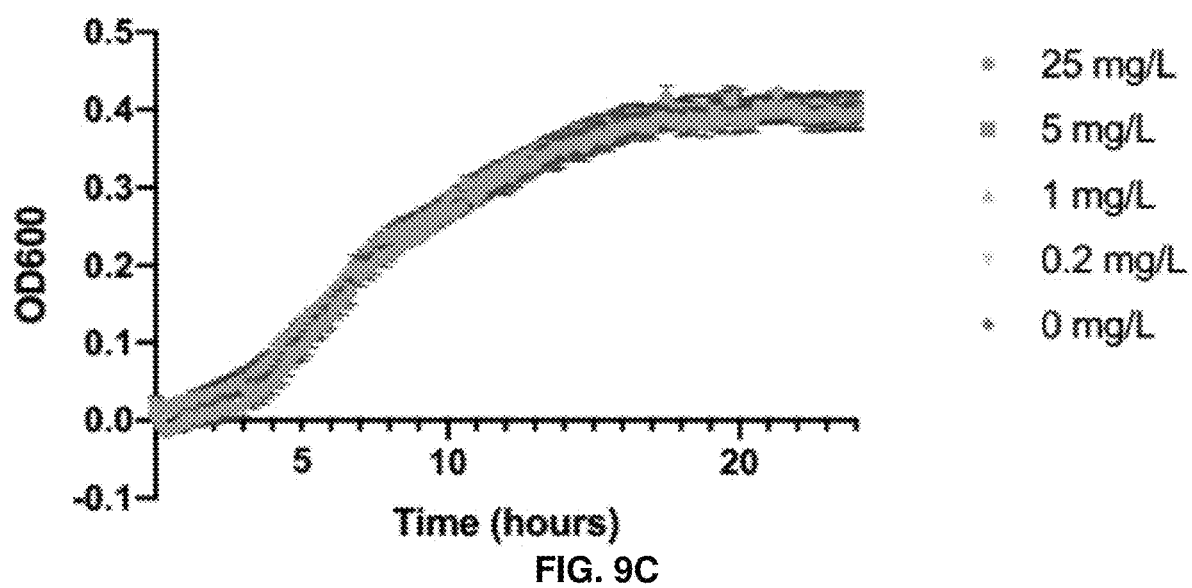
FIG. 9C. Evaluation of the effect of Ir(Me)MPIX and cyclopropyl limonene on cell growth. The presence of cyclopropyl limonene has little effect on the growth of BL21(DE3) cells co-transformed with pHug21 and pJHA110 (encoding CYP119) under the range of concentrations tested. Error bars represent 1 standard deviation of three biological replicates.

Cyclopropyl Limonene Biosynthesis. Having achieved the diastereoselective cyclopropanation of (−)-carvone with EDA in cells expressing CYP119, even at a relatively low level, we sought to integrate such reactivity with the biosynthesis of limonene from a simple sugar (FIG. 3A). Again, we assessed whether the expression of the artificial metalloenzyme would affect the production of limonene. The production of limonene was unaffected by the expression level of CYP119 achieved with the pJHA135 plasmid (FIG. 3B). Moreover, the limonene titer was unaffected by the presence of 0.1 μM Ir(Me)MPIX (FIG. 6B). Finally, both Ir(Me)MPIX and cyclopropyl limonene did not inhibit cell growth within the concentration range relevant for our study (FIGS. 9A to 9C).

The cyclopropanation of limonene added exogenously to the whole-cell system catalyzed by $E.$ $coli$ expressing the hug operon and CYP119 in the M9-rich medium was then evaluated. These cells produced the cyclopropyl limonene with a diastereoselectivity of 52% (1.0:3.3:1.1:1.0 dr) (FIG.

Figure 3C:
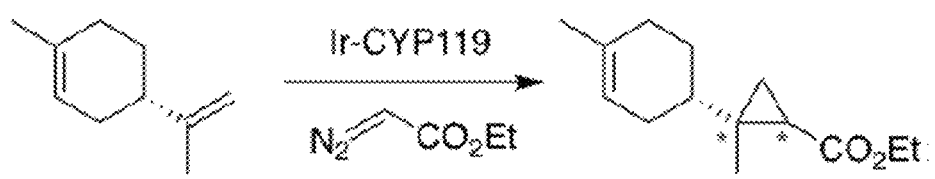
FIG. 3C. Combining limonene biosynthesis with ArM. E. coli cells expressing Ir-CYP119 catalyzed the cyclopropanation of exogenously added (−)-limonene with diastereoselectivity distinct from that of the free cofactor and enhanced over that of the reaction in vitro. $P_1$-$P_4$ are the four diastereomeric products numbered in the order of elution by GC. The selectivity of $P_1$-$P_4$ corresponds to the ratio of each diastereomer versus the total of the four diastereomeric products. $P_{total}$ is the sum of four diastereomeric products. All data from whole-cell reactions are shown as the average from three biological replicates, with error bars indicating 1 standard deviation.
Figure 3C:
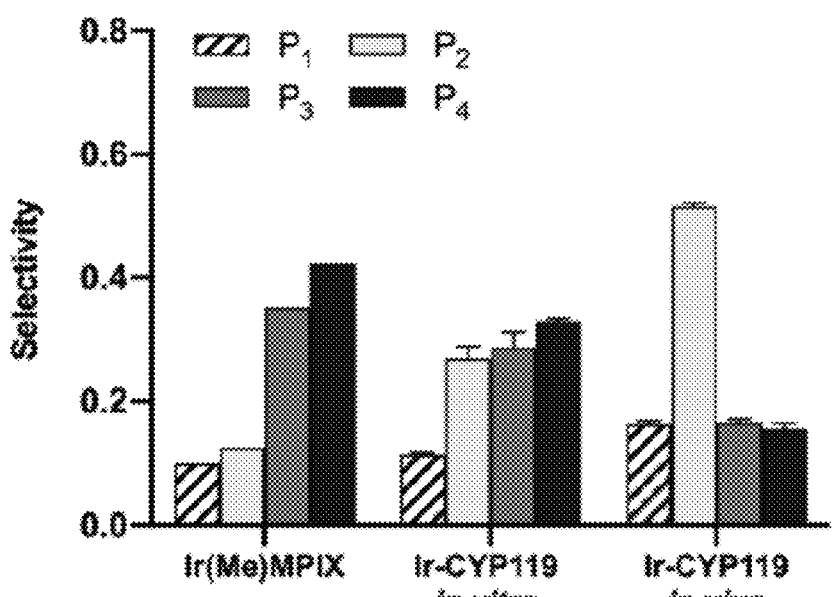

3C). This ratio of diastereomers is distinct from that of the reaction catalyzed by free Ir(Me)MPIX (1.0:1.2:3.5:4.2 dr) and the diastereoselectivity was fortuitously higher than that of the reaction catalyzed by the same Ir-CYP119 mutant in vitro (1.0:2.4:2.3:2.9 dr) (FIG. 3C). We suggest that the higher diastereoselectivity in the whole-cell system results from a greater stability of the enzyme in vivo than in vitro.

Figure 3D:
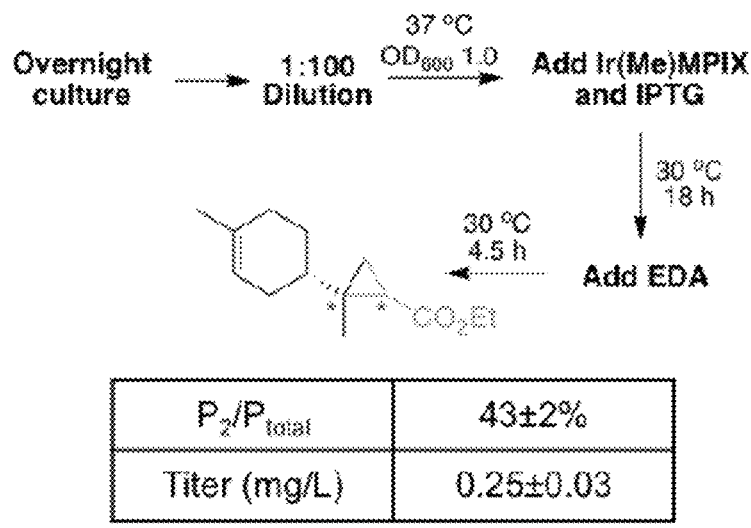
FIG. 3D. Combining limonene biosynthesis with ArM. The cyclopropyl limonene was produced diastereoselectively from glucose in E. coli expressing the limonene pathway/hug operon/CYP119. $P_1$-$P_4$ are the four diastereomeric products numbered in the order of elution by GC. The selectivity of $P_1$-$P_4$ corresponds to the ratio of each diastereomer versus the total of the four diastereomeric products. $P_{total}$ is the sum of four diastereomeric products. All data from whole-cell reactions are shown as the average from three biological replicates, with error bars indicating 1 standard deviation.
Figure 10A:
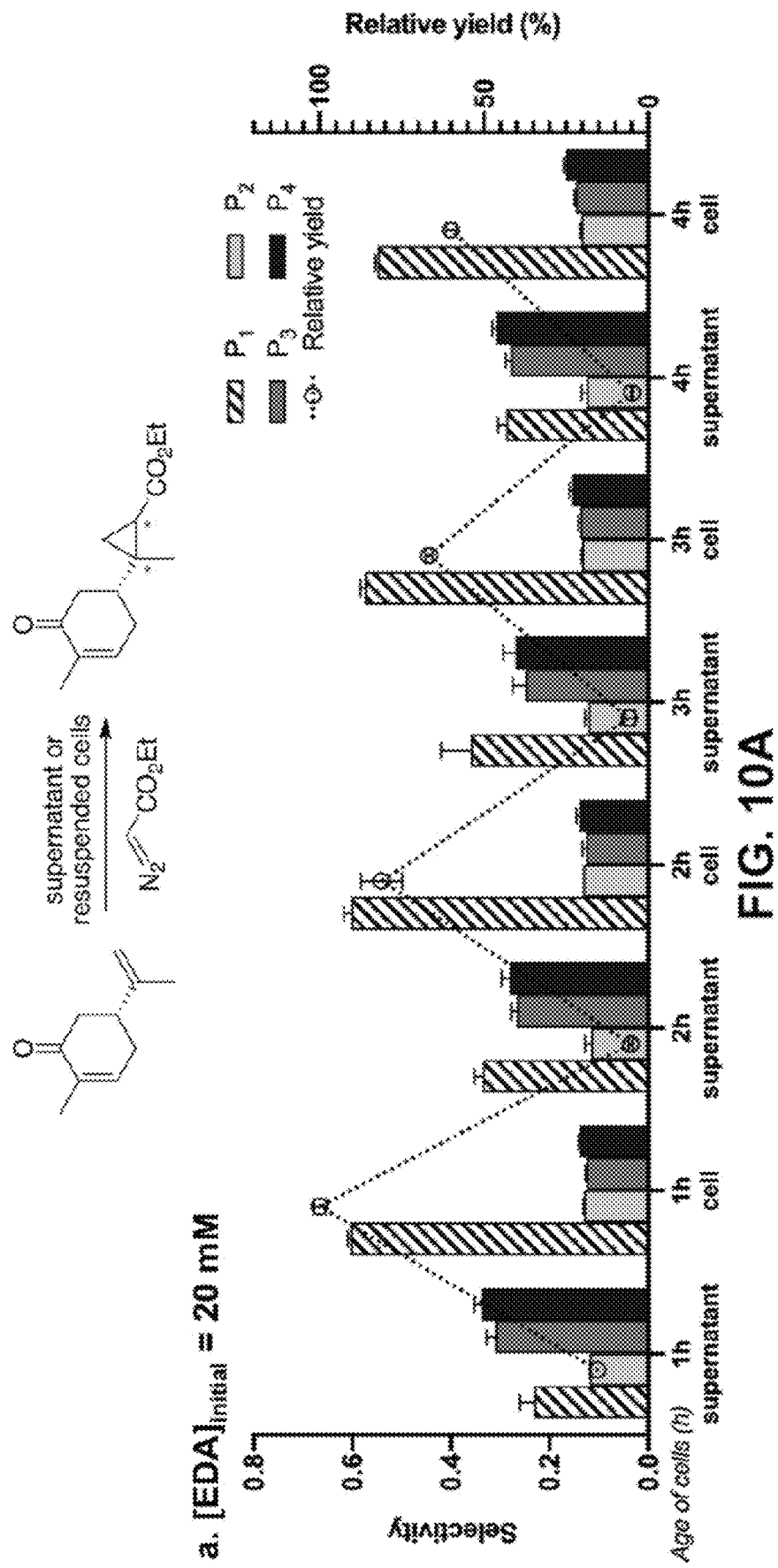
FIG. 10A. The cyclopropanation of (−)-carvone catalyzed by supernatants and resuspended cell pellets. The E. coli cultures expressing the artificial biosynthetic pathway were supplemented with 20 mM EDA to initiate the production of cyclopropyl limonene. Aliquots were removed from the cell culture and centrifuged to separate the media and cells at each one-hour interval. Cell pellets were resuspended in fresh M9-rich medium. Then the supernatants and resuspended cell pellets were used to catalyze the reaction of (−)-carvone with EDA. Reaction conditions: supernatant or resuspended cell pellets, 4 mM (−)-carvone, 20 mM EDA, 1% ethanol, 350 µL M9-rich medium, 30° C., 2 h. The relative yields of these reactions were calculated by normalizing the reactivity of the cells that were separated one hour after the addition of EDA as 100%. All data are shown as the average from three biological replicates, with error bars indicating 1 standard deviation.
Figure 10B:
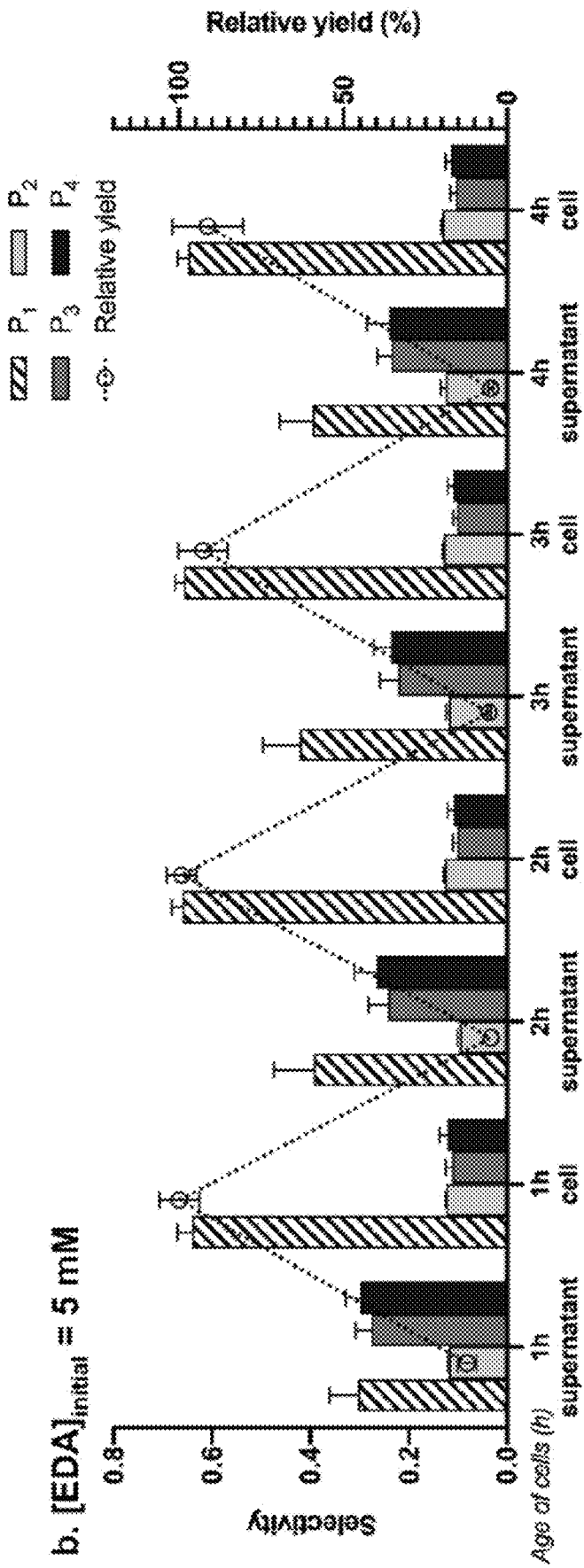
FIG. 10B. The cyclopropanation of (−)-carvone catalyzed by supernatants and resuspended cell pellets. The E. coli cultures expressing the artificial biosynthetic pathway were supplemented with 5 mM EDA to initiate the production of cyclopropyl limonene. Aliquots were removed from the cell culture and centrifuged to separate the media and cells at each one-hour interval. Cell pellets were resuspended in fresh M9-rich medium. Then the supernatants and resuspended cell pellets were used to catalyze the reaction of (−)-carvone with EDA. Reaction conditions: supernatant or resuspended cell pellets, 4 mM (−)-carvone, 20 mM EDA, 1% ethanol, 350 µL M9-rich medium, 30° C., 2 h. The relative yields of these reactions were calculated by normalizing the reactivity of the cells that were separated one hour after the addition of EDA as 100%. All data are shown as the average from three biological replicates, with error bars indicating 1 standard deviation.
Figure 11A:
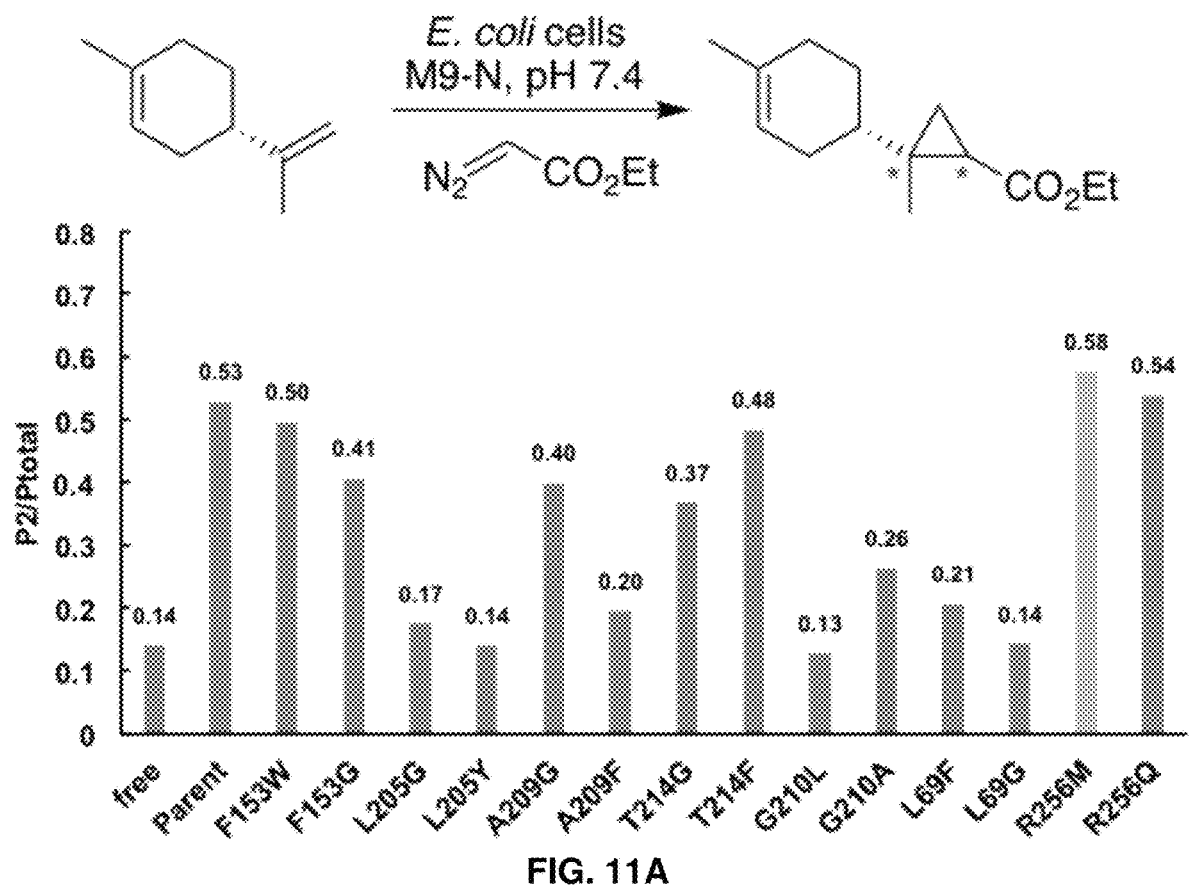
FIG. 11A. Directed evolution of CYP119 mutants for the diastereoselective cyclopropanation of (−)-limonene. Site-directed mutagenesis of the CYP119 parent mutant was performed at F153, L205, A209, T214, G210, L69 and R256 and mutants were screened for higher diastereoselectivity. The cyclopropanation of (−)-limonene was catalyzed by E. coli cells containing pHug21 and a plasmid coding for CYP119 mutants. Parent designates CYP119 mutant (C317G, T213G, V254L, L155W). Free: Ir(Me)MPIX. P2/Ptotal is the ratio of the peak area of the second diastereomer in the order of elution by GC to the peak area of all four diastereomeric products. Ptotal represents the peak area of all four diastereomers.
Figure 11B:
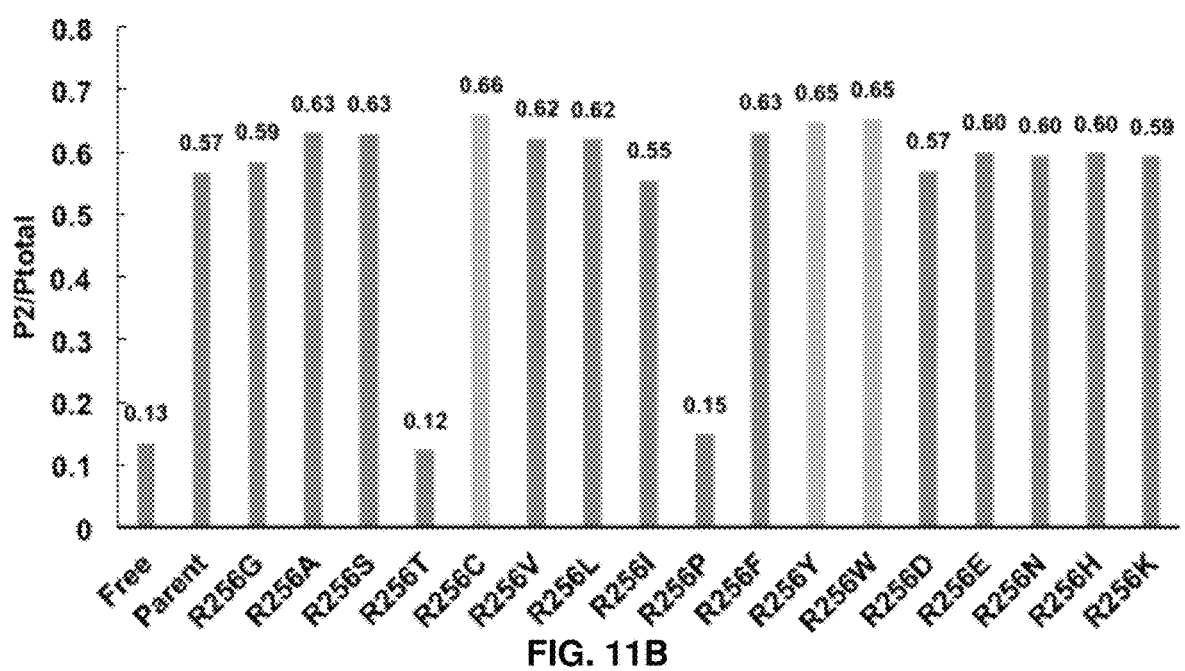
FIG. 11B. Directed evolution of CYP119 mutants for the diastereoselective cyclopropanation of (−)-limonene. Site-saturation mutagenesis was performed at R256 and mutants were screened for higher diastereoselectivity. The cyclopropanation of (−)-limonene was catalyzed by E. coli cells containing pHug21 and a plasmid coding for CYP119 mutants. Parent designates CYP119 mutant (C317G, T213G, V254L, L155W) P2/Ptotal is the ratio of the peak area of the second diastereomer in the order of elution by GC to the peak area of all four diastereomeric products. Ptotal represents the peak area of all four diastereomers.
Figure 11C:
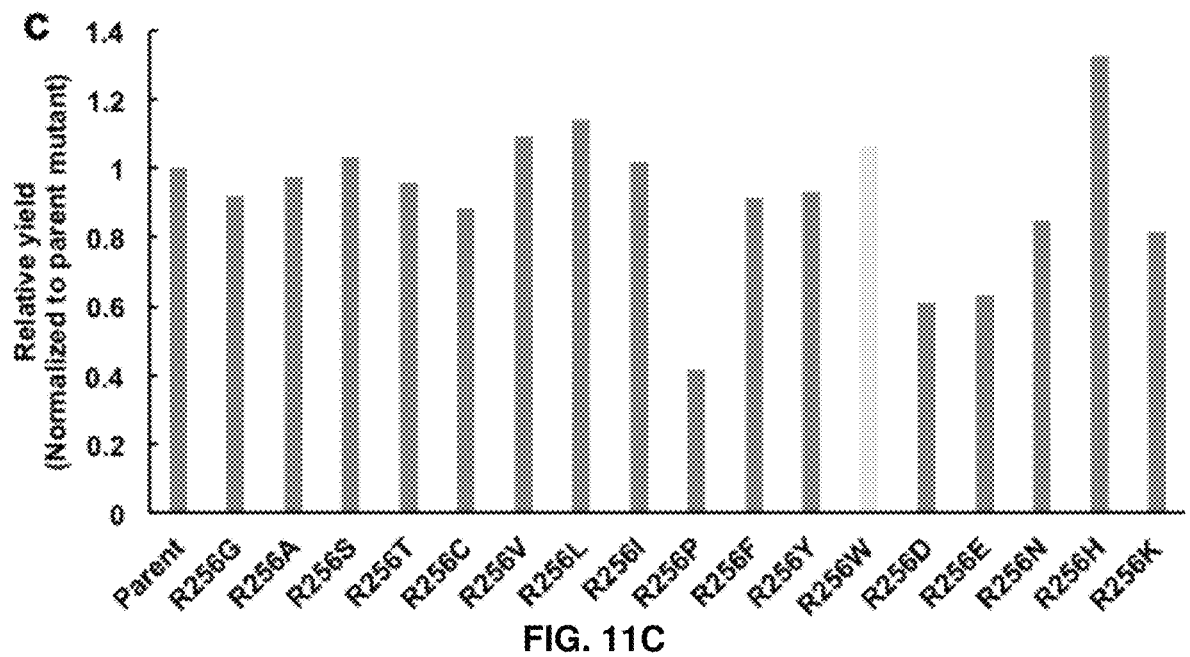
FIG. 11C. Directed evolution of CYP119 mutants for the diastereoselective cyclopropanation of (−)-limonene. Site-saturation mutagenesis was performed at R256 and mutants were screened for higher yield. The cyclopropanation of (−)-limonene was catalyzed by E. coli cells containing pHug21 and a plasmid coding for CYP119 mutants. Parent designates CYP119 mutant (C317G, T213G, V254L, L155W). Ptotal represents the peak area of all four diastereomers. The relative yield was calculated by normalizing the yield of the reaction catalyzed by the parent mutant as 1.
Figure 11D:
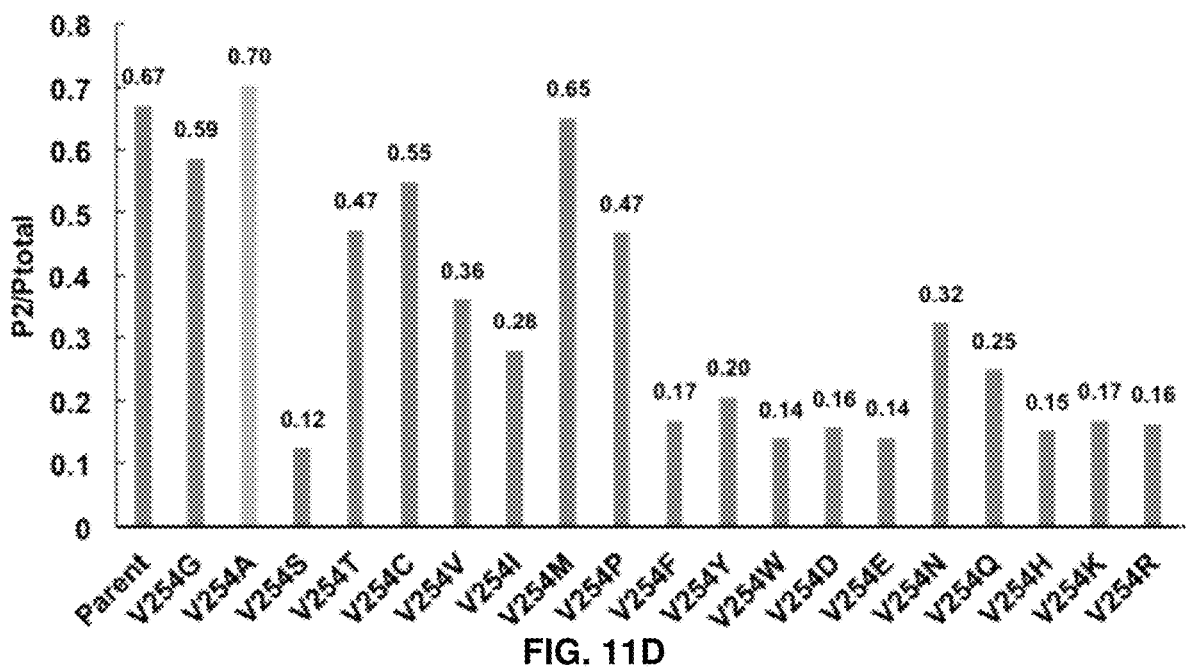
FIG. 11D. Directed evolution of CYP119 mutants for the diastereoselective cyclopropanation of (−)-limonene. Site-saturation mutagenesis was performed at V254 and mutants were screened for higher diastereoselectivity. The cyclopropanation of (−)-limonene was catalyzed by E. coli cells containing pHug21 and a plasmid coding for CYP119 mutants. Parent designates CYP119 mutant (C317G, T213G, V254L, L155W, R256W). P2/Ptotal is the ratio of the peak area of the second diastereomer in the order of elution by GC to the peak area of all four diastereomeric products. Ptotal represents the peak area of all four diastereomers.

To fully combine terpene production and artificial catalysis within the same cell, gene expression for limonene biosynthesis and CYP119 was induced concurrently with addition of Ir(Me)MPIX (FIG. 3D). After overnight incubation, the synthesis of cyclopropyl limonene was initiated by addition of EDA. Under these conditions, 250 µg/L of cyclopropyl limonene was produced after 4.5 h with diastereoselectivity (43%, 1.0:3.2:1.8:1.5 dr) that was within 10% of that of the whole-cell reaction with exogenously added limonene. This similarity in diastereoselectivity indicates that the cyclopropyl limonene is formed from the combination of the heterologous biosynthesis of limonene and cyclopropanation catalyzed by the ArM. To assess the possibility that formation of the cyclopropane was catalyzed by the Ir-CYP119 released from dead cells, the cells were separated from the culture by centrifugation. The catalytic activity of the supernatant and of resuspended cells was evaluated by the reaction of (−)-carvone and EDA. The formation of cyclopropyl carvone with resuspended cells occurred with high diastereoselectivity and a yield more than 10 times that of the reaction conducted with the supernatant (FIGS. 10A to 10B). These data show that the product was produced primarily by intact cells.

Figure 4A:
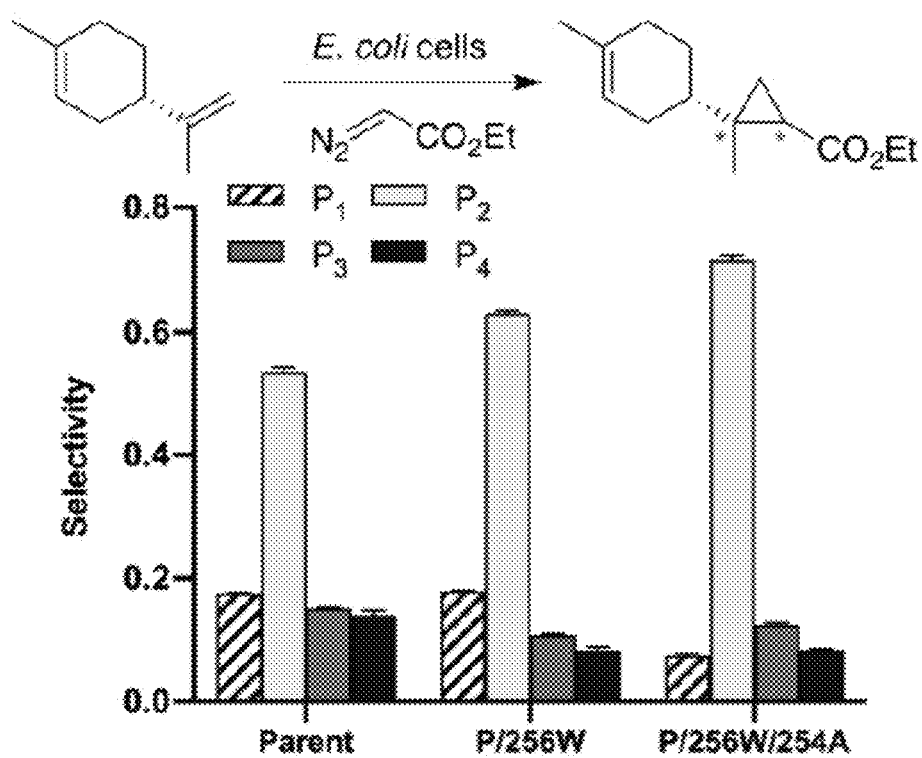
FIG. 4A. Increasing the diastereoselectivity and titer of cyclopropyl limonene by directed evolution and process optimization. Directed evolution of CYP119 mutants with higher diastereoselectivity. The diagram shows different conditions used for the production of cyclopropyl limonene by the artificial biosynthetic pathway. The concentrations of reagents listed in the diagram are the final concentrations in culture media. All data are shown as the average from three biological replicates, with error bars indicating 1 standard deviation.
Figure 4B:
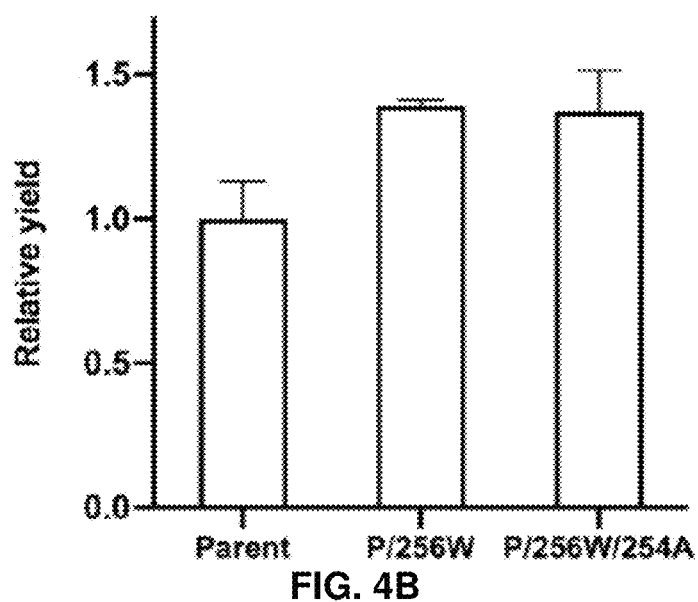
FIG. 4B. Increasing the diastereoselectivity and titer of cyclopropyl limonene by directed evolution and process optimization. The evolved mutants also catalyzed the cyclopropanation in higher yields. The relative yield is the amount of cyclopropyl limonene formed from the whole-cell reaction catalyzed by evolved CYP119 mutants relative to that of the reaction with the parent mutant. The diagram shows different conditions used for the production of cyclopropyl limonene by the artificial biosynthetic pathway. The concentrations of reagents listed in the diagram are the final concentrations in culture media. All data are shown as the average from three biological replicates, with error bars indicating 1 standard deviation.
Figure 12:
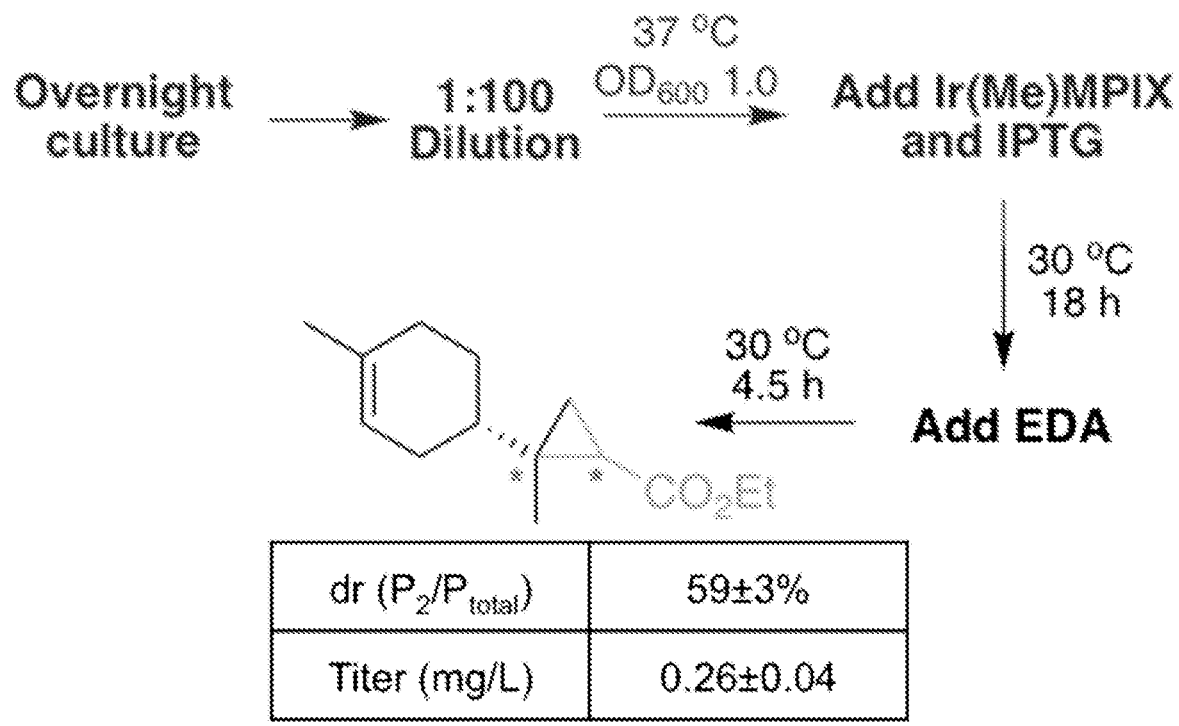
FIG. 12. Process to evaluate the evolved CYP119 mutant (C317G, T213G, V254A, L155W, R256W) and resulting dr and titer using this mutant. E. coli strain co-transformed with pJBEI6410 (encoding limonene pathway) and pJHA170 (plasmid coding for both the HUG system and evolved CYP119 mutant) was used to produce cyclopropyl limonene. The process is the same as the experiment in FIG. 3D. All data are shown as the average from three biological replicates.

Increasing diastereoselectivity and titer. To increase the diastereoselectivity and titer of the cyclopropyl limonene from the artificial pathway, we evolved the CYP119 mutant. We constructed a small library of CYP119 mutants containing additional changes to the amino acids around the binding site of the cofactor and tested the diastereoselectivity of these mutants for the cyclopropanation of limonene in whole cells (FIGS. 11A to 11D). After three rounds of screening, mutant P/R256W/V254A (P designates the parent) catalyzed the cyclopropanation of limonene with a higher diastereoselectivity of 72% (1.0:9.6:1.7:1.1 dr) and a higher yield (FIGS. 4A and 4B). This evolved mutant was then introduced into the E. coli strain containing the limonene pathway and hug operon to perform artificial production of cyclopropyl limonene. With the procedures previously developed (FIG. 3D), the titer and diastereoselectivity of the products formed from this new pathway were 265 µg/L and 59% (1.0:7.0:2.3:1.5 dr) respectively (FIG. 12).

Figure 4C:
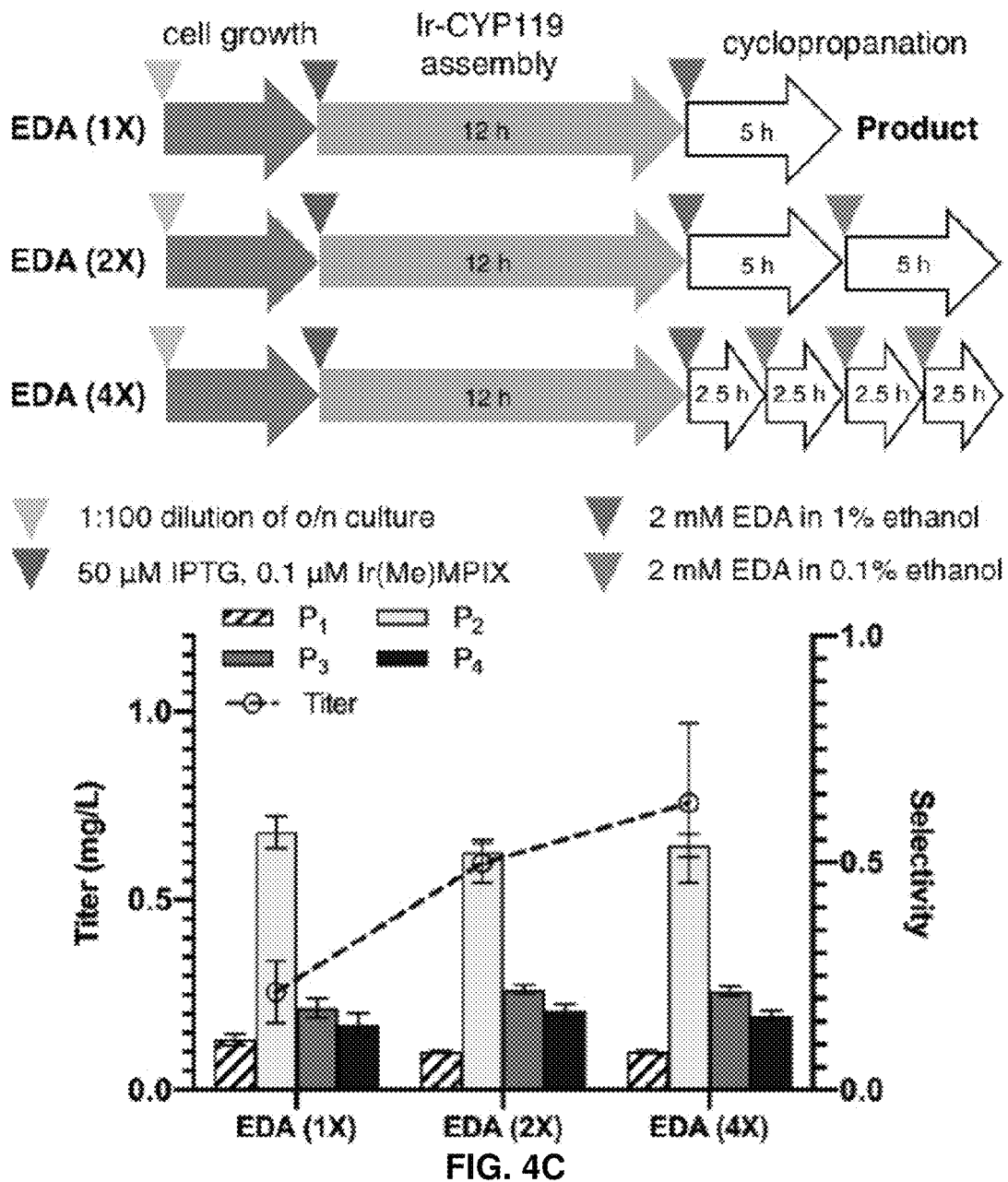
FIG. 4C. Increasing the diastereoselectivity and titer of cyclopropyl limonene by directed evolution and process optimization. The improved titer of cyclopropyl limonene with evolved CYP119 mutant (C317G, T213G, V254A, L155W, R256W) and batch-wise addition of EDA. The diagram shows different conditions used for the production of cyclopropyl limonene by the artificial biosynthetic pathway. The concentrations of reagents listed in the diagram are the final concentrations in culture media. All data are shown as the average from three biological replicates, with error bars indicating 1 standard deviation.
Figure 13:
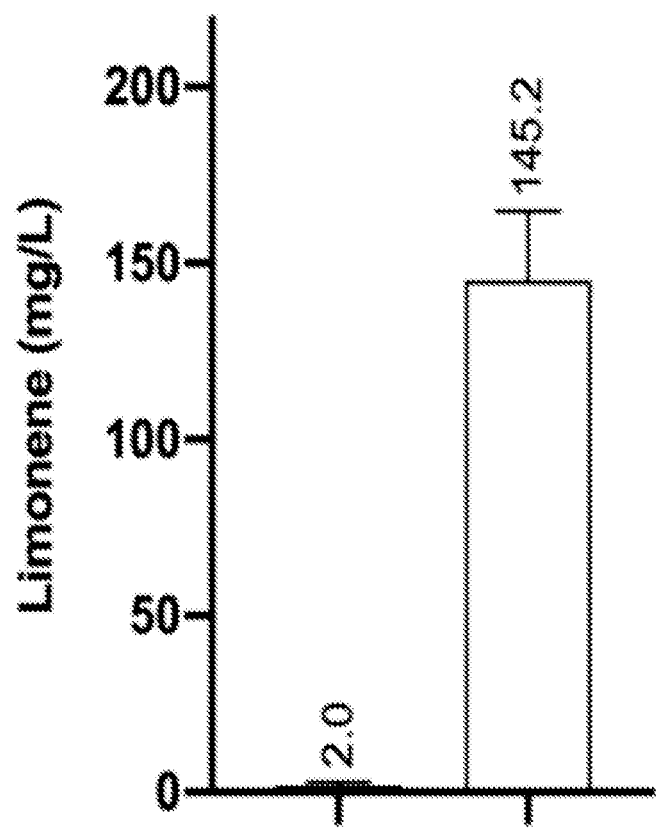
FIG. 13. The titer of limonene from the E. coli culture without dodecane overlay was much lower than that with an overlay. Limonene was produced from E. coli cells expressing the artificial biosynthetic pathway (pJBEI6410+pJHA170) and the titer was determined 18 hours after the induction of protein expression. For the cell culture without dodecane overlay, aliquots were removed and extracted with equal volume of ethyl acetate containing internal standard. The limonene titer was analyzed by GC-MS. All data are shown as the average from three biological replicates, with error bars indicating 1 standard deviation.
Figure 14A:
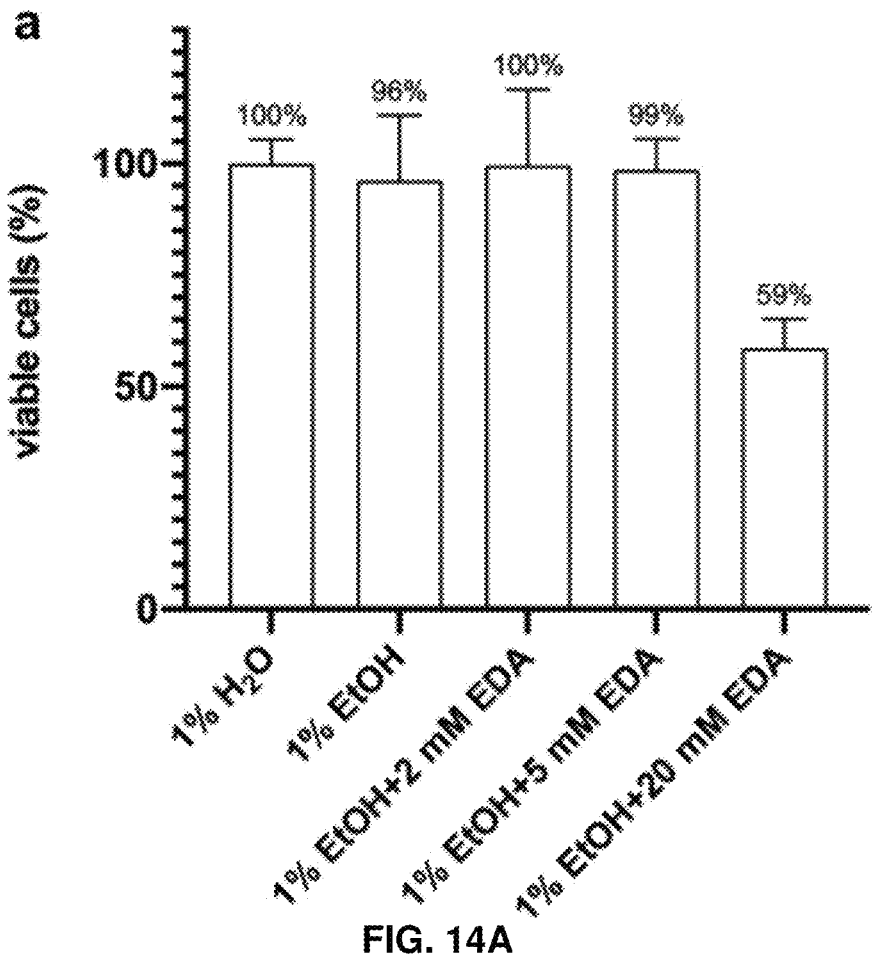
FIG. 14A. The toxicity and consumption rate of EDA in the artificial pathway. High concentration of EDA is toxic to E. coli cells. The figure shows the percentages of viable cells in the E. coli culture expressing the artificial biosynthetic pathway (pJBEI6410+pJHA170) after exposing to different concentrations of EDA for 4 h. The percentage of viable cells was calculated by normalizing the number of colonies grown in the control group (with 1% ddH$_2$O) as 100%. All data are shown as the average from three biological replicates, with error bars indicating 1 standard deviation.
Figure 14B:
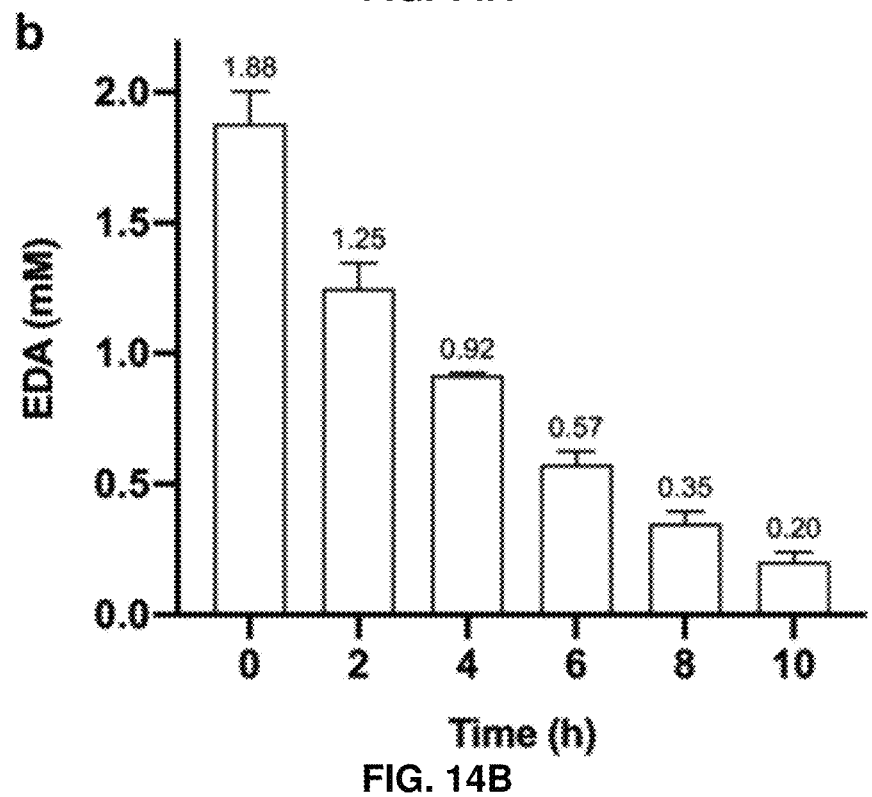
FIG. 14B. The toxicity and consumption rate of EDA in the artificial pathway. The rate of EDA consumption in the E. coli culture expressing the artificial biosynthetic pathway (pJBEI6410+pJHA170). All data are shown as the average from three biological replicates, with error bars indicating 1 standard deviation.
Figure 15A:
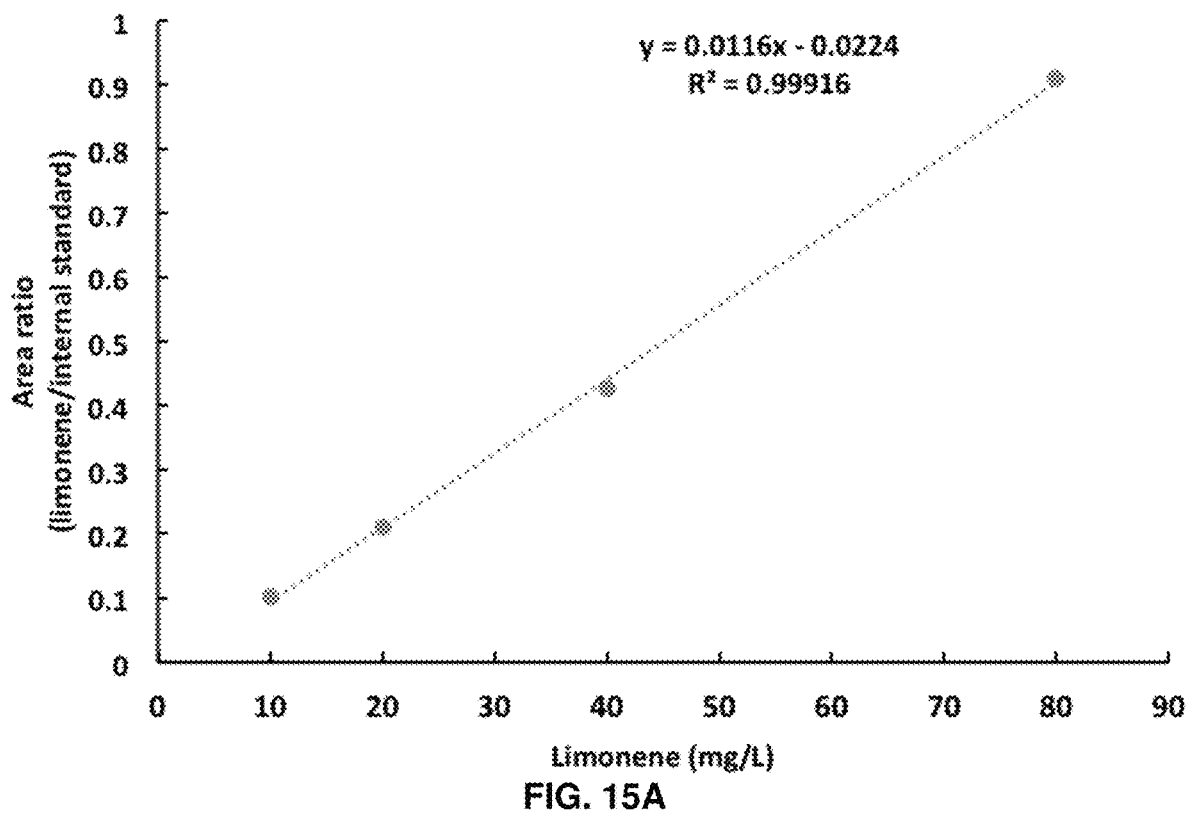
FIG. 15A. Calibration curves for limonene (GC-MS).
Figure 15B:
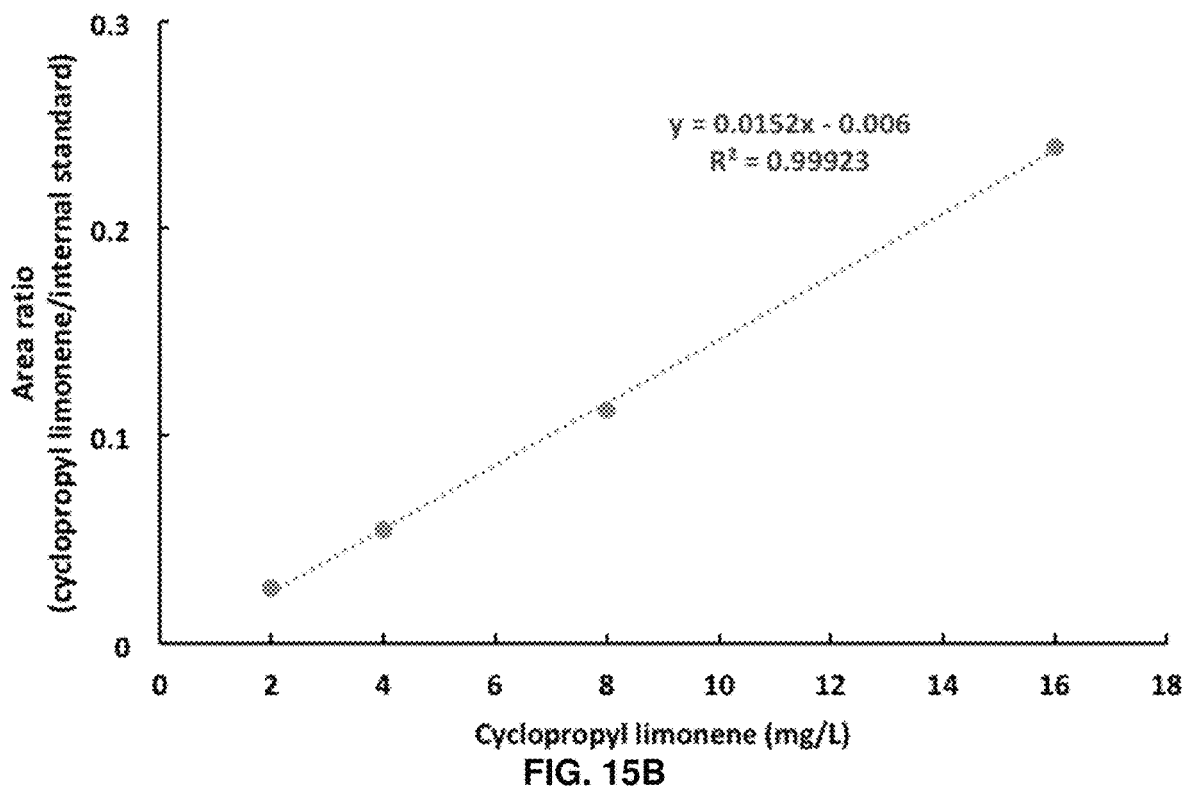
FIG. 15B. Calibration curves for cyclopropyl limonene (GC-MS).
Figure 15C:
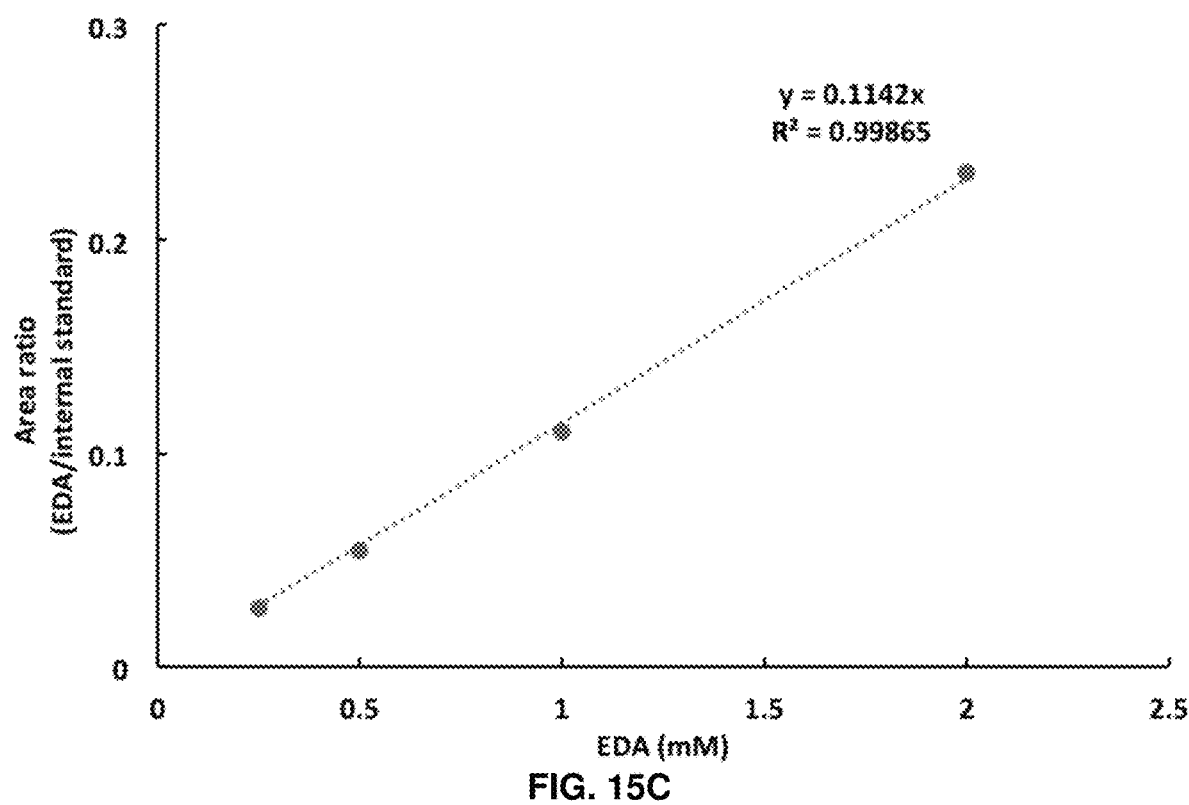
FIG. 15C. Calibration curves for EDA (GC-FID).

The conversion efficiency of limonene by natural P450s in heterologous hosts is known to be low[30,33], and the titer of cyclopropyl limonene is limited, in part, by the volatility of limonene. The titer of limonene is just 2 mg/L when the cells are grown without an organic overlay, but is 145 mg/L when the cells are grown with a dodecane overlay (FIG. 13). However, an overlay is used only if limonene is the final product; it would be incompatible with our system in which we must preserve limonene intracellularly as a substrate for the ArM. Thus, we sought to optimize the titer of cyclopropyl limonene by alternate methods. To do so, we investigated the potential toxicity of EDA to E. coli in the process of producing cyclopropyl limonene and investigated the effect of adding EDA portion-wise (FIGS. 14A and 14B). We found that addition of EDA at an initial concentration of 2 mM and refeeding EDA three times over 10 h led to a titer of cyclopropyl limonene that was almost 3 times its initial value (from 258 ug/L to 760 µg/L) with little change in diastereoselectivity (54%, 1.0:6.4:2.6:1.9 dr) (FIG. 4C). Additional increases in product titer would likely be gained by further optimization of the protocol for feeding EDA, investigation of additional enzyme mutants, and manipulating the expression levels of proteins in the pathway.

CONCLUSIONS

Production of an unnatural product using a microorganism engineered with a heterologous natural product biosynthetic pathway, an ArM, and a heterologous cofactor transport system demonstrates the feasibility of creating organic molecules by artificial biosynthesis comprising synthetic biology and synthetic chemistry. One can envision this combination of biosynthesis and artificial metalloenzymes being applied to engineered pathways that produce unusual core structures, with enzymes that catalyze functionalization of C—H bonds to install abiotic groups at positions where P450s might operate naturally, or with the artificial metalloenzyme operating in the middle of a pathway followed by diversification of the abiotic product with evolved downstream enzymes. One can even envision creating reagents, such as diazoesters, biosynthetically based on known pathways to these species[34]. Such goals could be achieved in E. coli or in a range of organisms that produce diverse classes of natural products, such as polyketides or various alkaloids, thus opening a realm of biosynthesis beyond that limited by the scope of natural reactions.

Methods

General procedure for the artificial biosynthesis of cyclopropyl limonene. BL21(DE3) cells were transformed with a plasmid (pJBEI6410) coding for enzymes in limonene biosynthetic pathway and a plasmid (pJHA135 or pJHA170) encoding both the heme transport system HUG and the corresponding CYP119 mutant. Individual colonies from freshly transformed plates (incubated at 30° C.) were inoculated into 2 mL M9-rich medium supplemented with 100 µg/mL carbenicillin and 25 µg/mL kanamycin. The cultures were grown overnight at 30° C., 200 rpm for 18 h. In a 50 mL glass culture tube, 10 mL of M9-rich medium was inoculated with 100 µL of overnight starter culture and incubated at 37° C., 200 rpm to an $OD_{600}$ of ~1. The cultures were then induced by adding 50 µM IPTG, at which time 2 µL of a 0.5 mM solution of Ir(Me)MPIX in DMSO was added to give a final Ir(Me)MPIX concentration of 0.1 µM. Upon induction, the incubation temperature was reduced to 30° C., and expression was allowed to continue for 18 h at 200 rpm. To the 10 mL culture was added 21.2 µL EDA dissolved in 100 µL ethanol to give a final EDA concentration of 20 mM and a final ethanol concentration of 1% (v/v), and the mixture was further incubated at 30° C., 200 rpm for 4.5 h. To analyze the titer of cyclopropyl limonene, aliquots of cell culture (1.4 mL) were removed from the tube and extracted with an equal volume of ethyl acetate. The organic layer (1 mL) was concentrated to 90 µL with a Speedvac, and to this concentrate was added 10 µL of ethyl acetate containing 1 g/L (−)-carvone (carvone used as internal standard). The final solution was analyzed by GC-MS.

1. General methods. Unless otherwise noted, the chemicals, salts, and solvents used were reagent grade and used as received from commercial suppliers without further purification. Oligonucleotides were obtained from Integrated DNA Technologies. Enzymes and reagents used for cloning were obtained from New England BioLabs and Thermo Fisher Scientific. pChuA was a gift from Alan Jasanoff (Addgene plasmid 42539). pHug21 was a gift from Prof Douglas Henderson in the University of Texas Permian Basin. All expression media and buffers were prepared using ddH$_2$O (MilliQ A10 Advantage purification system, Millipore). All expression media were sterilized using either an autoclave (30 min, 121° C.) or a sterile syringe filter (0.22 µm). The synthetic procedures of Ir(Me)MPIX were reported previously.[1]

2. Plasmids and site-directed mutagenesis. The plasmids used in this study are listed in the table below. The sequences of CYP119,[2] heme transport protein ChuA (Addgene_42539), and heme utilization system HUG[3] were described elsewhere and cloned into the respective vectors. Primer sequences are available upon request. Site-directed mutagenesis was used to introduce mutations into pJHA110. Phusion High-Fidelity DNA polymerase was used to amplify the parent plasmid with primers containing mutations at target sites. After DpnI digestion, the PCR product was purified with a QIAGEN gel purification kit and ligated with T4 ligase and T4 PNK (polynucleotide kinase). All pBb plasmids shown in Table 1 were constructed in previous study.[4]

TABLE 1

Plasmids.

| Name | Marker | Origin | Vector backbone | Genes |
|---|---|---|---|---|
| pCYP119-141[1] | Amp | ColE1 | 2BT(Addgene_29666) | CYP119-141 mutant (C317G, T213G, V254L, L155W) with T7 promoter |
| pJHA147 | Kan | p15A | pBbA5a | ChuA with lacUV5 promoter |
| pHug21[3] | Amp | SC101 | — | hug operon |
| pJHA029 | Amp | ColE1 | pBbE5a | CYP119-141 mutant with lacUV5 promoter |
| pJHA108 | Kan | ColE1 | pBbE1K | CYP119-141 mutant with trc promoter |
| pJHA110 | Kan | ColE1 | pBbE5K | CYP119-141 mutant with lacUV5 promoter |
| pJHA047 | Kan | SC101 | pBbS8K | hug operon |
| pJHA135 | Kan | SC101 | pBbS8K | hug operon and CYP119 mutant (C317G, T213G, V254L, L155W) with trc promoter |
| pJHA170 | Kan | SC101 | pBbS8K | hug operon and CYP119 mutant (C317G, T213G, V254A, L155W, R256W) with trc promoter |
| pJHA184 | Amp | SC101 | pBbS5A | chuA, tonB, exbB and exbD cloned from E. coli O6:K5:H1[5] |
| pBbS5A | Amp | SC101 | — | RFP with lacUV5 promoter |
| pBbE7A | Amp | ColE1 | — | RFP with T7 promoter |
| pJBEI6409[6] | Cm | p15A | pBbA5c | genes for limonene synthesis |
| pJBEI6410[6] | Amp | p15A | pBbA5a | genes for limonene synthesis |

3. Media preparation. Preparation of M9-rich media: Salts (47.7 mM Na$_2$HPO$_4$, 22.0 mM KH$_2$PO$_4$, 8.6 mM NaCl, 1 g/L NH$_4$Cl) were dissolved in 1 L ddH$_2$O and autoclaved to give a medium with pH ~7. Solutions of glucose (20 w/v %), casein hydrolysate (20 w/v %), MgSO$_4$ (1 M), antibiotics and CaCl$_2$ (1 M) were sterilized by filter. The following amounts of the listed solutions were added per liter of sterilized salt solution: 40 mL glucose, 10 mL casein hydrolysate, 2 mL MgSO$_4$, 100 µL CaCl$_2$.

Preparation of M9-N reaction buffer: Salts (47.7 mM Na$_2$HPO$_4$, 22.0 mM KH$_2$PO$_4$, 8.6 mM NaCl) were dissolved in 1 L ddH$_2$O and autoclaved to give a medium with pH ~7.4. Solutions of MgSO$_4$ (1 M), CaCl$_2$ (1 M) and glucose (20 w/v %) were added to give a final concentration of 2.0 mM MgSO$_4$, 0.1 mM CaCl$_2$, 0.4 w/v % glucose.

4. In vivo expression of Ir-CYP119. A plasmid containing CYP119 genes was co-transformed with a plasmid encoding the corresponding heme transport system (ChuA, HUG or truncated HUG system) into chemically competent BL21 (DE3) cells (NEB). Individual colonies from freshly transformed plates (incubated at 30° C.) were inoculated into 2 mL M9-rich media supplemented with 100 µg/mL carbenicillin and 50 µg/mL kanamycin (for low copy plasmids with SC101 origin, the concentration of the antibiotics was reduced by half). The cultures were grown for 18 h at 30° C., 200 rpm. In a 50 mL glass culture tube, 10 mL of M9-rich media was inoculated with 100 µL of overnight starter culture and incubated at 37° C., 200 rpm to an OD$_{600}$ of ~1. Unless otherwise indicated, the cultures were then induced by adding final concentration of 50 µM IPTG and 0.1 µM Ir(Me)MPIX (2 µL of 0.5 mM stock solution in DMSO). Upon induction, the incubation temperature was reduced to 30° C., and expressions were allowed to continue for 18 h at 200 rpm. After harvesting the cells by centrifugation (RT, 1 min, 10,000 rpm), the cell pellets were resuspended in M9-N reaction buffer to an OD$_{600}$ of ~10.

5. Whole-cell reactions. The cell suspension in M9-N reaction buffer (350 µL, OD$_{600}$~10) was transferred into a 2 mL screw-capped GC vial, and 4 mM substrate ((−)-carvone or (−)-limonene) and 20 mM EDA were added. Both stock solutions were prepared in ethanol and added to the cell culture to give a final ethanol concentration of 1% (v/v). The vials were capped and shaken at 30° C. and 200 rpm for 4 h. The reaction was quenched by adding 24 µL of 2 N HCl, followed by 160 µL saturated NaCl and 800 µL ethyl acetate (containing 160 mg/L dodecane as internal standard). The mixture was subjected to vortex at 2500 rpm for 4 min, transferred to a 1.7 mL microcentrifuge tube, and centrifuged at 5,000 rpm for 2 min. After separation of the layers, approximately 500 µL of the aqueous phase was removed from the bottom of the vial by pipette. The remaining contents of the vial were neutralized by the addition of saturated NaHCO$_3$ (160 µL). The microcentrifuge tube was then vortexed at 2500 rpm for 1 min and centrifuged at 15,000 rpm for 4 min. The organic layer was then transferred to a separate vial for GC analysis.

6. Limonene biosynthesis. Chemically competent BL21 (DE3) (NEB) cells were transformed with a plasmid coding for MEV pathway enzymes to produce limonene from glucose in E. coli (pJBEI6410 or pJBEI6409). Individual colonies from freshly transformed plates (incubated at 30° C.) were inoculated into 2 mL M9-rich media supplemented with 100 µg/mL carbenicillin or 25 µg/mL chloramphenicol, respectively. The cultures were grown overnight at 30° C. and 200 rpm for 18 h. In a 50 mL glass culture tube, 10 mL of M9-rich media was inoculated with 100 µL of overnight starter culture and incubated at 37° C. and 200 rpm to an OD$_{600}$ of ~1. Unless otherwise indicated, the cultures were then induced by adding 50 µM IPTG (final concentration), and 10% (v/v) dodecane was added to trap the limonene produced. Upon induction, the temperature was reduced to 30° C. and expressions were allowed to continue for 24 h at 200 rpm. An aliquot of the 100 µL dodecane overlay was diluted with 900 µL ethyl acetate containing 40 mg/L beta-pinene (beta-pinene as internal standard) and analyzed by GC-MS.

7. Artificial pathway for the production of cyclopropyl limonene. General procedure: BL21(DE3) cells were transformed with a plasmid (pJBEI6410) coding for enzymes in limonene biosynthetic pathway and a plasmid (pJHA135 or pJHA170) encoding both the heme transport system HUG and the corresponding CYP119 mutant. Individual colonies from freshly transformed plates (incubated at 30° C.) were inoculated into 2 mL M9-rich media supplemented with 100 μg/mL carbenicillin and 25 μg/mL kanamycin. The cultures were grown overnight at 30° C., 200 rpm for 18 h. In a 50 mL glass culture tube, 10 mL of M9-rich media was inoculated with 100 μL of overnight starter culture and incubated at 37° C., 200 rpm to an $OD_{600}$ of ~1. The cultures were then induced by adding 50 μM IPTG, at which time 2 μl of a 0.5 mM solution of Ir(Me)MPIX in DMSO was added to give a final Ir(Me)MPIX concentration of 0.1 μM. Upon induction, the incubation temperature was reduced to 30° C., and expression was allowed to continue for 18 h at 200 rpm. To the 10 mL culture was added 21.2 μl EDA dissolved in 100 μl ethanol to give a final EDA concentration of 20 mM and a final ethanol concentration of 1% (v/v), and the mixture was further incubated at 30° C., 200 rpm for 4.5 h. To analyze the titer of cyclopropyl limonene, aliquots of cell culture (1.4 mL) were removed from the tube and extracted with an equal volume of ethyl acetate as described in the section of whole-cell reaction. The organic layer (1 mL) was concentrated to 90 μL with a Speedvac, and to this concentrate was added 10 μL of ethyl acetate containing 1 g/L (−)-carvone (carvone used as internal standard). The final solution was analyzed by GC-MS.

8. EDA consumption in the cell culture expressing the artificial pathway. *E. coli* cells co-transformed with pJBEI6410 and pJHA170 were grown as described in 7, except for the following steps. After addition of 50 μM IPTG and 0.1 μM Ir(Me)MPIX, the cultures were incubated at 30° C., 200 rpm for 12 h. To the cultures were added 100 μL EDA stock solution (0.2 M in EtOH) to give a final concentration of 2 mM, and the mixture was further incubated at 30° C., 200 rpm. Aliquots of cell culture (600 μL) were removed from the tube at each two-hour interval over 10 h. The aliquots were extracted with ethyl acetate (600 μL, containing 80 ng/L dodecane as internal standard). The organic phase was analyzed by GC-FID.

9. Cell viability test with CFU (colony forming units) assay. *E. coli* cells co-transformed with pJBEI6410 and pJHA170 were grown as described in 7, except for the following steps. After addition of 50 μM IPTG and 0.1 μM Ir(Me)MPIX, the cultures were incubated at 30° C., 200 rpm for 12 h. A portion of cell culture (1.4 mL) was transferred into Falcon 14 mL round-bottom tube. The stock solutions of EDA in ethanol were added to the cell culture to give final concentration of 0 mM, 2 mM, 5 mM, 20 mM EDA and 1% (v/v) ethanol. For the control group, only sterile $ddH_2O$ (1%, v/v) was added. The cultures were further incubated at 30° C., 200 rpm for 4 h. Then the cultures were diluted $10^5$ times. Aliquots of diluted cell suspension (50 μL) were plated onto LB agar plates. The plates were incubated at 30° C. for 24 h. The colonies grown on the plates were manually counted and the percentage of viable cells in each group was calculated by normalizing the number of colonies grown in the control group as 100%.

10. Cytotoxicity of Ir(Me)MPIX and cyclopropyl limonene. Ir(Me)MPIX; pJHA047 (containing hug operon) or pBbS5K (empty vector) was transformed into chemically competent BL21(DE3) (NEB) cells. Individual colonies from freshly transformed plates (incubated at 30° C.) were inoculated into 2 mL M9-rich media supplemented with appropriate antibiotics. A 1:100 dilution of overnight cultures into 300 μL M9-rich media was performed in a 48-well plate. To the culture in the wells of this plate were added 1.5 μL of solutions of Ir(Me)MPIX in DMSO varying in concentration (0 mM, 0.02 mM, 0.2 mM, 2 mM) to give final concentration of 0 μM, 0.1 μM, 1 μM, 10 μM Ir(Me)MPIX. The $OD_{600}$ values were recorded by a plate reader (F200 or F200pro, Tecan) set at 30° C.

Cyclopropyl limonene; BL21(DE3) cells co-transformed with pHug21 (coding for HUG system) and pJHA110 (coding for CYP119 mutant) were grown and cultivated as described above. The stock solution of cyclopropyl limonene in ethanol was added to the cell culture to give final concentration of 0, 0.2, 1, 5, 25 mg/L cyclopropyl limonene and 1% (v/v) ethanol. The $OD_{600}$ values were recorded by a plate reader (F200 or F200pro, Tecan) set at 30° C.

11. Sample preparation for ICP-MS measurement, (a) Cell fractionation (10 mL culture);[7] A plasmid containing CYP119 mutant (pJHA110) was co-transformed with a plasmid (pHug21) encoding the heme transport system HUG or an empty vector backbone (pBbS5a) into chemically competent BL21(DE3) (NEB) cells. Individual colonies from freshly transformed plates were inoculated into 4 mL M9-rich media supplemented with 100 μg/mL carbenicillin and 25 μg/mL kanamycin. The cultures were grown overnight at 37° C. and 200 rpm. In a 50 mL Falcon tube, 10 mL of M9-rich media was inoculated with 100 μL of overnight starter culture and incubated at 37° C. and 200 rpm to an $OD_{600}$ of 0.7-0.8. The cultures were then induced by adding 50 μM IPTG, at which time 2 μL of a 0.5 mM solution of Ir(Me)MPIX in DMSO was added to give a final Ir(Me)MPIX concentration of 0.1 μM. Upon induction, the incubation temperature was reduced to 30° C., and expression was allowed to continue for 18 h at 200 rpm. Cells were harvested by centrifugation (4000 rpm, 15 min, 4° C.) and the supernatants were carefully removed by pipette.

Periplasmic extraction; The cell pellet was suspended in 1 mL of spheroplast buffer (0.1 M TRIS, 500 mM sucrose, 0.5 mM EDTA, pH 8.0), incubated on ice for 5 min, and centrifuged (10000 rpm, 5 min, 4° C.). The supernatant was carefully removed. The pellet was then resuspended in 1 mL of hypotonic solution (0.1 mM $MgCl_2$) and the sample was incubated for 5 min on ice. After centrifugation, the recovered supernatant was combined with the supernatant from the sucrose wash. The resulting periplasmic fraction (2 mL) was carefully transferred to a new tube and the pellet was incubated on ice for subsequent cytoplasmic extraction.

Cell disruption: The pellet from previous step was suspended in 5 mL lysis buffer (50 mM TRIS, 100 mM NaCl, pH 8.0). The suspension was sonicated (5 s on, 5 s off, 10 min, 70% power) on ice using a Qsonica Q125 sonicator. After centrifugation at 10000 rpm for 30 min, the supernatant was transferred to a new tube as the cytoplasmic fraction and the pellet, resuspended in 5 mL TRIS lysis buffer, was reserved as the insoluble fraction.

(b) Protein purification (100 mL culture); A plasmid containing CYP119 mutant (pJHA110) was co-transformed with a plasmid (pHug21) encoding the heme transport system HUG, or an empty vector backbone (pBbS5a) into chemically competent BL21(DE3) (NEB) cells. Individual colonies from freshly transformed plates were inoculated into 4 mL M9-rich media supplemented with 100 μg/mL carbenicillin and 25 μg/mL kanamycin. The cultures were grown overnight at 37° C. and 200 rpm. In a 500 mL Erlenmeyer flask, 100 mL of M9-rich media was inoculated with 1 mL of overnight starter culture and incubated at 37° C. and 200 rpm to an $OD_{600}$ of 0.7~0.8. The cultures were then induced by adding 50 μM IPTG, at which time 20 μL of a 0.5 mM solution of Ir(Me)MPIX in DMSO was added to give a final Ir(Me)MPIX concentration of 0.1 µM. Upon induction, the incubation temperature was reduced to 30° C., and expressions were allowed to continue for 18 h at 200 rpm. Cells were harvested by centrifugation and stored at −20° C. until purification.

Ni-NTA affinity chromatography; Cell pellets were thawed at room temperature, resuspended in 10 mL lysis buffer (50 mM TRIS, 100 mM NaCl, pH 7.5), and lysed on ice by sonication (5 s on, 5 s off, 10 min, 70% power). Cell debris was removed by centrifugation (10000 rpm, 45 min, 4° C.). The supernatants were incubated with Ni-NTA agarose (50% suspension, 4 mL) on a tube rotator (15 min, 4° C., 20 rpm) and poured into glass frits (coarse, 50 mL). The resin was washed (3×35 mL) with Ni-NTA lysis buffer (50 mM NaPi, 250 mM NaCl, 10 mM Imidazole, pH 8.0). The desired protein was eluded with 15 mL Ni-NTA elusion buffer (50 mM NaPi, 250 mM NaCl, 250 mM Imidazole, pH 8.0) and concentrated to 1 mL with a 30 kDa molecular weight cut-off Amicon centrifugal filtration device (EMD Millipore).

(c) ICP-MS analysis; Conc. $HNO_3$ was added to each sample (1 mL) in to make a final concentration of 4% (v/v). After microwave digestion (140° C., 30 min), the samples were analyzed by ICP-MS (Elemental Analysis Core, Oregon Health & Science University).

12. Reactions catalyzed by Ir-CYP119 reconstituted in vitro. Apo-CYP119 was expressed and purified as described earlier.[1] The apo-protein and Ir(Me)MPIX cofactor were combined in a 2.5:1 molar ratio. The buffer of the protein solution was subsequently exchanged to TRIS buffer (20 mM, pH 7.5) using a NAP-10 column (GE Healthcare). On the bench, 1 mL of catalyst stock solution (1.8 mg/mL CYP119, 40% [Ir]) was added to a 4 mL glass vial equipped with a micro stirring bar. To the reaction vial, 10 µL of 0.125 M stock solution of limonene in EtOH was added. The reaction vial was sealed with a cap containing a septum. The syringes of a multichannel syringe pump were loaded with a stock solution of EDA in DMSO (20 µL of 0.25 M solution of EDA in DMSO), and the EDA solution was added to the reaction over 1.5 h. The reaction was quenched upon the conclusion of the addition of EDA by adding 100 µL of 2 N HCl and extracted with 1 mL dodecane stock solution (0.1% (v/v) in ethyl acetate). The organic layer was then transferred to a separate vial for GC analysis.

13. General procedure for the synthesis of cyclopropyl limonene standard. To a solution of alkene (0.2 M) and Ir(Me)MPIX (0.5 mol % with respect to alkene) in dry DCM ($CH_2Cl_2$), a solution of ethyl diazoacetate (1 M) in dry DCM was added slowly while the reaction mixture was vigorously stirred. After complete addition of EDA, the reaction was stirred for 1 h. Then, the volatile materials were evaporated under reduced pressure, and the residue was purified by column chromatography on silica gel, with a mixture of hexane and ethyl acetate (100:0 to 95:5 gradient) as the eluent. Fractions of the pure product(s) were combined, and the solvent evaporated, yielding cyclopropanation products.

14. Binding affinity of apo-CYP119 towards Ir(Me)MPIX/hemin. Intrinsic fluorescence quenching;[8] Modified from a reported procedure, aliquots (10 µL) of metalloporphyrin stock solutions (in DMSO) were added to a solution containing 0.15 mg/L apo-CYP119 (CYP119-141 mutant, 800 µL, 10 mM TRIS buffer, pH 8.0). This addition caused the concentration of the protein to decrease from its initial value to a final concentration of 0.148 mg/L in the process. After each addition, the emission spectrum of CYP119 was recorded upon excitation at 294 nm. In quenching experiments, the concentration of the chromophore (CYP119 or porphyrin) was kept sufficiently low (<0.15) to ensure uniform light absorption throughout the sample and reduced inner filter effects. The fluorescence emission intensity was calculated as the integral of the emission spectrum in the recorded wavelength range (305-450 nm). The corrected emission intensity was analyzed with the Benesi-Hildebrand equation.

TABLE 2

GC Methods used to separate diastereomers of the cyclopropanation products and biosynthesized products.

| Products[a] | Instrument | Column | Method | Retention Times |
|---|---|---|---|---|
| (ketone-cyclohexenone with cyclopropyl-$CO_2Et$) | GC-FID | DB-wax (15 m × 0.32 mm × 0.25 µm) | 40° C. 5° C./min to 140° C.; hold for 20 min; 30° C./min to 245° C., hold 3 min | P1: 29.472 min (major) P2: 30.432 min P3: 34.848 min P4: 35.507 min |
| (limonene-cyclopropyl-$CO_2Et$) | GC-FID | CycloSil-B (30 m × 0.25 mm × 0.25 µm) | 40° C. 15° C./min to 150° C.; hold 43 min; 30° C./min to 245° C. hold 3 min | P1: 33.563 min P2: 34.288 min (major) P3: 43.310 min P4: 44.733 min |
| (limonene-cyclopropyl-$CO_2Et$) | GC-MS EIC: 93, 121 and 222 | CycloSil-B (30 m × 0.25 mm × 0.25 µm) | 40° C. 15° C./min to 150° C.; hold 43 min; 30° C./min to 245° C., hold 3 min | P1: 14.741 min P2: 14.967 min (major) P3: 17.846 min P4: 18.304 min |

TABLE 2-continued

GC Methods used to separate diastereomers of the cyclopropanation products and biosynthesized products.

| Products[a] | Instrument | Column | Method | Retention Times |
|---|---|---|---|---|
| Ethyl diazoacetate | GC-FID | DB-wax (15 m × 0.32 mm × 0.25 μm) | 40° C., 10° C./min to 80° C.,; hold 0 min; 30° C./min to 245° C., hold 2 min | 2.572 min |
| (-)-limonene | GC-MS EIC: 93, 121 and 136 | HP-5 (30 m × 0.25 mm × 0.25 μm) | 80° C. hold 1 min; 20° C./min to 120° C.; 50° C./min to 250° C. | 3.074 min |

[a]The configuration of the major diastereomeric product of the cyclopropanation of (-)-carvone was determined in the prior publication.
[b]The configuration of the major diastereomeric product of the cyclopropanation of (-)-limonene is proposed by analogy to the cyclopropane product of (-)-carvone.

TABLE 3

Summary of the binding constants for the formation of the Fe(Cl)PPIX and Ir(Me)MPIX complexes with apo-CYP119, yielded by the Benesi-Hildebrand analysis of fluorescence quenching data.

| Cofactor | $K_b$ (M$^{-1}$) | $K_d$ (μM) |
|---|---|---|
| Fe(Cl)PPIX | 6.7(0.7) × 10$^5$ | 1.5(0.2) |
| Ir(Me)MPIX | 4.2(0.3) × 10$^5$ | 2.4(0.2) |

Binding data of hemoproteins from literature [9]

| Cofactor | Protein | $K_d$ |
|---|---|---|
| Fe(Cl)PPIX | apo-ascorbate peroxidase | 0.19 μM |
| Fe(Cl)PPIX | apo-myoglobin | 0.60 μM |
| Reduced Fe(Cl)PPIX | apo-myoglobin | 3.1 fM |

TABLE 4

The comparison of the diastereoselectivity of the cyclopropanation of (-)-limonene catalyzed by Ir-CYP119 mutants reconstituted in vitro and whole cells harboring Ir-CYP119 mutants.

| CYP119 mutants | in vivo diastereoselectivity ($P_2/P_{total}$)[a] | in vitro diastereoselectivity ($P_2/P_{total}$)[b] |
|---|---|---|
| P (C317G, T213G, V254L, L155W) | 53% | 20% |
| P/256W | 63% | 48% |
| P/256W/254A | 72% | 60% |

[a]The data are shown as the average from three biological repeats.
[b]The data are shown as the average from two replicate experiments.

TABLE 5

ICP-MS measurement of CYP119 purified from E. coli co-expressing the heme transport system and CYP119 (pJHA110).[a]

| | protein yield (mg) | protein yield (μmol) | Ir (nmol)[c] | % Ir recovery[d] |
|---|---|---|---|---|
| RFP/CYP119[b] | | | | |
| Replicate 1 | 1.88 | 0.042 | 0.59 | 5.9% |
| Replicate 2 | 2.55 | 0.057 | 0.62 | 6.2% |
| Replicate 3 | 2.36 | 0.052 | 0.66 | 6.6% |
| | | | Average | 6.3 ± 0.4% |
| HUG/CYP119[e] | | | | |
| Replicate 1 | 3.63 | 0.081 | 3.15 | 31.5% |
| Replicate 2 | 3.65 | 0.081 | 3.66 | 36.6% |
| Replicate 3 | 2.96 | 0.066 | 3.08 | 30.8% |
| | | | Average | 33.0 ± 3.1% |
| ChuA/Ton/CYP119[f] | | | | |
| Replicate 1 | 2.52 | 0.056 | 0.83 | 8.3% |
| Replicate 2 | 2.23 | 0.050 | 0.69 | 6.9% |
| Replicate 3 | 2.22 | 0.049 | 0.87 | 8.7% |
| | | | Average | 8.0 ± 0.9% |

[a]The cell culture (100 mL) was cultivated and the CYP119 was purified following the protocol described in section 11 (b).
[b]E. coli cells were transformed with pBbS5a (plasmid encoding RFP as control) and pJHA110 (plasmid encoding CYP119 with lacUV5 promoter).
[c]The data show the total amount of Ir present in the purified protein.
[d]The percentages of added iridium (0.1 μM) that were recovered from the purified protein.
[e]E. coli cells were transformed with pHug21 (plasmid encoding the HUG system) and pJHA110 (plasmid encoding CYP119 with lacUV5 promoter).
[f]E. coli cells were transformed with pJHA184 (plasmid encoding ChuA and Ton complex) and pJHA110 (plasmid encoding CYP119 with lacUV5 promoter).

TABLE 6

ICP-MS measurement of CYP119 purified from E. coli co-expressing the heme transport system and CYP119 (pJHA110).[a]

| HUG/ CYP119 | protein yield (mg) | protein yield (μmol) | Fe (μmol)[b] | Fe: CYP119[c] | Ir (μmol)[d] | Ir: CYP119[e] |
|---|---|---|---|---|---|---|
| Replicate 1 | 16.26 | 0.36 | 0.031 | 8.5% | 0.040 | 11.1% |
| Replicate 2 | 17.26 | 0.38 | 0.035 | 9.1% | 0.041 | 10.8% |
| Replicate 3 | 15.81 | 0.35 | 0.044 | 12.4% | 0.039 | 11.0% |

[a]The cell culture (700 mL) was cultivated and the CYP119 was purified following the protocol described in section 11 (b) except that 0.2 mg/L Ir(Me)MPIX was supplemented upon the induction of protein expression. The purified protein was dialyzed against 10 mM TRIS buffer (pH 8) before concentration and acid digestion to remove the residual iron in Ni-NTA elution buffer.
[b]The data show the total amount of Fe present in the purified protein. The concentration of Fe in ICP-OES (Inductively coupled plasma-optical emission spectrometry) samples were measured at an emission wavelength of 259 nm.
[c]Fe:CYP119 is calculated as the molar ratio of iron and CYP119. The value represents the percentage of heme-containing CYP119 in the purified protein sample by assuming that all Fe exists in the form of heme and binds to CYP119.
[d]The data show the total amount of Ir present in the purified protein. The concentration of Ir in ICP-OES samples was measured at an emission wavelength of 212 nm.
[e]Ir:CYP119 is calculated as the molar ratio of iridium and CYP119. The value represents the percentage of Ir(Me)MPIX-containing CYP119 in the purified protein sample by assuming that all Ir exists in the form of iridium porphyrin and binds to CYP119.

References cited in the METHOD section above:
1 Key, H. M. et al. Beyond Iron: Iridium-Containing P450 Enzymes for Selective Cyclo-propanations of Structurally Diverse Alkenes. *ACS Cent. Sci.* 3, 302-308 (2017).
2 Dydio, P. et al. An Artificial Metalloenzyme with the Kinetics of Native Enzymes. *Science* 354, 102 (2016).
3 Villarreal, D. M. et al. Enhancement of Recombinant Hemoglobin Production in *Escherichia coli* BL21(DE3) Containing the *Plesiomonas shigelloides* Heme Transport System. *Appl. Environ. Microbiol.* 74, 5854 (2008).

4 Lee, T. S. et al. BglBrick vectors and datasheets: A synthetic biology platform for gene expression. *J. Biol. Eng.* 5, 12 (2011).

5 Reister, M. et al. Complete genome sequence of the Gram-negative probiotic *Escherichia coli* strain Nissle 1917. *J. Biotechnol.* 187, 106-107 (2014).

6 Alonso-Gutierrez, J. et al. Metabolic engineering of *Escherichia coli* for limonene and perillyl alcohol production. *Metab. Eng.* 19, 33-41 (2013).

7 Malherbe, G., Humphreys, D. P. & Dave, E. A robust fractionation method for protein subcellular localization studies in *Escherichia coli*. *BioTechniques* 66, 171-178 (2019).

8 Hu, J., Allen, R., Rozinek, S. & Brancaleon, L. Experimental and computational characterization of photosensitized conformational effects mediated by protoporphyrin ligands on human serum albumin. *Photochem. Photobiol. Sci.* 16, 694-710 (2017).

9 Leung, G. C. H., Fung, S. S. P., Dovey, N. R. B., Raven, E. L. & Hudson, A. J. Precise determination of heme binding affinity in proteins. *Anal. Biochem.* 572, 45-51 (2019).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified host cell capable of producing an unnatural compound, the host cell comprising:
   (1) a P450 enzyme comprising an amino acid sequence at least 70% identical to SEQ ID NO:1, and W, M, Y, or C at position 256; and
   (2) a heterologous heme transport transmembrane protein, or homologue thereof,
   wherein the heterologous heme transport transmembrane protein in the host cell transports an artificial cofactor for uptake into the P450 enzyme.

2. The genetically modified host cell of claim 1, wherein the P450 enzyme comprises an apo-CYP119.

3. The genetically modified host cell of claim 1, wherein the artificial cofactor comprises a porphyrin and a metal or M(L), wherein M is a metal and L is a ligand.

4. The genetically modified host cell of claim 3, wherein the porphyrin has the following formula:

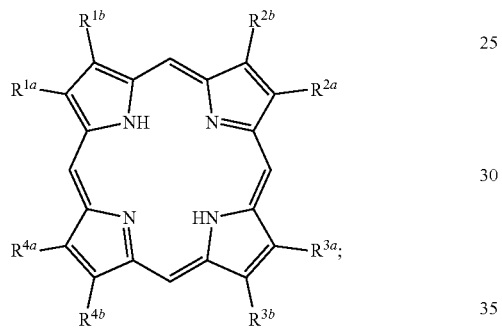

wherein $R^{1a}$, $R^{1b}$, $R^{2a}$, $R^{2b}$, $R^{3a}$, $R^{3b}$, $R^{4a}$ and $R^{4b}$ are each independently selected from the group consisting of hydrogen, $C_{1-6}$ alkyl, $C_{2-6}$ alkenyl, $C_{2-6}$ alkynyl, $C_{3-8}$ cycloalkyl and $C_{6-10}$ aryl, wherein the alkyl is optionally substituted with —C(O)OR$^5$ wherein $R^5$ is hydrogen or $C_{1-6}$ alkyl.

5. The genetically modified host cell of claim 4, wherein the porphyrin is pyropheophorbide-a, pheophorbide, chlorin e6, purpurin, or purpurinimide.

6. The genetically modified host cell of claim 4, wherein the porphyrin is one selected from the group consisting of:

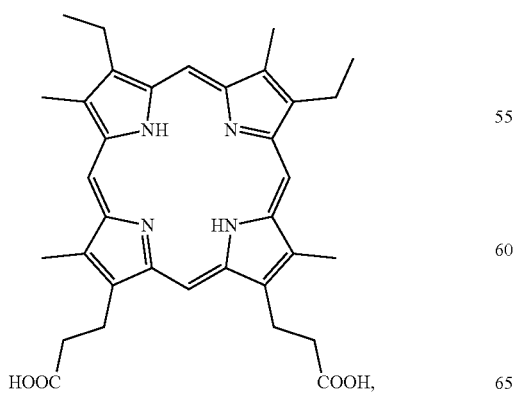

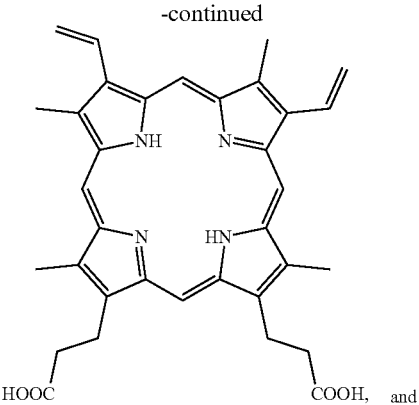

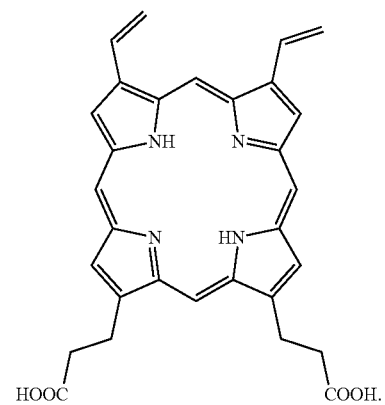

7. The genetically modified host cell of claim 3, wherein the metal is a transition metal.

8. The genetically modified host cell of claim 7, wherein the transition metal is Ir, Pd, Pt, Ag, Fe, Mn, Ru, Co, Zn, Cu, Ni, Cr, Rh or Os.

9. The genetically modified host cell of claim 7, wherein the transition metal is Ir, Pd, Pt or Ag.

10. The genetically modified host cell of claim 3, wherein the ligand is an alkyl, aryl, vinyl, or alkynyl.

11. The genetically modified host cell of claim 3, wherein the artificial cofactor comprises the following structure:

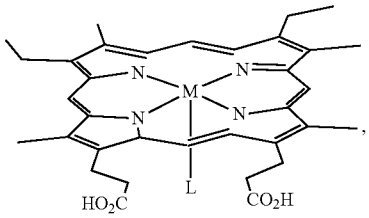

wherein M is a metal, and L is an alkyl, aryl, vinyl, or alkynyl.

12. The genetically modified host cell of claim 11, wherein the artificial cofactor comprises the following structure:

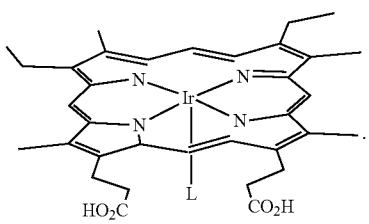

13. The genetically modified host cell of claim 11, wherein the artificial cofactor comprises the following structure:

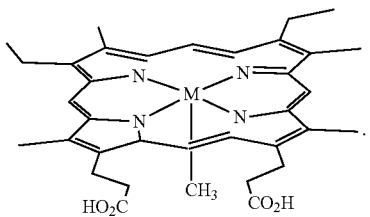

14. The genetically modified host cell of claim 13, wherein the artificial cofactor comprises the following structure:

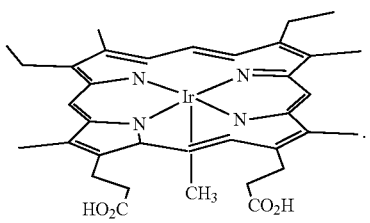

15. The genetically modified host cell of claim 1, wherein the unnatural compound has the following structure:

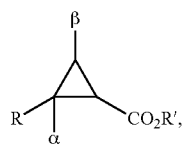

(I)

wherein α and β are each independently a —H or an alkyl group, and wherein R and α may form a ring structure, R is an alkyl group comprising 3, 4, 5, 6, 7, 8, 9, 10, or more carbon atoms, optionally R comprises one or more double bonds, one or more alkyl substituents, one or more ketone substituents, and/or one or more hydroxyl substituents, optionally R comprises a cycloalkane optionally comprising one or more double bonds, one or more alkyl substituents, one or more ketone substituents, and/or one or more hydroxyl substituents.

16. The genetically modified host cell of claim 15, wherein the unnatural compound has the following structure:

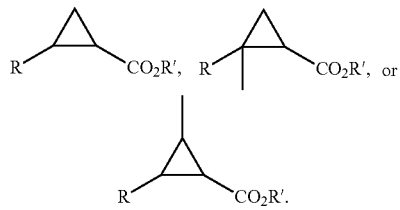

17. The genetically modified host cell of claim 15, wherein the unnatural compound comprises a cyclopropanated pinene, linalool, nootkatone, eugenol, terpineol, polyketide, flavonoid, cannabinoid, or a compound wherein the structure (I) comprises one or more alkene.

18. The genetically modified host cell of claim 1, wherein the P450 enzyme comprises (i) W at position 256 of SEQ ID NO: 1, (ii) M at position 256 of SEQ ID NO: 1, (iii) Y at position 256 of SEQ ID NO: 1, (iv) C at position 256 of SEQ ID NO: 1, or (v) G at position 317, G at position 213, A at position 254, W at position 155, and W at position 256 of SEQ ID NO: 1.

19. The genetically modified host cell of claim 1, wherein the heme transport transmembrane protein comprises an amino acid sequence having at least 70% identity with SEQ ID NO:2.

20. A method for a genetically modified host cell producing an unnatural compound, comprising: (a) providing a genetically modified host cell of claim 1, (b) introducing the artificial cofactor into the host cell, (c) culturing or growing the host cell in a suitable culture or medium such that the unnatural compound is produced, and (d) extracting or separating the unnatural compound from the rest of the culture or medium, and/or host cell.

21. The genetically modified host cell of claim 1, wherein the P450 enzyme comprises an amino acid sequence having at least 80% identity with SEQ ID NO:1.

22. The genetically modified host cell of claim 21, wherein the P450 enzyme comprises an amino acid sequence having at least 90% identity with SEQ ID NO:1.

23. The genetically modified host cell of claim 22, wherein the P450 enzyme comprises an amino acid sequence having at least 95% identity with SEQ ID NO:1.

24. The genetically modified host cell of claim 23, wherein the P450 enzyme comprises an amino acid sequence having at least 99% identity with SEQ ID NO:1.

* * * * *

SEQUENCE LISTING

```
<160> NUMBER OF SEQ ID NOS: 2

<210> SEQ ID NO 1
<211> LENGTH: 368
<212> TYPE: PRT
<213> ORGANISM: Sulfolobus acidocaldarius

<400> SEQUENCE: 1

Met Tyr Asp Trp Phe Ser Glu Met Arg Lys Asp Pro Val Tyr Tyr
1               5                   10                  15

Asp Gly Asn Ile Trp Gln Val Phe Ser Tyr Arg Tyr Thr Lys Glu Val
                20                  25                  30

Leu Asn Asn Phe Ser Lys Phe Ser Ser Asp Leu Thr Gly Tyr His Glu
            35                  40                  45

Arg Leu Glu Asp Leu Arg Asn Gly Lys Ile Arg Phe Asp Ile Pro Thr
        50                  55                  60

Arg Tyr Thr Met Leu Thr Ser Asp Pro Pro Leu His Asp Glu Leu Arg
    65                  70                  75                  80

Ser Met Ser Ala Asp Ile Phe Ser Pro Gln Lys Leu Gln Thr Leu Glu
                85                  90                  95

Thr Phe Ile Arg Glu Thr Thr Arg Ser Leu Leu Asp Ser Ile Asp Pro
            100                 105                 110

Arg Glu Asp Asp Ile Val Lys Lys Leu Ala Val Pro Leu Pro Ile Ile
        115                 120                 125

Val Ile Ser Lys Ile Leu Gly Leu Pro Ile Glu Asp Lys Glu Lys Phe
    130                 135                 140

Lys Glu Trp Ser Asp Leu Val Ala Phe Arg Leu Gly Lys Pro Gly Glu
145                 150                 155                 160

Ile Phe Glu Leu Gly Lys Lys Tyr Leu Glu Leu Ile Gly Tyr Val Lys
                165                 170                 175

Asp His Leu Asn Ser Gly Thr Glu Val Val Ser Arg Val Val Asn Ser
            180                 185                 190

Asn Leu Ser Asp Ile Glu Lys Leu Gly Tyr Ile Ile Leu Leu Leu Ile
        195                 200                 205

Ala Gly Asn Glu Thr Thr Thr Asn Leu Ile Ser Asn Ser Val Ile Asp
    210                 215                 220

Phe Thr Arg Phe Asn Leu Trp Gln Arg Ile Arg Glu Glu Asn Leu Tyr
225                 230                 235                 240

Leu Lys Ala Ile Glu Glu Ala Leu Arg Tyr Ser Pro Pro Val Met Arg
                245                 250                 255
```

```
Thr Val Arg Lys Thr Lys Glu Arg Val Lys Leu Gly Asp Gln Thr Ile
                260                 265                 270

Glu Glu Gly Glu Tyr Val Arg Val Trp Ile Ala Ser Ala Asn Arg Asp
            275                 280                 285

Glu Glu Val Phe His Asp Gly Glu Lys Phe Ile Pro Asp Arg Asn Pro
        290                 295                 300

Asn Pro His Leu Ser Phe Gly Ser Gly Ile His Leu Cys Leu Gly Ala
305                 310                 315                 320

Pro Leu Ala Arg Leu Glu Ala Arg Ile Ala Ile Glu Glu Phe Ser Lys
                325                 330                 335

Arg Phe Arg His Ile Glu Ile Leu Asp Thr Glu Lys Val Pro Asn Glu
            340                 345                 350

Val Leu Asn Gly Tyr Lys Arg Leu Val Val Arg Leu Lys Ser Asn Glu
        355                 360                 365

<210> SEQ ID NO 2
<211> LENGTH: 660
<212> TYPE: PRT
<213> ORGANISM: E. coli

<400> SEQUENCE: 2

Met Ser Arg Pro Gln Phe Thr Ser Leu Arg Leu Ser Leu Leu Ala Leu
1               5                   10                  15

Ala Val Ser Ala Thr Leu Pro Thr Phe Ala Phe Ala Thr Glu Thr Met
                20                  25                  30

Thr Val Thr Ala Thr Gly Asn Ala Arg Ser Ser Phe Glu Ala Pro Met
            35                  40                  45

Met Val Ser Val Ile Asp Thr Ser Ala Pro Glu Asn Gln Thr Ala Thr
        50                  55                  60

Ser Ala Thr Asp Leu Leu Arg His Val Pro Gly Ile Thr Leu Asp Gly
65                  70                  75                  80

Thr Gly Arg Thr Asn Gly Gln Asp Val Asn Met Arg Gly Tyr Asp His
                85                  90                  95

Arg Gly Val Leu Val Leu Val Asp Gly Val Arg Gln Gly Thr Asp Thr
            100                 105                 110

Gly His Leu Asn Gly Thr Phe Leu Asp Pro Ala Leu Ile Lys Arg Val
        115                 120                 125

Glu Ile Val Arg Gly Pro Ser Ala Leu Leu Tyr Gly Ser Gly Ala Leu
    130                 135                 140

Gly Gly Val Ile Ser Tyr Asp Thr Val Asp Ala Lys Asp Leu Leu Gln
145                 150                 155                 160

Glu Gly Gln Ser Ser Gly Phe Arg Val Phe Gly Thr Gly Thr Gly
                165                 170                 175

Asp His Ser Leu Gly Leu Gly Ala Ser Ala Phe Gly Arg Thr Glu Asn
            180                 185                 190

Leu Asp Gly Ile Val Ala Trp Ser Ser Arg Asp Arg Gly Asp Leu Arg
        195                 200                 205

Gln Ser Asn Gly Glu Thr Ala Pro Asn Asp Glu Ser Ile Asn Asn Met
    210                 215                 220

Leu Ala Lys Gly Thr Trp Gln Ile Asp Ser Ala Gln Ser Leu Ser Gly
225                 230                 235                 240

Leu Val Arg Tyr Tyr Asn Asn Asp Ala Arg Glu Pro Lys Asn Pro Gln
                245                 250                 255

Thr Val Glu Ala Ser Asp Ser Ser Asn Pro Met Val Asp Arg Ser Thr
            260                 265                 270
```

```
Ile Gln Arg Asp Ala Gln Leu Ser Tyr Lys Leu Ala Pro Gln Gly Asn
        275                 280                 285

Asp Trp Leu Asn Ala Asp Ala Lys Ile Tyr Trp Ser Glu Val Arg Ile
290                 295                 300

Asn Ala Gln Asn Thr Gly Ser Ser Gly Glu Tyr Arg Glu Gln Ile Thr
305                 310                 315                 320

Lys Gly Ala Arg Leu Glu Asn Arg Ser Thr Leu Phe Ala Asp Ser Phe
                325                 330                 335

Ala Ser His Leu Leu Thr Tyr Gly Gly Glu Tyr Tyr Arg Gln Glu Gln
                340                 345                 350

His Pro Gly Gly Ala Thr Thr Gly Phe Pro Gln Ala Lys Ile Asp Phe
                355                 360                 365

Ser Ser Gly Trp Leu Gln Asp Glu Ile Thr Leu Arg Asp Leu Pro Ile
370                 375                 380

Thr Leu Leu Gly Gly Thr Arg Tyr Asp Ser Tyr Arg Gly Ser Ser Asp
385                 390                 395                 400

Gly Tyr Lys Asp Val Asp Ala Asp Lys Trp Ser Ser Arg Ala Gly Met
                405                 410                 415

Thr Ile Asn Pro Thr Asn Trp Leu Met Leu Phe Gly Ser Tyr Ala Gln
                420                 425                 430

Ala Phe Arg Ala Pro Thr Met Gly Glu Met Tyr Asn Asp Ser Lys His
                435                 440                 445

Phe Ser Ile Gly Arg Phe Tyr Thr Asn Tyr Trp Val Pro Asn Pro Asn
450                 455                 460

Leu Arg Pro Glu Thr Asn Glu Thr Gln Glu Tyr Gly Phe Gly Leu Arg
465                 470                 475                 480

Phe Asp Asp Leu Met Leu Ser Asn Asp Ala Leu Glu Phe Lys Ala Ser
                485                 490                 495

Tyr Phe Asp Thr Lys Ala Lys Asp Tyr Ile Ser Thr Thr Val Asp Phe
                500                 505                 510

Ala Ala Ala Thr Thr Met Ser Tyr Asn Val Pro Asn Ala Lys Ile Trp
                515                 520                 525

Gly Trp Asp Val Met Thr Lys Tyr Thr Thr Asp Leu Phe Ser Leu Asp
530                 535                 540

Val Ala Tyr Asn Arg Thr Arg Gly Lys Asp Thr Asp Thr Gly Glu Tyr
545                 550                 555                 560

Ile Ser Ser Ile Asn Pro Asp Thr Val Thr Ser Thr Leu Asn Ile Pro
                565                 570                 575

Ile Ala His Ser Gly Phe Ser Val Gly Trp Val Gly Thr Phe Ala Asp
                580                 585                 590

Arg Ser Thr His Ile Ser Ser Ser Tyr Ser Lys Gln Pro Gly Tyr Gly
                595                 600                 605

Val Asn Asp Phe Tyr Val Ser Tyr Gln Gly Gln Ala Leu Lys Gly
                610                 615                 620

Val Thr Thr Thr Leu Val Leu Gly Asn Ala Phe Asp Lys Glu Tyr Trp
625                 630                 635                 640

Ser Pro Gln Gly Ile Pro Gln Asp Gly Arg Asn Gly Lys Ile Phe Val
                645                 650                 655

Ser Tyr Gln Trp
                660
```